(12) United States Patent
Ray et al.

(10) Patent No.: US 8,198,288 B2
(45) Date of Patent: Jun. 12, 2012

(54) TETRAHYDROPYRROLOPYRIMIDINEDIONES AND THEIR USE IN THERAPY

(75) Inventors: Nicholas Charles Ray, Essex (GB); Harry Finch, Essex (GB); Christine Edwards, Essex (GB); Elizabeth O'Connor, Essex (GB)

(73) Assignee: Pulmagen Therapeutics (Inflammation) Limited, Slough (GB)

( * ) Notice: Subject to any disclaimer, the term of this patent is extended or adjusted under 35 U.S.C. 154(b) by 641 days.

(21) Appl. No.: 12/264,621

(22) Filed: Nov. 4, 2008

(65) Prior Publication Data
US 2009/0093477 A1    Apr. 9, 2009

Related U.S. Application Data

(63) Continuation-in-part of application No. PCT/GB2007/001638, filed on May 3, 2007, and a continuation-in-part of application No. PCT/GB2007/002825, filed on Jul. 25, 2007, and a continuation-in-part of application No. PCT/GB2008/055439, filed on May 2, 2008.

(30) Foreign Application Priority Data

| May 4, 2006 | (GB) | ................................. 0608844.7 |
| Jun. 23, 2006 | (GB) | ................................. 0612544.7 |

(51) Int. Cl.
| C07D 487/04 | (2006.01) |
| A61K 31/519 | (2006.01) |
| A61P 11/08 | (2006.01) |
| A61P 17/06 | (2006.01) |

(52) U.S. Cl. ..................... 514/265.1; 544/280
(58) Field of Classification Search .................. 544/280; 514/265.1
See application file for complete search history.

(56) References Cited

FOREIGN PATENT DOCUMENTS

| WO | WO 98/28301 | 7/1998 |
| WO | WO 99/12933 | 3/1999 |
| WO | WO 02/04453 | 1/2002 |
| WO | WO 2004/024700 A | 3/2004 |
| WO | WO 2004/024701 A | 3/2004 |
| WO | WO 2006/082412 A | 8/2006 |
| WO | WO 2007/042815 A | 4/2007 |
| WO | WO 2007/129060 A | 11/2007 |

OTHER PUBLICATIONS

Namazi, H., et al. "Investigation the Chemical Reactivity of Positions N-3, C-5 and C-6-Methyl Group in Biginelli Type Compounds and Synthesis of New Dihydropyrimidine Derivatives" *Journal of Heterocyclic Chemistry*, Sep. 2001, pp. 1051-1054, vol. 38.

*Primary Examiner* — Susanna Moore
(74) *Attorney, Agent, or Firm* — Saliwanchik, Lloyd & Eisenschenk

(57) ABSTRACT

The subject invention provides compounds of formula (1):

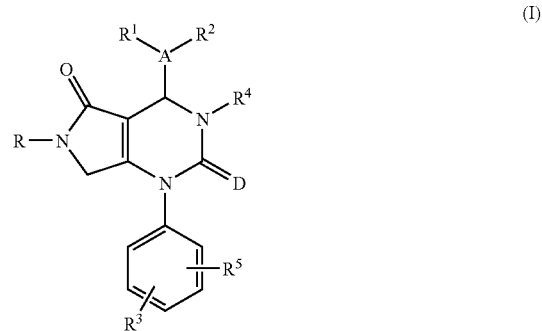

including monomers and multimers thereof that are inhibitors of human neutrophil elastase (HNE) activity and are useful in the treatment of diseases or conditions in which HNE plays a part.

14 Claims, No Drawings

TETRAHYDROPYRROLOPYRIMIDINEDIONES AND THEIR USE IN THERAPY

CROSS-REFERENCE TO A RELATED APPLICATION

This application is a continuation-in-part application of International Application No. PCT/GB2007/001638, filed May 3, 2007, which claims priority to Great Britain Applications Nos. 0608844.7, filed May 4, 2006 and 0612544.7, filed Jun. 23, 2006. This application is also a continuation-in-part of International Application No. PCT/GB2007/002825, filed Jul. 25, 2007 and PCT/GB2008/055439, filed May 2, 2008, all of which are incorporated herein in their entirety.

FIELD OF THE INVENTION

This invention relates to heterocyclic compounds which are substituted 3,4,6,7-tetrahydro-1H-pyrrolo[3,4-d]pyrimidine-2,5-diones, and their use in therapy.

BACKGROUND TO THE INVENTION

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (Bieth, G. In *Regulation of Matrix accumulation*, Mecham, R. P. (Eds), Academic Press, NY, USA 1986, 217-306). HNE has long been considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure both small molecule inhibitors and protein inhibitors of HNE inhibit the inflammatory response and the development of emphysema (Wright, J. L. et al. *Am. J. Respir. Crit. Care Med.* 2002, 166, 954-960; Churg, A. et al. *Am. J. Respir. Crit. Care Med.* 2003, 168, 199-207). Thus, HNE may play a role both in matrix destruction and in amplifying inflammatory responses in chronic respiratory diseases where neutrophil influx is a characteristic feature. Indeed, HNE is believed to play a role in several pulmonary diseases, including chronic obstructive pulmonary disease (COPD), cystic fibrosis (CF), acute respiratory distress syndrome (ARDS), pulmonary emphysema, pneumonia and lung fibrosis. It is also implicated in several cardiovascular diseases in which tissue remodelling is involved, for example, in heart failure and the generation of ischaemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (Thompson, A. B.; Daughton, D.; et al. *Am. Rev. Respir. Dis.* 1989, 140, 1527-1537). The major pathogenic determinant in COPD has long been considered to be the protease-anti-protease balance (also known as the 'elastase:anti-elastase hypothesis'), in which an imbalance of HNE and endogenous antiproteases such as α1-antitrypsin ($\alpha_1$-AT), Secretory leukocyte protease inhibitor (SLPI) and pre-elafin leads to the various inflammatory disorders of COPD. Individuals that have a genetic deficiency of the protease inhibitor α1-antitrypsin develop emphysema that increases in severity over time (Laurrell, C. B.; Erikkson, S *Scand. J. Clin. Invest.* 1963 15, 132-140). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Multimeric ligands consist of multiple binding domains which are tethered together through a suitable scaffold. Hence individual binding domains are linked together into a single molecule, increasing the probability that the multimer will bind sequentially in a step-wise manner with multiple active sites resulting in high-affinity interactions (Handl, H. L. et al. *Expert Opin. Ther. Targets* 2004, 8, 565-586; Han, Y. F. et al., *Bioorg. Med. Chem. Letts.* 1999, 7, 2569-2575). Also, multiple binding interactions (either sequential or parallel) with relatively high off-rates can combine to yield an overall low off-rate for the multimeric ligand. Thus, a molecule consisting of a suitable linker and ligands may be expected to show advantage over the monomeric ligands alone in terms of potency and/or duration of action. Multimeric compounds are unlikely to be orally bioavailable (as predicted by Lipinski's "Rule of 5") which may be advantageous where an inhaled route of administration to the lungs is targeted, since even after inhaled administration, a large proportion of drug is likely to enter the GI tract. Thus such compounds may be expected to show reduced systemic exposure after inhalation administration and hence an improved toxicity profile over orally administered therapies.

BRIEF DESCRIPTION OF THE INVENTION

This invention provides novel compounds which are inhibitors of HNE, and are useful in the treatment of diseases or conditions in which HNE activity plays a part. The compounds of the invention may be used as monomers or, particularly in the case of topical pulmonary application by inhalation, in the form of multimers, such as dimers, covalently linked via a linker framework.

DETAILED DESCRIPTION OF THE INVENTION

In one embodiment, the invention provides a compound of formula (I):

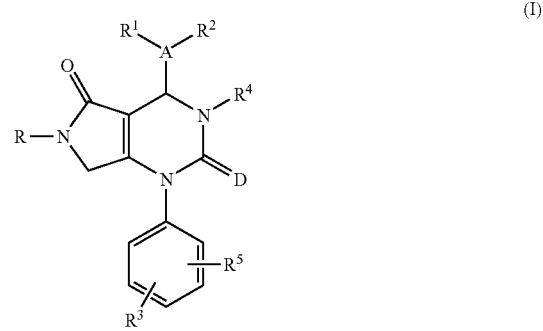

wherein
A is aryl or heteroaryl;
D is oxygen or sulphur;
$R^1$, $R^2$, $R^3$ and $R^5$ are independently each hydrogen, halogen, nitro, cyano, $C_1$-$C_6$-alkyl, $C_2$-$C_6$-alkenyl, $C_2$-$C_6$-alkynyl, hydroxy or $C_1$-$C_6$-alkoxy or $C_2$-$C_6$-alkenyloxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy;
R and $R^4$ each independently represent a radical of formula —[X]$_m$-[Alk$^1$]$_p$-[Q]$_n$-[Alk$^2$]$_q$—[X$^1$]$_k$-Z wherein
k, m, n, p and q are independently 0 or 1;
Alk$^1$ and Alk$^2$ each independently represent an optionally substituted $C_1$-$C_6$ alkylene, or $C_2$-$C_6$ alkenylene radical which may optionally contain an ether (—O—), thioether (—S—) or amino (—NR$^A$—) link wherein $R^A$ is hydrogen or $C_1$-$C_3$ alkyl;
Q represents (i) —O—, —S—, —S(=O)—, —S(=O)$_2$—, —S$^+$(R$^A$)—, —N(R$^A$)—, —N$^+$(R$^A$)(R$^B$)—, —C(=O)—, —C(=O)O—, —OC(=O)—, —C(=O)NR$^A$—, —NR$^A$C(=O)—, —S(O$_2$)NR$^A$—, —NR$^A$S(O$_2$)—, NR$^A$C(=O)NR$^B$—, NR$^A$C(=NR$^A$)NR$^B$—, —C(=NR$^D$)NR$^E$, —NR$^E$C(=NR$^D$), wherein $R^A$, $R^B$, $R^D$ and $R^E$ are independently hydrogen, $C_1$-$C_6$ alkyl, or $C_3$-$C_6$ cycloalkyl, or $R^A$ and $R^B$ or $R^D$ and $R^E$ taken together with the nitrogen to which they are attached form a monocyclic heterocyclic ring of 5 to 7 ring atoms which my contain a further heteroatom selected from N, O and S, or (ii) an optionally substituted divalent mono- or bicyclic carbocyclic or heterocyclic radical having 3-6 ring members;
X represents —(C=O)—, —S(O$_2$)—, —C(=O)O—, —(C=O)NR$^A$—, or —S(O$_2$)NR$^A$—, wherein $R^A$ is hydrogen, $C_1$-$C_6$ alkyl, or $C_3$-$C_6$ cycloalkyl;
$X^1$ represents —O—, —S—, or —NH; and
Z is hydrogen or an optionally substituted mono- or bicyclic carbocyclic or heterocyclic radical having 3-6 ring members.

The invention also includes a multimeric compound comprising two, three or four molecules of a compound of formula (I) above, covalently linked through a linker framework.

Compounds of formula (I) above and multimers thereof may be prepared in the form of salts, particularly pharmaceutically acceptable salts, N-oxides, hydrates and solvates thereof. Any claim to a compound herein, or reference to "compounds of the invention", compounds with which the invention is concerned", compounds of formula (I), and the like includes salts, N-oxides, hydrates and solvates of such compounds.

Compounds of the invention may be useful in the treatment or prevention of diseases in which HNE is implicated, for example chronic obstructive pulmonary disease (COPD), chronic bronchitis, lung fibrosis, pneumonia, acute respiratory distress syndrome (ARDS), pulmonary emphysema, smoking-induced emphysema and cystic fibrosis.

Hence other aspects of the invention are (i) a pharmaceutical composition comprising a compound of the invention and a pharmaceutically acceptable carrier or excipient; and (ii) the use of a compound of the invention for the manufacture of a medicament for the treatment or prevention of a disease or condition in which HNE is implicated.

Terminology

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, iso-propyl, n-butyl, isobutyl, sec-butyl, t-butyl, n-pentyl and n-hexyl.

As used herein the term "($C_a$-$C_b$)alkenyl" wherein a and b are integers refers to a straight or branched chain alkenyl moiety having from a to b carbon atoms having at least one double bond of either E or Z stereochemistry where applicable. Thus when a is 2 and b is 6, for example, the term includes, for example, vinyl, allyl, 1- and 2-butenyl and 2-methyl-2-propenyl.

As used herein the term "$C_a$-$C_b$ alkynyl" wherein a and b are integers refers to straight chain or branched chain hydrocarbon groups having from a to b carbon atoms and having in addition one triple bond. Thus when a is 1 and b is 6, for example, the term includes for example, ethynyl (—C≡CH), 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_a$-$C_b$)alkylene radical" wherein a and b are integers refers to a saturated hydrocarbon chain having from a to b carbon atoms and two unsatisfied valences.

As used herein the term "divalent ($C_a$-$C_b$)alkenylene radical" wherein a and b are integers refers to a divalent hydrocarbon chain having from 2 to 6 carbon atoms, and at least one double bond.

As used herein the unqualified term "carbocyclic" refers to a mono-, bi- or tricyclic radical having up to 16 ring atoms, all of which are carbon, and includes aryl and cycloalkyl.

As used herein the unqualified term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" or "heterocycloalkyl" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, ($C_1$-$C_6$) alkyl, cycloalkyl, ($C_1$-$C_6$)alkoxy, hydroxy, hydroxy($C_1$-$C_6$)

alkyl, mercapto, mercapto($C_1$-$C_6$)alkyl, ($C_1$-$C_6$)alkylthio, phenyl, monocyclic heteroaryl having 5 or 6 ring atoms, halo (including fluoro, bromo and chloro), trifluoromethyl, trifluoromethoxy, nitro, nitrile (—CN), oxo, —COOH, —COOR$^A$, COR$^A$, $SO_2R^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are independently a ($C_1$-$C_6$)alkyl, ($C_3$-$C_6$) cycloalkyl, phenyl or monocyclic heteroaryl having 5 or 6 ring atoms, or R$^A$ and R$^B$ when attached to the same nitrogen atom form a cyclic amino ring, such as piperidinyl, morpholinyl or piperazinyl. An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like. Those compounds (I) which have a basic nitrogen can also form quaternary ammonium salts with a pharmaceutically acceptable counter-ion such as chloride, bromide, acetate, formate, p-toluenesulfonate, succinate, hemi-succinate, naphthalene-bis sulfonate, methanesulfonate, xinafoate, and the like.

Compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

In the monomeric compounds of the invention of formula (I), in any compatible combination:

The atom D may be O or S, O is currently preferred.

The ring A is aryl or heteroaryl and may be any of those rings listed above as examples of aryl or heteroaryl, especially phenyl and monocyclic heteroaryl having 5 or 6 ring atoms. Specific examples include pyridyl, such as 2- and 3-pyridyl, or pyrimidinyl such as pyrimidin-2-yl, but presently it is preferred that A be phenyl.

$R^1$ and $R^2$ may be selected from any of the substituent types for which they are defined in relation to formula (I), including hydrogen, halogen, nitro, cyano, $C_1$-$C_3$-alkyl, $C_2$-$C_3$-alkenyl, $C_2$-$C_3$-alkynyl, hydroxy or $C_1$-$C_3$-alkoxy or $C_2$-$C_3$-alkenyloxy. Specific examples of such substitutents include hydrogen, fluoro, chloro, bromo, cyano, methyl, methoxy and —C≡CH. For example, —AR$^1$R$^2$ may be 4-cyanophenyl or 4-ethynylphenyl.

$R^3$ and $R^5$ too may be selected from any of the substituent types for which they are defined in relation to formula (I), but in one currently preferred type of compound of the invention $R^3$ and $R^5$ are independently H, CF$_3$, F, Cl or Br. The preferred position of substitution on the phenyl ring by $R^3$ and/or $R^5$ is 3-, 4- or 5-.

Presently it is believed that the monomers of the invention can interact with HNE as inhibitors with the R or $R^4$ substituent located remote from the binding interface, extending towards solvent. Hence those groups provide sites for modulation of solubility and other pharmacokinetic properties. Accordingly R and $R^4$ may vary widely, and are defined in relation to formula (I) as a radical of formula —[X]$_m$-[Alk$^1$]$_p$-[Q]$_n$-[Alk$^2$]$_q$-[X$^1$]$_k$-Z. According to that definition, k, m, n, p and q may all be 0, and Z may be hydrogen, so that R or $R^4$ itself may be hydrogen. However, many other classes of R or $R^4$ substituent are encompassed by selecting different combinations of values for the variables.

For example R or $R^4$ may be selected from $C_1$-$C_6$-alkyl, formyl, aminocarbonyl, mono- or di-$C_1$-$C_4$-alkylaminocarbonyl, $C_3$-$C_8$-cycloalkylcarbonyl, $C_1$-$C_6$-alkylcarbonyl, $C_1$-$C_6$-alkoxycarbonyl, N—($C_1$-$C_4$-alkylsulfonyl)-aminocarbonyl, N—($C_1$-$C_4$-alkylsulfonyl)-N—($C_1$-$C_4$-alkyl)-aminocarbonyl, heteroaryl, heterocycloalkyl, heteroarylcarbonyl or heterocycloalkylcarbonyl; wherein $C_1$-$C_6$-alkyl, mono- and di-$C_1$-$C_4$-alkylaminocarbonyl, $C_1$-$C_6$-alkylcarbonyl, $C_1$-$C_6$-alkoxycarbonyl, heteroaryl and heterocycloalkyl can be substituted with one to three identical or different radicals selected from the group consisting of aryl, heteroaryl, hydroxyl, $C_1$-$C_4$-alkoxy, hydroxycarbonyl, $C_1$-$C_6$-alkoxycarbonyl, aminocarbonyl, mono and di-$C_1$-$C_4$-alkylaminocarbonyl, amino, mono- and di-$C_1$-$C_4$-alkylamino, $C_1$-$C_4$-alkylcarbonylamino, cyano, N-(mono- and di-$C_1$-$C_4$-alkylamino-$C_1$-$C_4$-alkyl)-aminocarbonyl, N—($C_1$-$C_4$-alkoxy-$C_1$-$C_4$-alkyl)-aminocarbonyl and halogen.

In a particular subclass of compounds of the invention, $R^4$ and/or R is radical of formula —[X]$_m$-[Alk$^1$]$_p$-[Q]$_n$-[Alk$^2$]$_q$-[X$^1$]$_k$-Z wherein m is 0, and k, p, n and q are each 1, Q is —N(R$^A$) or —N$^+$(R$^A$)(R$^B$)—, and R$^A$, R$^B$Alk$^1$, Alk$^2$, X$_1$ and Z are as defined in relation to formula (I). In this subclass, X$^1$ may be, for example, —O—, and Z may be, for example optionally substituted phenyl or monocyclic heteroaryl, the latter having 5 or 6 ring atoms.

In the compounds of the invention one of R and $R^4$ may be hydrogen, while the other is a substituent other than hydrogen Other types of R and $R^4$ groups have Formula (VIIIA), (VIIIB) or (VIIIC):

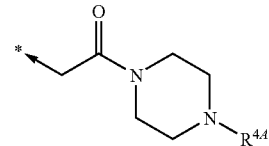

(VIIIA)

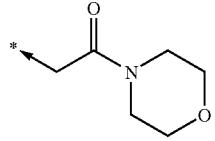

(VIIIB)

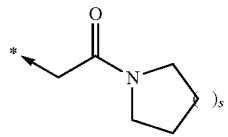

(VIIIC)

wherein
$R^{4A}$ is hydrogen or $C_1$-$C_6$-alkyl, and s is 1 or 2.

Further types of R and $R^4$ groups have Formula (IX)

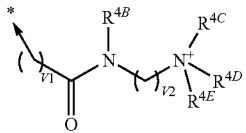

(IX)

wherein
$R^{4B}$ is hydrogen or $C_1$-$C_6$-alkyl;
$R^{4C}$, $R^{4D}$, $R^{4E}$ are each $C_1$-$C_6$-alkyl, and the nitrogen to which they are attached is quaternary and carries a positive charge; and additionally any two of $R^{4C}$, $R^{4D}$, $R^{4E}$ may be joined to form a ring, optionally containing a second heteroatom selected from oxygen or nitrogen;
or
One of $R^{4C}$, $R^{4D}$, $R^{4E}$ is a lone pair and the other groups are as defined above, and the nitrogen to which they are attached is tertiary; and
v1 and v2 are each independently 0-5.

Other types of R and $R^4$ groups are those selected from the following:

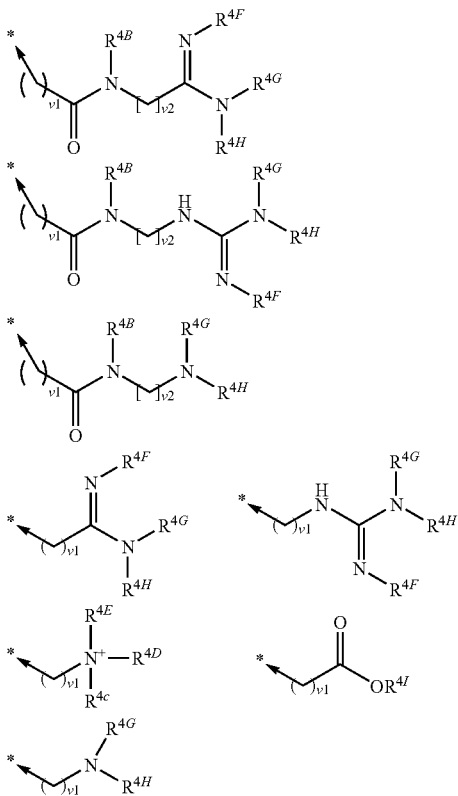

wherein
$R^{4B}$ is hydrogen or $C_1$-$C_6$-alkyl;
$R^{4C}$, $R^{4D}$, $R^{4E}$ are each $C_1$-$C_6$-alkyl, and the nitrogen to which they are attached is quaternary and carries a positive charge; and additionally any two of $R^{4C}$, $R^{4D}$, $R^{4E}$ may be joined to form a ring, optionally containing a second heteroatom selected from oxygen or nitrogen;
or
one of $R^{4C}$, $R^{4D}$, $R^{4E}$ is a lone pair and the other groups are as defined above, and the nitrogen to which they are attached is tertiary;
$R^{4F}$ and $R^{4I}$ are independently hydrogen or $C_1$-$C_6$-alkyl;
$R^{4G}$ and $R^{4H}$ are independently hydrogen or $C_1$-$C_6$-alkyl, or $R^{4G}$ and $R^{4H}$ taken together with the nitrogen to which they are attached form a monocyclic heterocyclic ring of 5 to 7 ring atoms which my contain a further heteroatom selected from N, O and S; and
v1 and v2 are each independently 0-5.

In the multimeric compounds of the invention, two, three or four molecules of a monomeric compound of the invention are covalently linked through a linker framework. Since the linker framework need not play an active role in interacting with the HNE enzyme, its role is simply to allow binding contact between one or more of the monomeric elements and the enzyme. Hence a vast range of chemistries may be envisaged for the linker framework. Furthermore, the point of attachment of the monomeric elements to the linker framework may be selected according to the particular linker chemistry to be employed. Presently it is preferred that two, three or four of the monomeric molecules are linked to the linker framework via their respective nitrogen atoms shown in formula (I) as linked to R or $R^4$.

Furthermore, it is presently preferred that only two of the monomers are so linked. In the latter case, the linker framework may be, for example, the linker framework may be a divalent straight chain, saturated or unsaturated hydrocarbon radical having from 2 to 12 carbon atoms in the said chain, and wherein one or more carbons may be replaced by a divalent monocyclic or bicyclic carbocyclic or heterocyclic radical having from 3 to 7 ring atoms in the or each ring, or by —O—, —S—, —S(=O)—, —S(=O)$_2$—, —C(=O)—, —N($R^P$)—, —N$^+$($R^P$)($R^Q$)—, —C(=O)O—, —OC(=O)—, —C(=O)N$R^A$—, —N$R^A$C(=O)—, —S(O$_2$)N$R^A$—, —N$R^A$S(O$_2$)—, —N$R^A$C(=O)N$R^B$—, —N$R^A$C(=N$R^A$)N$R^B$—, —C(=N$R^D$)N$R^E$—, or —N$R^E$C(=N$R^D$)—, wherein $R^A$, $R^B$, $R^D$ and $R^E$ are independently hydrogen, $C_1$-$C_6$ alkyl, or $C_3$-$C_6$ cycloalkyl, and $R^P$ and $R^Q$ are independently hydrogen, $C_1$-$C_6$ alkyl, or $C_3$-$C_6$ cycloalkyl, HO—($C_1$-$C_6$ alkyl)-, $R^A R^B$N—($C_1$-$C_6$ alkyl)-, or HOC(=O)—($C_1$-$C_6$ alkyl)-, or $R^A$ and $R^B$, or $R^D$ and $R^E$, or $R^P$ and $R^Q$ taken together with the nitrogens to which they are attached form a monocyclic heterocyclic ring of 5 to 7 ring atoms which may contain a further heteroatom selected from N, O and S.

When one or more one or more —(CH$_2$)— groups of the linker framework is or are replaced by a divalent monocyclic or bicyclic carbocyclic or heterocyclic radical, the said radical may be selected from, for example, the following:

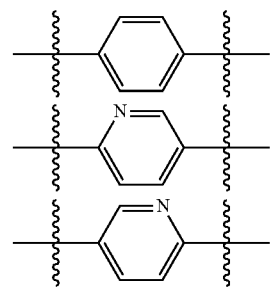

-continued

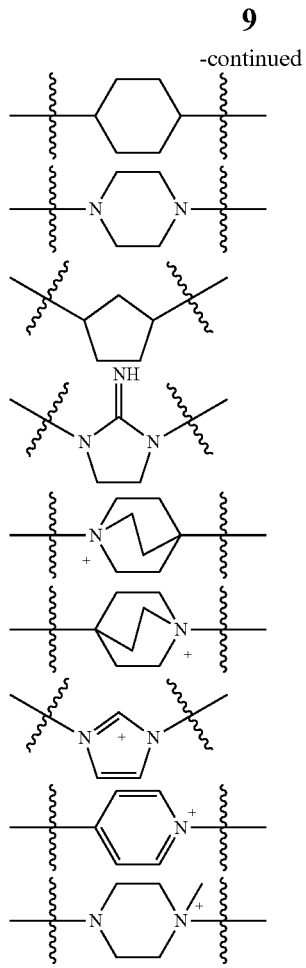

The linker framework may have, for example, one of the following structures (A), (B), (C), (D), (E), (G) and (E):

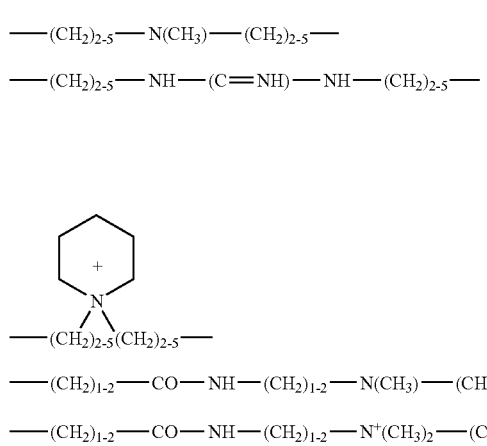

Specific linker frameworks of the above type include those present in the dimer compounds of the examples herein.

Thus, one preferred subset of the multimers of the invention has the formula M-L-M¹ wherein L is a divalent linker radical, for example of the kinds discussed above as linker frameworks, and M and M¹ are each independently a radical of formula (IA) wherein D, A and R¹-R⁵ are as defined and discussed above:

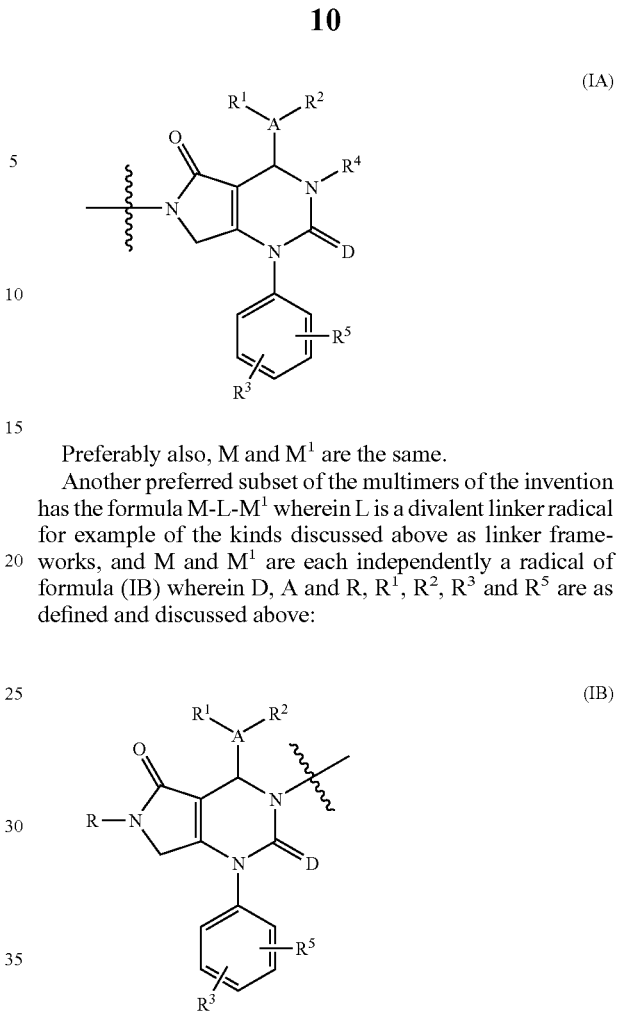

Preferably also, M and M¹ are the same.

Another preferred subset of the multimers of the invention has the formula M-L-M¹ wherein L is a divalent linker radical for example of the kinds discussed above as linker frameworks, and M and M¹ are each independently a radical of formula (IB) wherein D, A and R, R¹, R², R³ and R⁵ are as defined and discussed above:

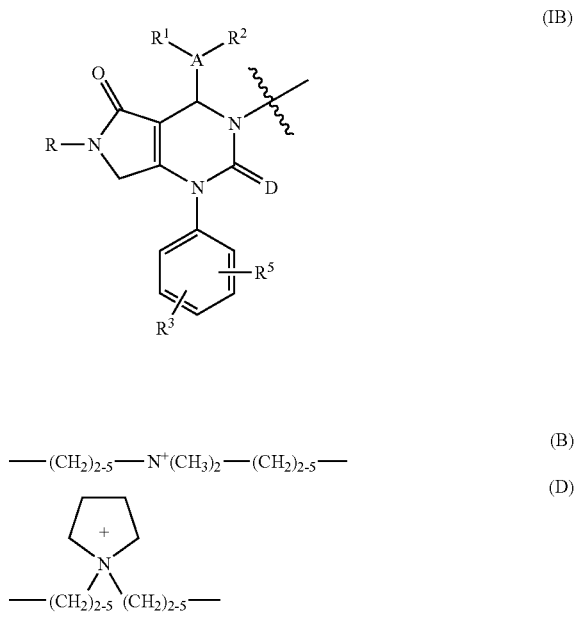

Here too, it is currently preferred that M and M¹ are the same.

Specific examples of such dimeric compounds of formula (IA) and (IB) include those of the Examples herein.

The therapeutic utility of the present compounds is pertinent to any disease that is known to be at least partially mediated by the action of human neutrophil elastase. For example, the present compounds may be beneficial in the treatment of chronic obstructive pulmonary disease (COPD), cystic fibrosis (CF), acute respiratory distress syndrome (ARDS), pulmonary emphysema, pneumonia and lung fibrosis.

The present invention is also concerned with pharmaceutical formulations comprising, as an active ingredient, a compound of the invention. Other compounds may be combined with compounds of this invention for the prevention and treatment of inflammatory diseases of the lung. Thus the present invention is also concerned with pharmaceutical compositions for preventing and treating inflammatory diseases of the lung comprising a therapeutically effective amount of a compound of the invention and one or more other therapeutic agents.

Suitable therapeutic agents for a combination therapy with compounds of the invention include: (1) a corticosteroid, for example fluticasone or budesonide; (2) a β2-adrenoreceptor agonist, for example salmeterol or formeterol; (3) a leukotriene modulator, for example montelukast or pranlukast; (4) anticholinergic agents, for example selective muscarinic-3 (M3) receptor antagonists such as tiotropium bromide; (5) phosphodiesterase-IV (PDE-IV) inhibitors, for example roflumilast or cilomilast; (6) an antitussive agent, such as codeine or dextramorphan; and (7) a non-steroidal anti-inflammatory agent (NSAID), for example ibuprofen or ketoprofen.

The weight ratio of the first and second active ingredients may be varied and will depend upon the effective dose of each ingredient. Generally, an effective dose of each will be used.

The magnitude of prophylactic or therapeutic dose of a compound of the invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

Another aspect of the present invention provides pharmaceutical compositions which comprise a compound of the invention and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the invention, additional active ingredient(s), and pharmaceutically acceptable excipients.

The pharmaceutical compositions of the present invention comprise a compound of the invention as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Any suitable route of administration may be employed for providing a mammal, especially a human, with an effective dosage of a compound of the present invention. In therapeutic use, the active compound may be administered by any convenient, suitable or effective route. Suitable routes of administration are known to those skilled in the art, and include oral, intravenous, rectal, parenteral, topical, ocular, nasal, buccal and pulmonary. Delivery by inhalation is preferred.

Compositions suitable for administration by inhalation are known, and may include carriers and/or diluents that are known for use in such compositions. The composition may contain 0.01-99% by weight of active compound. Preferably, a unit dose comprises the active compound in an amount of 1 µg to 10 mg.

The most suitable dosage level may be determined by any suitable method known to one skilled in the art. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease undergoing treatment.

For delivery by inhalation, the active compound is preferably in the form of microparticles. They may be prepared by a variety of techniques, including spray-drying, freeze-drying and micronisation.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 (CCl2F2) and HFA-152 (CH4F2 and isobutane).

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 µm.

In the case of an aerosol-based formulation, a preferred composition is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

Compounds of the invention may be used in combination with other drugs that are used in the treatment/prevention/suppression or amelioration of the diseases or conditions for which present compounds are useful. Such other drugs may be administered, by a route and in an amount commonly used therefore, contemporaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the present invention include those that also contain one or more other active ingredients, in addition to a compound of the invention.

The agents of the invention may be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321).

Methods of Synthesis

The compounds of the present invention can be prepared according to the procedures of the following schemes and examples, using appropriate materials, and are further exemplified by the following specific examples. Moreover, by utilising the procedures described with the disclosure contained herein, one of ordinary skill in the art can readily prepare additional compounds of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein above. The free acid or base form corresponding to isolated salts can be generated by neutralisation with a suitable base or acid such as sodium hydroxide, potassium carbonate, acetic acid and hydrochloric acid and extraction of the liberated free acid or base into an organic solvent followed by evaporation. The free form isolated in this manner can be further converted into another pharmaceutically acceptable salt by dissolution in an organic solvent followed by addition of the appropriate acid or base and subsequent evaporation, precipitation, or crystallisation.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, 1999, may be used.

Compounds of the invention may be prepared according to the routes illustrated in Schemes 1 and 2.

Scheme 1

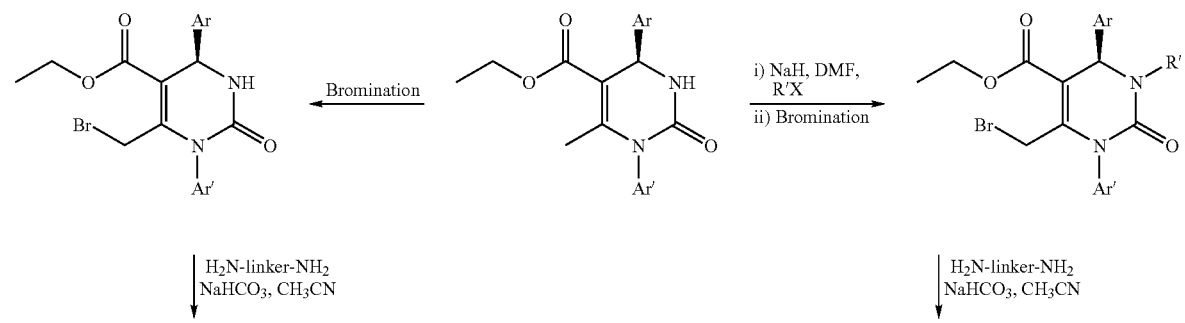

15
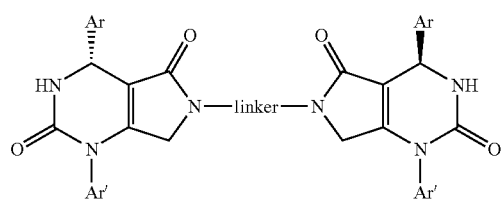
16
-continued
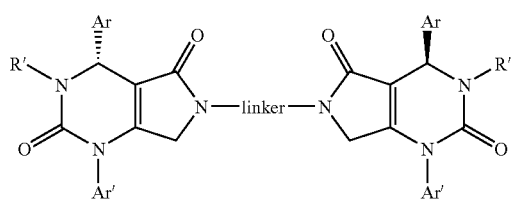
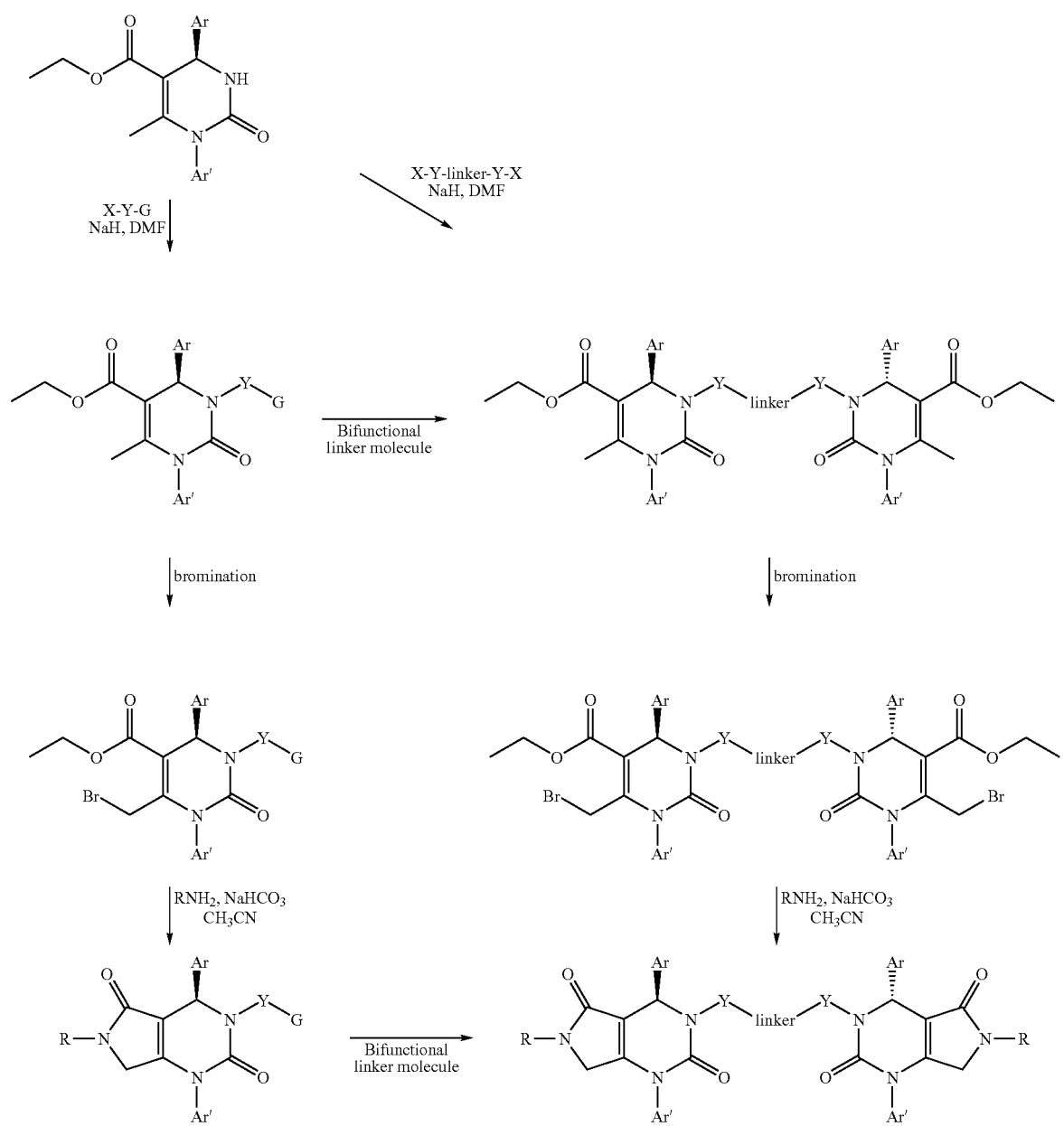
Scheme 2
X = leaving group e.g. Br
Y = spacer eg (CH$_2$)$_n$
G = reactive group e.g. CO$_2$H Scheme 3

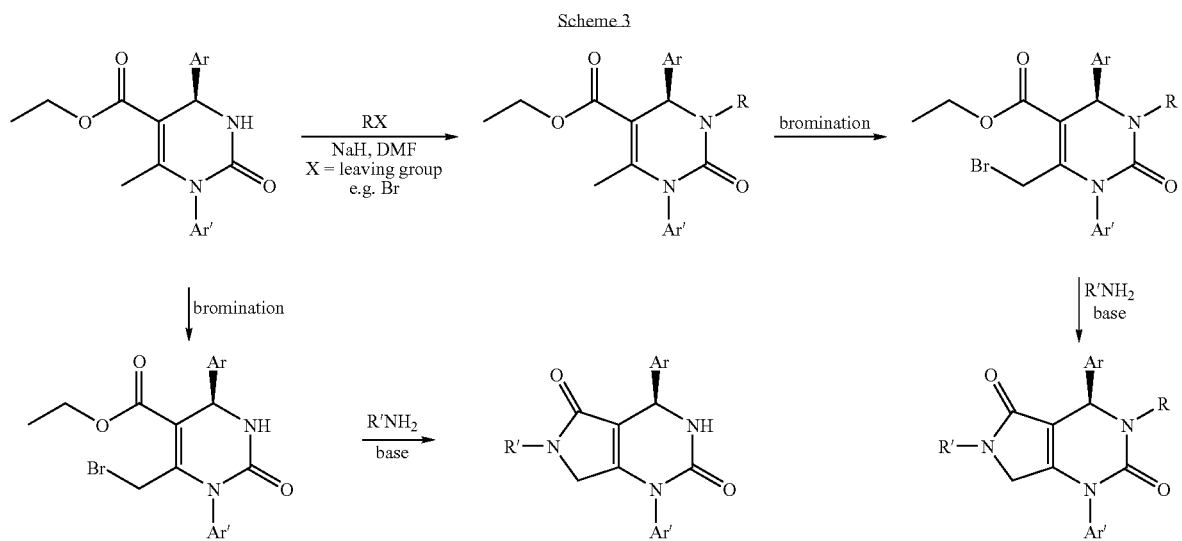

The following Examples illustrate the invention.

General Experimental Details:

All solvents and commercial reagents were used as received. Where products were purified using an Isolute™ SPE Si II cartridge, 'Isolute SPE Si cartridge' refers to a pre-packed polypropylene column containing unbonded activated silica with irregular particles with average size of 50 μm and nominal 60 Å porosity. Where an Isolute™ SCX-2 cartridge was used, 'Isolute SCX-2 cartridge' refers to a pre-packed polypropylene column containing a non end-capped propylsulphonic acid functionalised silica strong cation exchange sorbent. 'Isolute Al—N cartridge' refers to a pre-packed polypropylene column containing neutral alumina with average particle size 50-200 μm and 120 Å pore diameter.

Preparative HPLC Conditions:

HPLC System 1:

C18-reverse-phase column (100×22.5 mm i.d Genesis column with 7 μm particle size), eluting with a gradient of A: water+0.1% formic acid; B: acetonitrile+0.1% formic acid at a flow rate of 5 ml/min and gradient of 1%/min increasing in B. UV detection at 230 nm. Compounds were obtained as the formate salt where stated.

HPLC System 2:

C18-reverse-phase end-capped column (250×21.2 mm Gemini column with 5 μm particle size), eluting with a gradient of A: water+0.1% formic acid; B: acetonitrile+0.1% formic acid with a flow rate typically 17 ml/min and gradient of 1%/min increasing in B. UV detection at 254 nm. Compounds were obtained as the formate salt where stated.

HPLC System 3:

C18-reverse-phase end-capped column (250×21.2 mm Gemini column with 5 μm particle size), eluting with a gradient of A: water; B: acetonitrile with a flow rate typically 17 ml/min and gradient of 1%/min increasing in B. UV detection at 254 nm.

HPLC System 4:

C18-reverse-phase end-capped column (250×21.2 mm Gemini column with 5 μm particle size), eluting with a gradient of A: water; B: MeOH with a flow rate typically 17 ml/min and gradient of 1%/min increasing in B. UV detection at 254 nm.

HPLC System 5:

C18-reverse-phase column (250×21.2 mm Luna column with 5 μm particle size), eluting with a gradient of A: water+0.1% formic acid; B: acetonitrile+0.1% formic at a flow rate of 15 ml/min and gradient of 1%/min increasing in B. UV detection at 254 nm. Compounds were obtained as the formate salt where stated.

LC-MS Method 1:

Waters Platform LC with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow ml/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (100 μl split to MS with in-line UV detector)
MS ionisation method - Electrospray (positive and negative ion)

LC-MS Method 2:

Waters Micromass ZMD with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow ml/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (100 μl split to MS with in-line UV detector)
MS ionisation method - Electrospray (positive and negative ion)

LC-MS Method 3:

Micromass Platform LCT with a C18-reverse-phase column (100×3.0 mm Higgins Clipeus with 5 μm particle size), elution with A: water+0.1% formic acid; B: acetonitrile+0.1% formic acid. Gradient:

| Gradient - Time | flow ml/min | % A | % B |
|---|---|---|---|
| 0.00 | 1.0 | 95 | 5 |
| 1.00 | 1.0 | 95 | 5 |
| 15.00 | 1.0 | 5 | 95 |
| 20.00 | 1.0 | 5 | 95 |
| 22.00 | 1.0 | 95 | 5 |
| 25.00 | 1.0 | 95 | 5 |

Detection - MS, ELS, UV (100 μl split to MS with in-line UV detector)
MS ionisation method - Electrospray (positive ion)

LC-MS Method 4:

Waters Micromass ZQ2000 with a C18-reverse-phase column (100×3.0 mm HIggins Clipeus with 5 μm particle size), elution with A: water+0.1% formic acid; B: acetonitrile+0.1% formic acid. Gradient:

| Gradient - Time | flow ml/min | % A | % B |
|---|---|---|---|
| 0.00 | 1.0 | 95 | 5 |
| 1.00 | 1.0 | 95 | 5 |
| 15.00 | 1.0 | 5 | 95 |
| 20.00 | 1.0 | 5 | 95 |
| 22.00 | 1.0 | 95 | 5 |
| 25.00 | 1.0 | 95 | 5 |

Detection - MS, ELS, UV (100 μl split to MS with in-line UV detector)
MS ionisation method - Electrospray (positive ion)

LC-MS Method 5:

Waters Platform LC quadrupole mass spectrometer linked to a Hewlett Packard HP1100 LC system with a C18 reverse-phase column (30×4.6 mm Phenomenex Luna with 3 μm particle size), elution with A: water+0.1% formic acid; B: acetonitrile+0.1% formic acid. Gradient as for method 1.

LC-MS Method 6:

Waters Micromass ZQ2000 linked to a Hewlett Packard HP1100 LC system with a C18-reverse-phase column (100×3.0 mm Higgins Clipeus with 5 μm particle size), elution with A: water+0.1% formic acid; B: acetonitrile+0.1% formic acid.

Gradient as for Method 3.

Abbreviations used in the experimental section:

DCM=dichloromethane
DMF=N,N-dimethylformamide
HPLC=high performance liquid chromatography
IMS=industrial methylated spirits
RT=room temperature
Rt=retention time
THF=tetrahydrofuran
TFA=trifluoroacetic acid The following intermediates can be prepared according to the reference given:

| Intermediate | Structure | Reference |
|---|---|---|
| 1 | 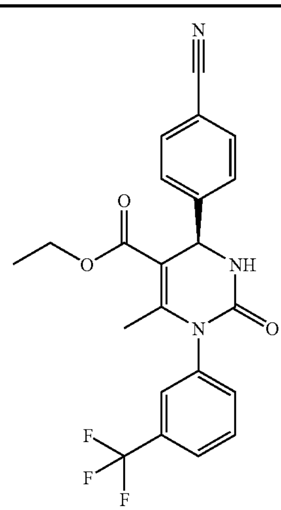 | WO2006/082412 |

-continued

| Intermediate | Structure | Reference |
|---|---|---|
| 2 | 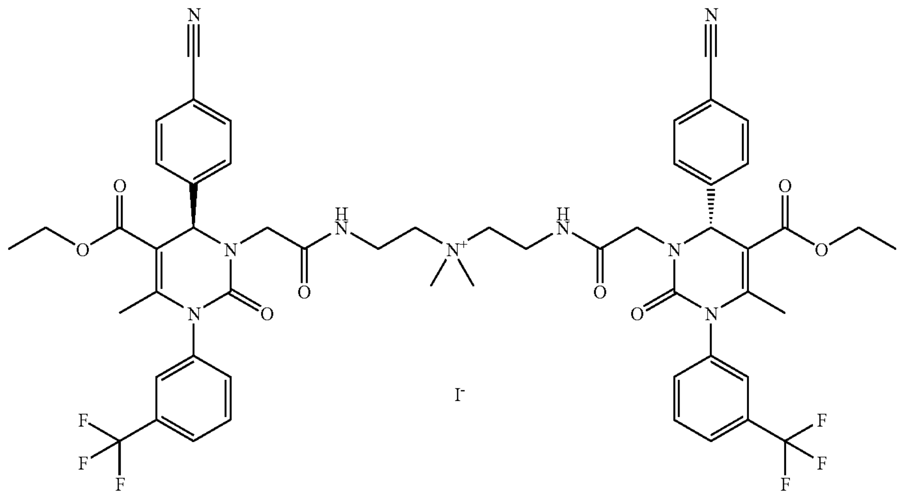 | WO2006/082412 |
| 3 | 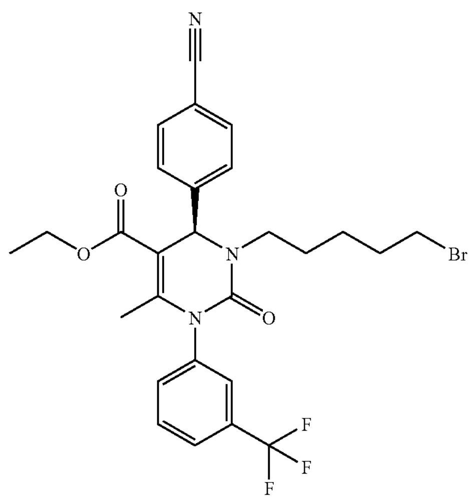 | WO2006/082412 |
| 4 | 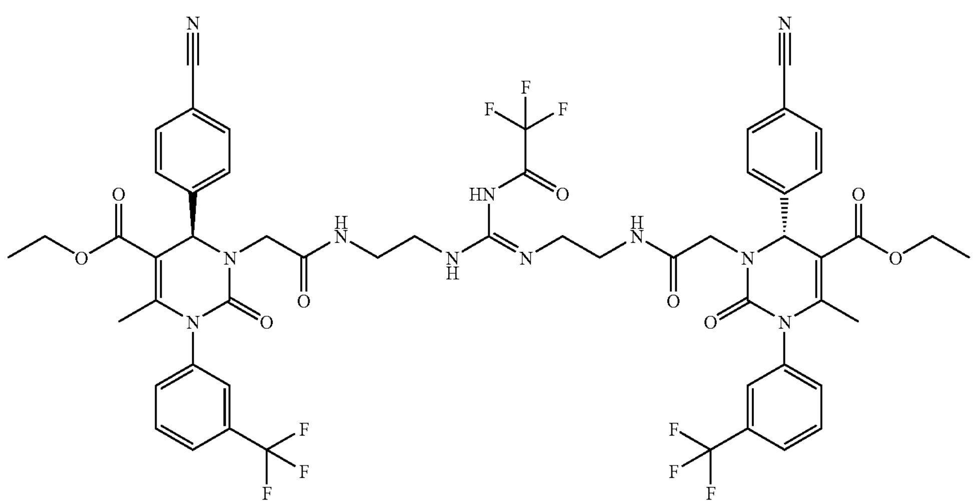 | WO2006/082412 |

-continued

| Intermediate | Structure | Reference |
|---|---|---|
| 5 | 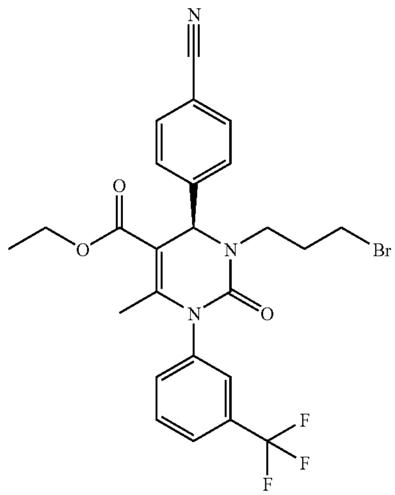 | WO2006/082412 |
| 6 | 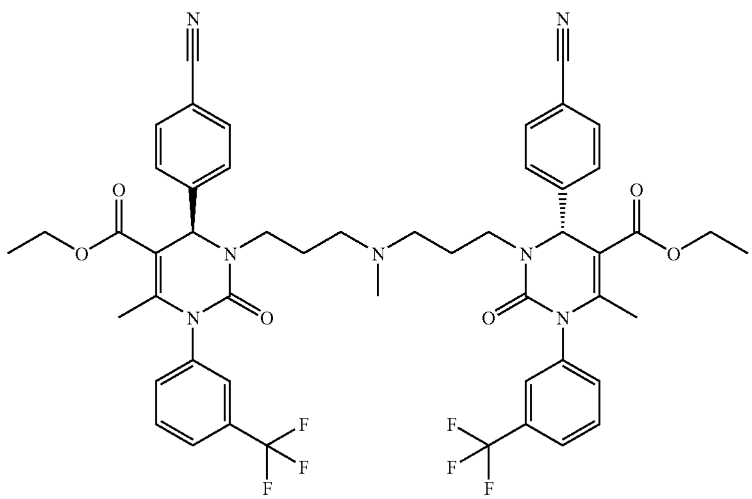 | WO2006/082412 |
| 7 | 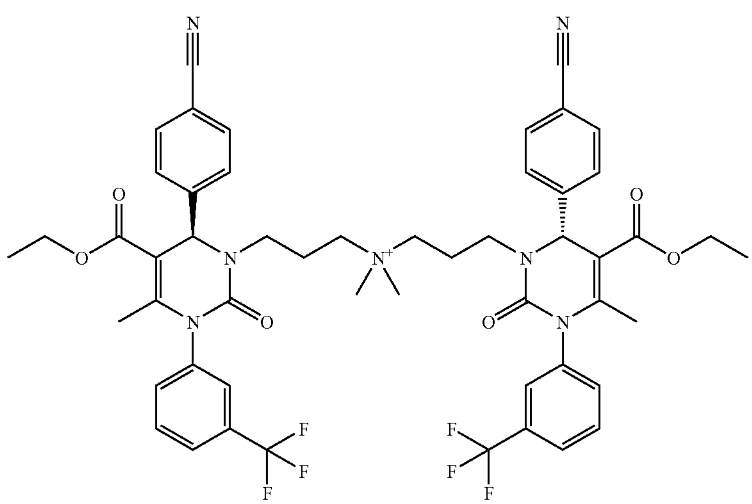 | WO2006/082412 |

-continued

| Intermediate | Structure | Reference |
|---|---|---|
| 8 | ethyl 4-(4-cyanophenyl)-1-(3-chlorophenyl)-6-methyl-2-oxo-1,2,3,4-tetrahydropyrimidine-5-carboxylate | WO2004/024700 |
| 9 | ethyl 4-(6-cyanopyridin-3-yl)-6-methyl-2-oxo-1-(3-(trifluoromethyl)phenyl)-1,2,3,4-tetrahydropyrimidine-5-carboxylate | WO2004/024700 |
| 10 | ethyl 4-(4-cyanophenyl)-6-methyl-1-(3-methylphenyl)-2-oxo-1,2,3,4-tetrahydropyrimidine-5-carboxylate | WO2004/024700 |

| Intermediate | Structure | Reference |
|---|---|---|
| 11 | 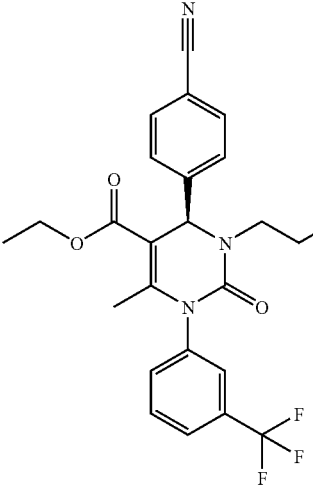 | WO2006/082412 |
| 12 | 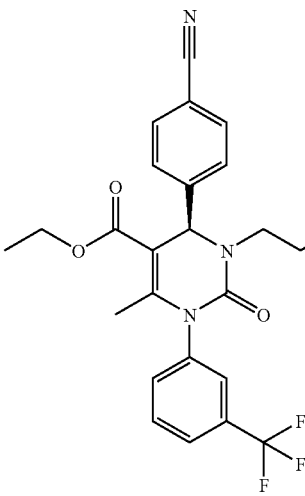 | WO2006/082412 |

| Intermediate | Structure | Reference |
|---|---|---|
| 13 | 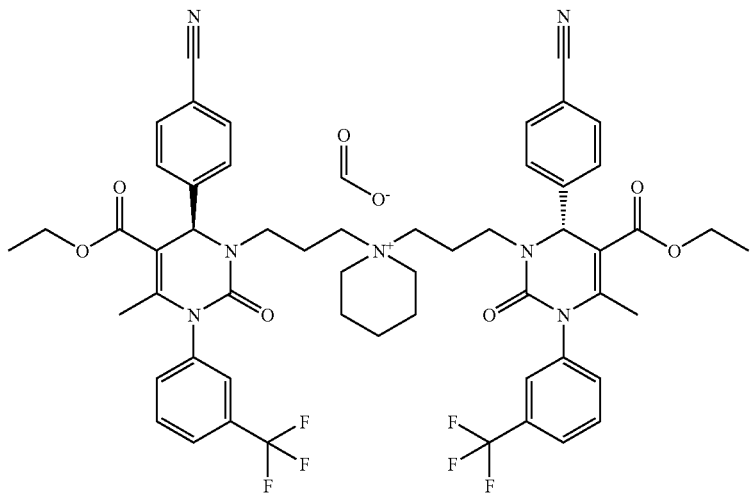 | WO2006/082412 |

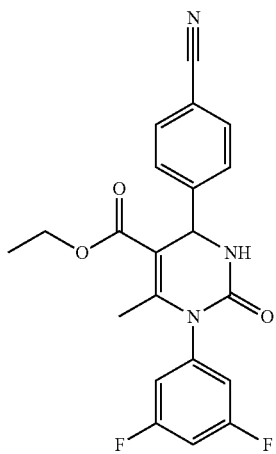

Intermediate 14

Polyphosphoric acid (17.2 g) was suspended in THF (90 ml) and stirred mechanically whilst 3,5-difluorophenylurea (5.40 g, 31.4 mmol), 4-cyanobenzaldehyde (4.94 g, 37.6 mmol) and ethyl acetoacetate (3.97 ml, 31.4 mmol) were added. The resulting mixture was heated at reflux for 17 h, and then left at room temperature for 48 h. The solvent was removed under reduced pressure and the residue partitioned between water and EtOAc. The organic layer was washed with water, aqueous sodium carbonate solution, water then brine and dried (MgSO$_4$), filtered and concentrated. The resulting foam was purified in two batches on a Biotage™ flash chromatography cartridge (90 g), loading in DCM and eluting with 17.5-20-25% EtOAc in iso-hexanes. The foam thus obtained was triturated with iso-hexanes/Et$_2$O, then collected as a white solid by filtration, subjected to one displacement wash with 2:1 iso-hexanes:Et$_2$O and dried in a vacuum oven.

Yield: 6.63 g (53%)

LC-MS (Method 1): Rt=3.55 min, m/z=398 [M+H]$^+$

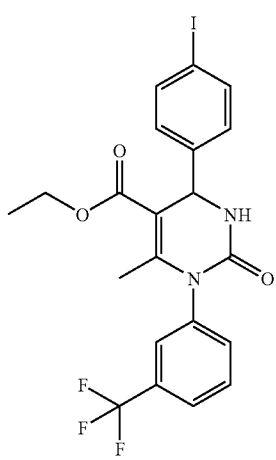

Intermediate 15

Intermediate 15 was prepared from 4-iodobenzaldehyde, ethyl acetoacetate and 3-(trifluoromethyl)phenylurea using a similar method to that used in the preparation of Intermediate 14.

Yield: (25%)

LC-MS (Method 1): Rt=4.17 min, m/z=531 [M+H]$^+$

Intermediate 16

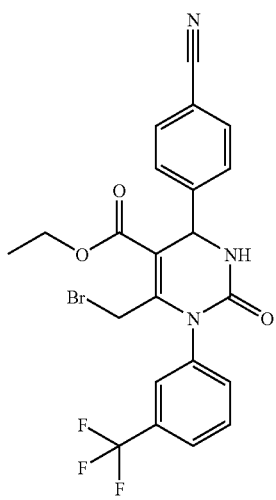

Intermediate 1 (5.00 g, 11.7 mmol) was dissolved in chloroform (140 ml) and bromine (1.87 g, 11.7 mmol) was added dropwise with stirring. After 30 min, a few more drops of bromine were added until the orange colour remained. Evaporation of the volatile materials gave a yellow foam.

Yield: quantitative

LC-MS (Method 2): Rt=3.82 min, m/z=508/510 [M+H]$^+$

The following intermediates were prepared in a similar manner:

| Intermediate | Structure | Precursor intermediate | Yield (%) | LC-MS Rt (min) | Mass [M + H]$^+$ Method 1 |
|---|---|---|---|---|---|
| 17 | 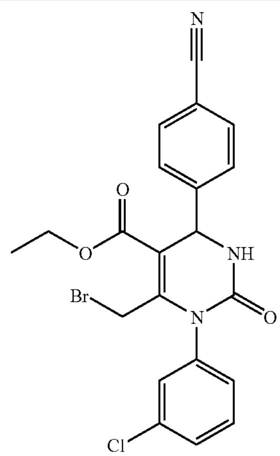 | 8 | 94 | 3.78 | 474/476 |
| 18 | 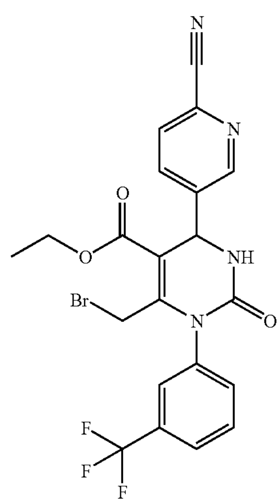 | 9 | 100 | 3.72 | 550/552 [M + CH$_3$CN]$^+$ |

-continued

| Intermediate | Structure | Precursor intermediate | Yield (%) | LC-MS Rt (min) Method 1 | Mass [M + H]+ |
|---|---|---|---|---|---|
| 19 | (structure: ethyl 4-(4-cyanophenyl)-6-(bromomethyl)-1-(3-methylphenyl)-2-oxo-1,2,3,4-tetrahydropyrimidine-5-carboxylate) | 10 | 100 | 3.77 | 454/456 |
| 20 | (structure: ethyl 4-(4-cyanophenyl)-6-(bromomethyl)-1-(3,5-difluorophenyl)-2-oxo-1,2,3,4-tetrahydropyrimidine-5-carboxylate) | 14 | 100 | 3.70 | 476/478 |
| 21 | (structure: ethyl 6-(bromomethyl)-4-(4-iodophenyl)-2-oxo-1-(3-(trifluoromethyl)phenyl)-1,2,3,4-tetrahydropyrimidine-5-carboxylate) | 15 | 100 | 4.31 | 609/611 |

Intermediate 22

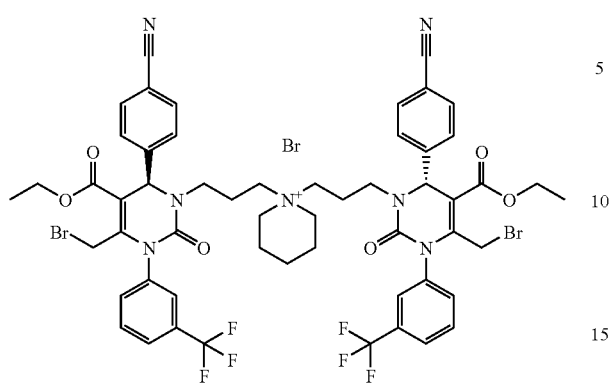

Intermediate 13 (32 mg, 0.029 mmol) was dissolved in chloroform (2 ml) and bromine (4 drops) was added. The solution was stirred at RT for 1 h after which the volatiles were evaporated. The product was obtained as a cream foam.

Yield: quantitative

LC-MS (Method 2): Rt=3.35 min, m/z=1182 [M]$^+$

The following intermediates were prepared in a similar manner:

| | Structure | Precursor intermediate | Yield (%) | LC-MS Rt (min) Method 2 | Mass ion |
|---|---|---|---|---|---|
| 23 | 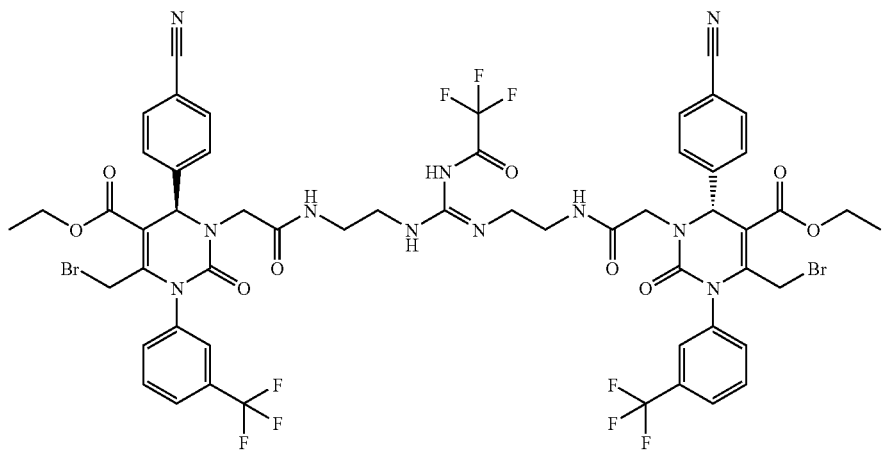 | 4 | 100 | 4.60 | 1338 [M + H]$^+$ |
| 24 | 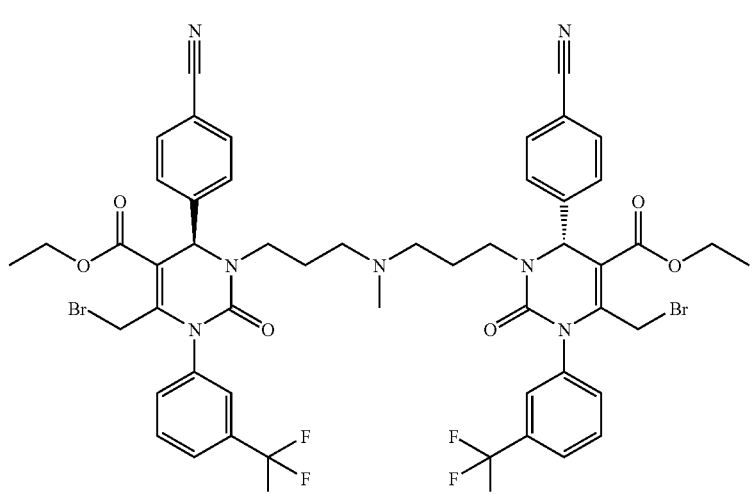 | 6 | 64 | 3.38 | 1128 [M + H]$^+$ |

-continued

| | Structure | Precursor intermediate | Yield (%) | LC-MS Rt (min) Method 2 | Mass ion |
|---|---|---|---|---|---|
| 25 | 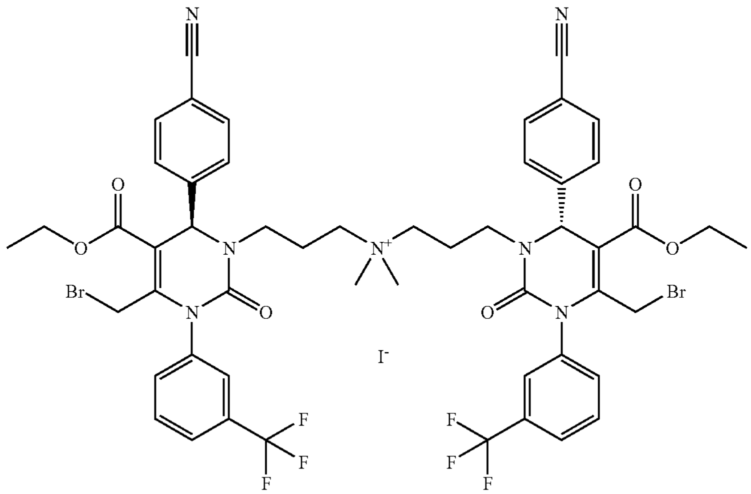 | 7 | 100 | 3.45 | 1142 [M]+ |
| 26 | 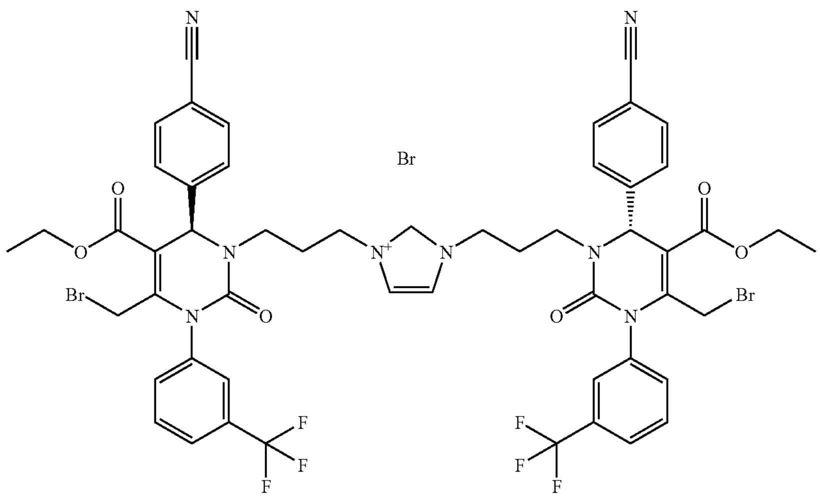 | 11 | 100 | 3.36 | 1165 [M]+ |
| 27 | 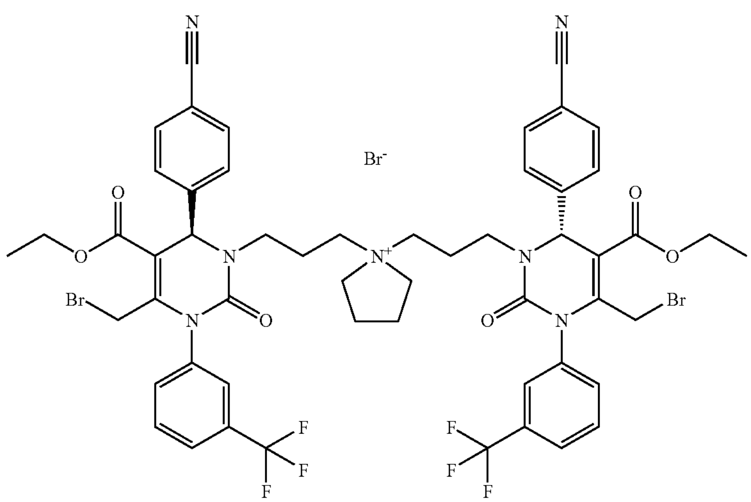 | 12 | 100 | 3.40 | 1168 [M]+ |

-continued

| | Structure | Precursor intermediate | Yield (%) | LC-MS Rt (min) Method 2 | Mass ion |
|---|---|---|---|---|---|
| 28 | 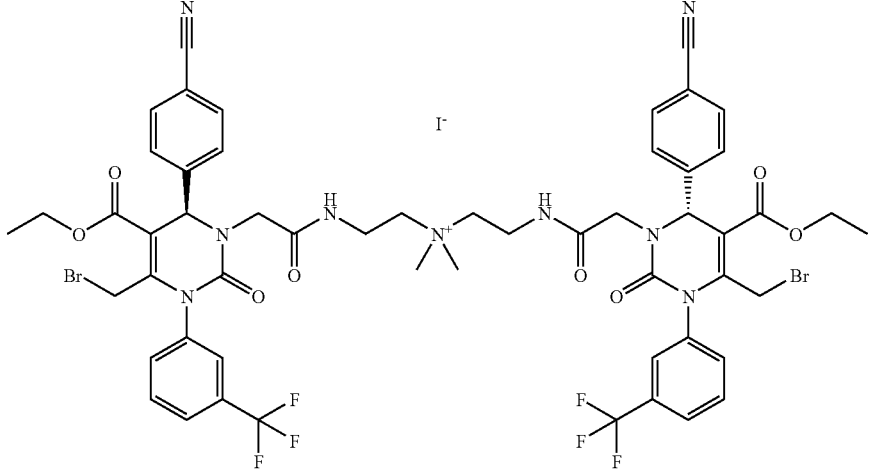 | 2 | 100 | 3.36 | 1228 [M]+ |

Intermediate 29

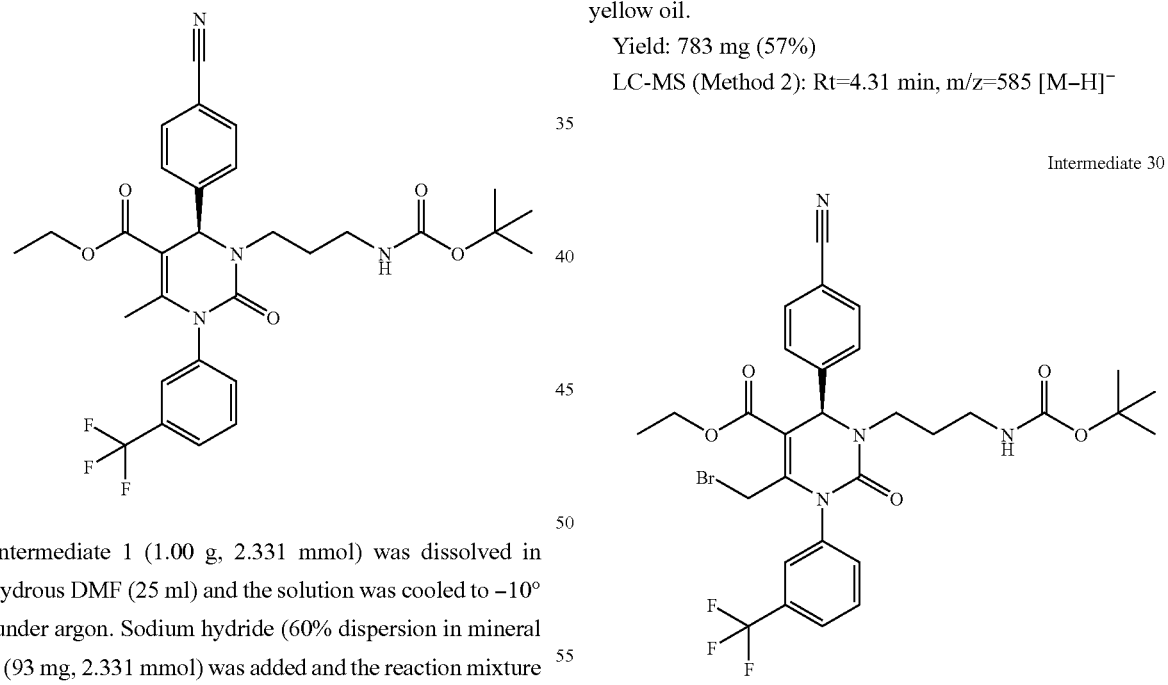

Intermediate 1 (1.00 g, 2.331 mmol) was dissolved in anhydrous DMF (25 ml) and the solution was cooled to −10° C. under argon. Sodium hydride (60% dispersion in mineral oil) (93 mg, 2.331 mmol) was added and the reaction mixture was stirred until effervescence had ceased. N-Boc-3-bromopropylamine (610 mg, 2.563 mmol) was added and stirring was continued at 0° C. for a further 2.5 h, after which time sat. aqueous ammonium chloride (60 ml) and EtOAc (60 ml) were added. The organic layer was separated and the aqueous solution was further extracted with EtOAc (60 ml). The organic extracts were combined and washed with water (50 ml) and sat. brine (30 ml), dried ($Na_2SO_4$) and evaporated. The residue was purified on an Isolute™ Si II cartridge eluting with 0-30% EtOAc in pentane to give the product as a pale yellow oil.

Yield: 783 mg (57%)

LC-MS (Method 2): Rt=4.31 min, m/z=585 [M−H]−

Intermediate 30

Intermediate 29 (776 mg, 1.32 mmol) was dissolved in DCM (20 ml) and N-bromosuccinimide (236 mg, 1.32 mmol) was added. The solution was stirred at RT for 1.5 h and then the mixture was diluted with DCM (80 ml), washed with sat. aqueous $NaHCO_3$ (50 ml), water (50 ml) and brine (30 ml), and dried ($Na_2SO_4$). Evaporation gave a pale yellow gum.

Yield: quantitative
LC-MS (Method 2): Rt=4.36 min, m/z=565/567 [M-Boc+2H]+

Intermediate 31

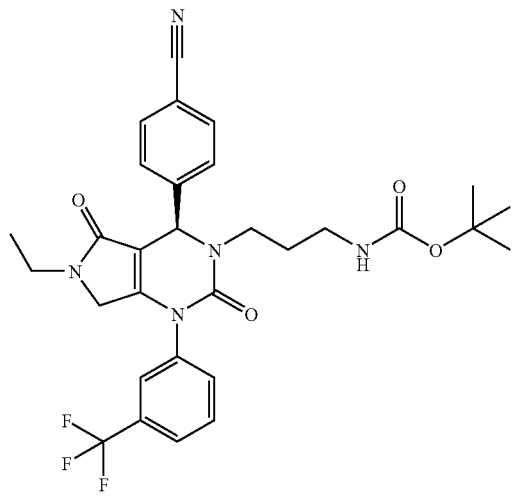

Intermediate 30 (731 mg, 1.099 mmol) was dissolved in acetonitrile (20 ml) and sodium hydrogen carbonate (277 mg, 3.297 mmol) and 2M ethylamine in THF (0.8 ml, 1.65 mmol) were added. The mixture was heated at 80° C. for 3.5 h, allowed to cool, filtered and evaporated. The residue was partitioned between DCM (70 ml) and water (50 ml). The organic layer was separated and evaporated, and the crude product was purified on an Isolute™ Si II cartridge (10 g) eluting with 40-80% EtOAc in pentane to give the product as a cream foam.

Yield: 297 mg (46%)
LC-MS (Method 2): Rt=3.71 min, m/z=582 [M−H]−

Intermediate 32

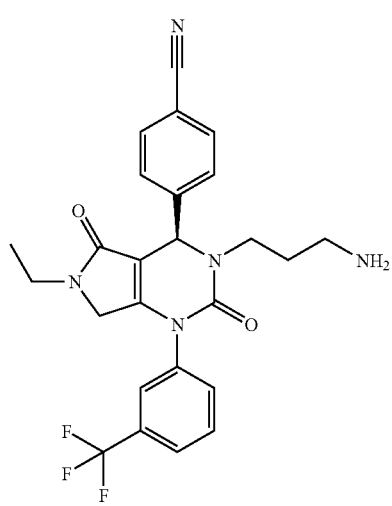

Intermediate 31 (292 mg, 0.501 mmol) was dissolved in 20% TFA in DCM (20 ml). After 2 h the volatiles were evaporated and the residue was dissolved in MeOH and loaded onto an Isolute™ SCX-2 cartridge (5 g) which had been pre-treated with MeOH. After flushing with MeOH, the product was eluted with 2M ammonia in MeOH. Evaporation of the UV active fractions gave the pure product as a pale yellow gum.

Yield: 221 mg (91%)

LC-MS (Method 2): Rt=2.33 min, m/z=484 [M+H]+

Intermediate 33

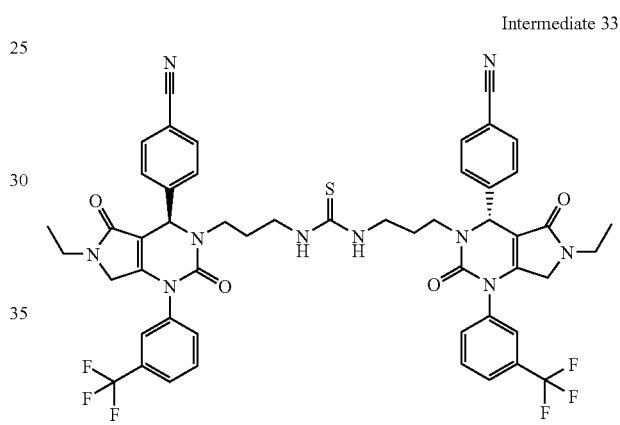

Intermediate 32 (214 mg, 0.443 mmol) was dissolved in DCM (10 ml) and 1,1'-thiocarbonyldipyridone (51 mg, 0.222 mmol) was added. The solution was allowed to stand at RT for 48 h and then treated with a resin bound amine for 15 min. After filtering, the solvent was evaporated and the crude product was purified on an Isolute™ Si II cartridge (5 g) eluting with 0-5% MeOH in EtOAc. The fractions that contained product were combined and evaporated, the residue dissolved in MeOH and passed through an Isolute™ SCX-2 cartridge (5 g), flushing further with methanol. Evaporation gave a white foam.

Yield: 160 mg (36%)

LC-MS (Method 2): Rt=3.91 min, m/z=1009 [M+H]+

Intermedaite 34

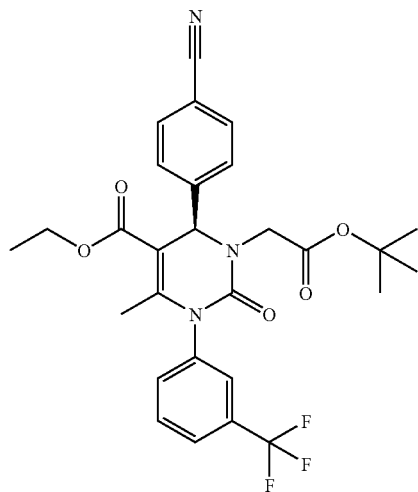

Intermediate 35

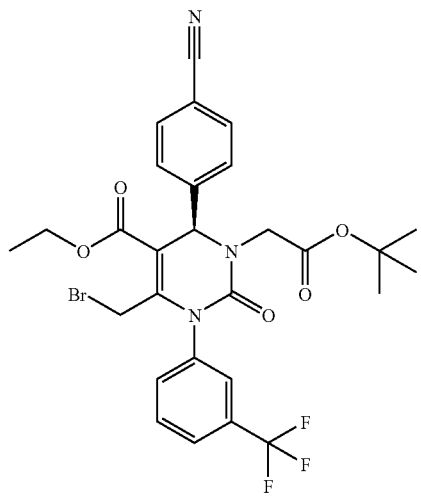

Intermediate 34 was prepared from Intermediate 1 and tert-butyl bromoacetate using a similar procedure to that used in the synthesis of Intermediate 29.

Yield: (80%)
LC-MS (Method 2): Rt=4.31 min, m/z=488 [M+H-tBu]$^+$

Intermediate 35 was prepared from Intermediate 34 using a similar method to that used in the preparation of Intermediate 30.

Yield: (41%)
LC-MS (Method 2): Rt=4.41 min, m/z=566/568 [M+H-tBu]$^+$

Intermediate 36

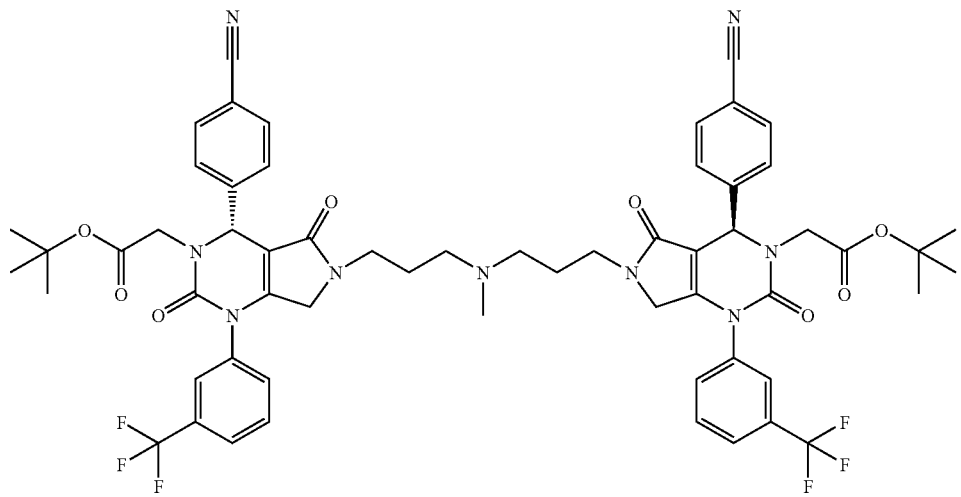

A solution of Intermediate 35 (467 mg, 0.751 mmol) in acetonitrile (15 ml) was treated with N,N-bis(3-aminopropyl)methylamine (54 mg, 0.375 mmol) and sodium hydrogen carbonate (252 mg, 3.00 mmol). The reaction was heated at 80° C. for 3.5 h. After allowing the mixture to cool, it was filtered and the filtrate evaporated. Chromatography using an Isolute™ Si II cartridge (10 g), and eluting with 1-20% MeOH in EtOAc, gave the pure product as a white solid.

Yield: 182 mg (43%)

LC-MS (Method 2): Rt=3.22 min, m/z=1136 [M+H]$^+$

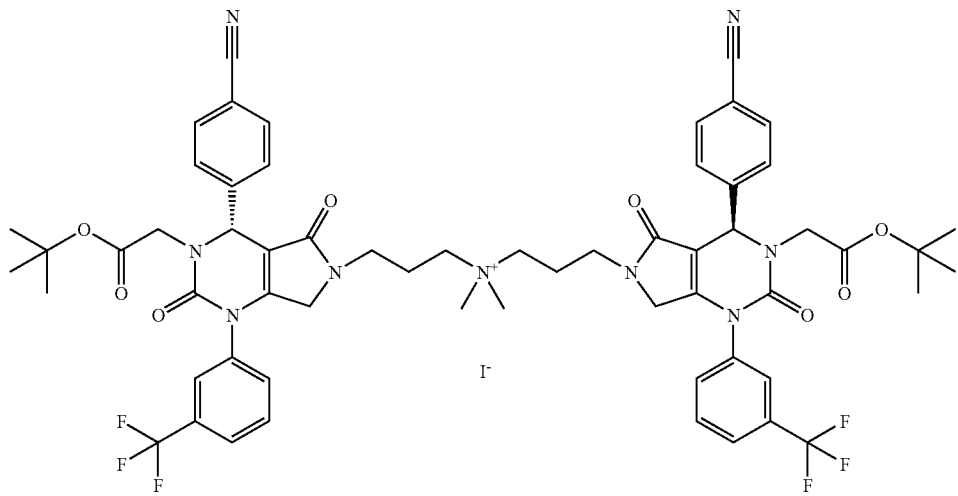

Intermediate 37

Intermediate 36 (177 mg, 0.156 mmol) was dissolved in a mixture of DCM (30 ml) and iodomethane (8 ml). After standing at RT for 3 days the volatiles were evaporated and the residue was taken up into acetonitrile (13 ml). Iodomethane (4 ml) and sodium hydrogen carbonate (39 mg, 0.468 mmol) were added and the mixture was heated at 80° C. under reflux. After 17 h the volatiles were evaporated and the residue was partitioned between DCM (50 ml) and water (50 ml). The organic phase was separated and dried (Na$_2$SO$_4$). Evaporation gave a beige foam.

Yield: 181 mg (91%)

LC-MS (Method 2): Rt=3.20 min, m/z=1150 [M]$^+$

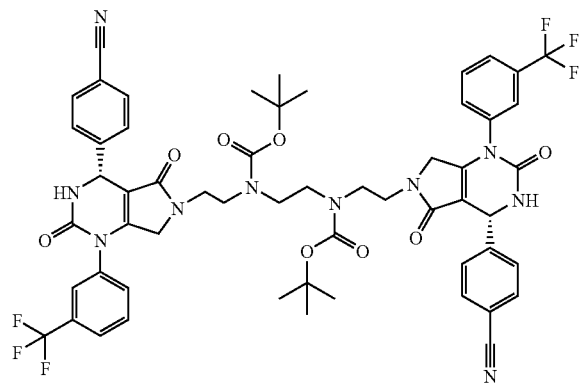

Intermediate 38

Intermediate 38 was prepared from Intermediate 16 and 0.5 equivalents of (2-aminoethyl){2-[(2-aminoethyl)tert-butoxycarbonylamino]ethyl}carbamic acid tert-butyl ester by a similar method to that used in the synthesis of intermediate 36.

Yield: (61%)

LC-MS (Method 2): Rt=3.58 min, m/z=1009 [M+H]$^+$

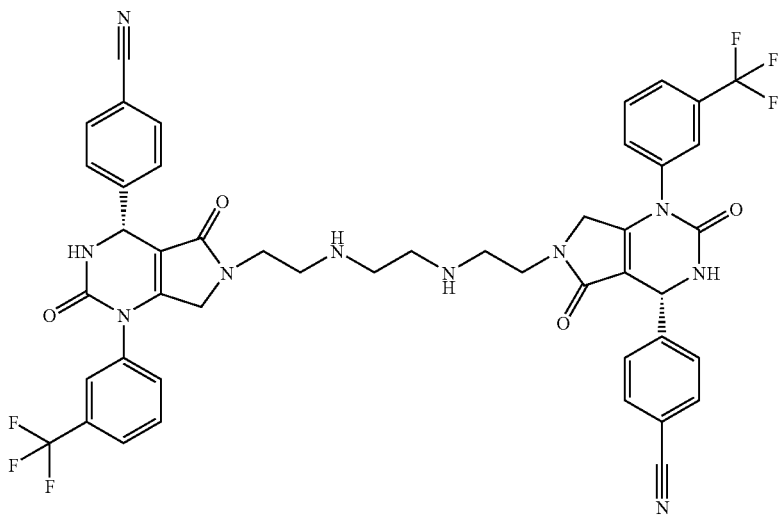

Intermediate 39

The tert-butyloxycarbonyl protecting groups in Intermediate 39 were removed using a procedure analogous to that described for the deprotection of Intermediate 31.
Yield: (89%)
LC-MS (Method 2): Rt=2.17 min, m/z=909 [M+H]+

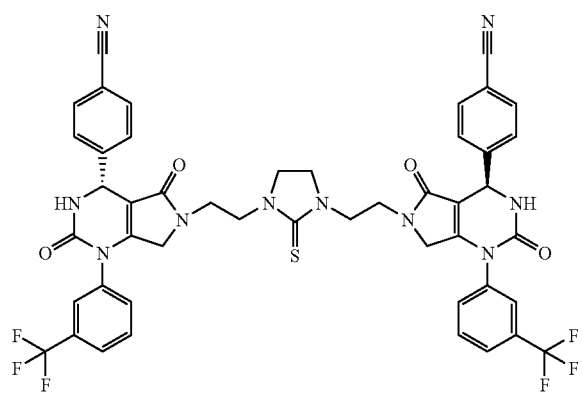

Intermediate 40

A solution of Intermediate 39 (219 mg, 0.241 mmol) and 1,1'-thiocarbonyldipyridone (28 mg, 0.121 mmol) in DCM (10 ml) was allowed to stand at RT for 24 h. A further portion of 1,1'-thiocarbonyldipyridone (20 mg, 0.086 mmol) was added and, after 4 h, the reaction mixture was treated with an amine resin. The mixture was stirred for 15 min, filtered and loaded into an Isolute™ SCX-2 cartridge (10 g) which had been conditioned with MeOH. The cartridge was flushed with MeOH and the eluent was evaporated. The white solid was chromatographed on an Isolute™ Si II cartridge (10 g) eluting with 0-10% MeOH in EtOAc. Evaporation gave a white solid.
Yield: 150 mg (66%)
LC-MS (Method 2): Rt=3.00 min, m/z=951 [M+H]+

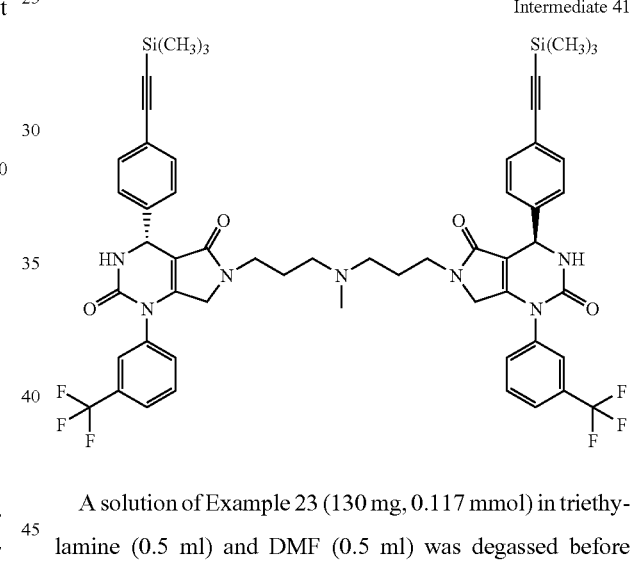

Intermediate 41

A solution of Example 23 (130 mg, 0.117 mmol) in triethylamine (0.5 ml) and DMF (0.5 ml) was degassed before (trimethylsilyl)acetylene (34 μl, 0.235 mmol), copper (I) iodide (1.7 mg, 3 mol %) and bis(triphenylphosphine)palladium (II) chloride (8.4 mg, 5 mol %) were added then stirred and heated at 115° C. under argon for 2 h. The cooled mixture was poured into dilute sulphuric acid (25 ml) and extracted with EtOAc (2×25 ml). These extracts were washed with brine (10 ml) before the organic phase was isolated, dried (MgSO₄), filtered and concentrated in vacuo. Purification was achieved using an Isolute™ Si II cartridge eluting with a 0-10% MeOH in DCM gradient. The product was isolated as a cream solid.
Yield: 48 mg (39%)
LC-MS (Method 1): Rt=3.36 min, m/z 1050 [M+H]+

Intermediate 42

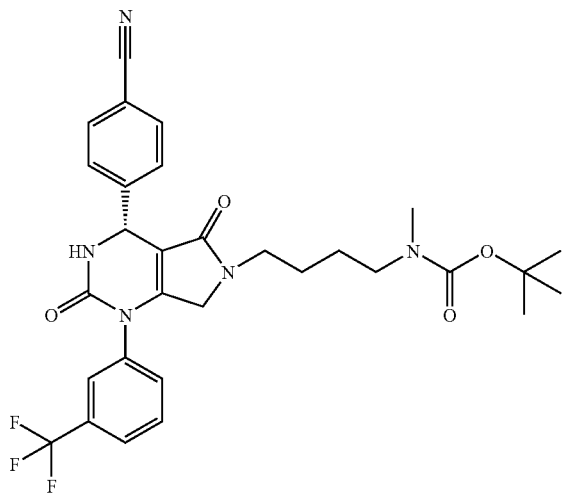

A solution of Intermediate 16 (200 mg, 0.394 mmol) and (3-aminobutyl)methylcarbamic acid tert-butyl ester (370 mg, 1.83 mmol) in acetonitrile (10 ml) was heated at 40° C. for 2 h. The solvent was evaporated and the residue was dissolved in MeOH and loaded onto an Isolute™ SCX-2 cartridge (5 g) which had been conditioned with MeOH. The product was flushed off with MeOH.

Yield: 225 mg (98%)
LC-MS (Method 2): Rt=3.63 min, m/z=484 [M+H-Boc]$^+$

Intermediate 43

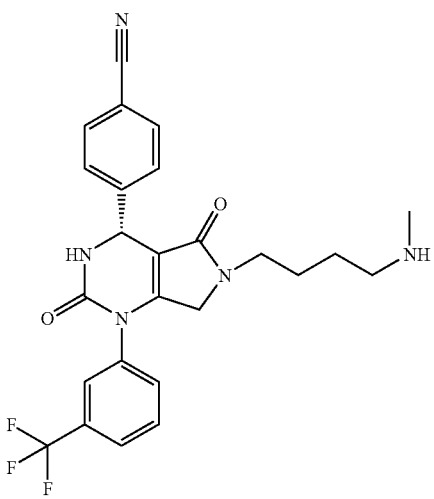

Intermediate 42 was deprotected in a similar manner to Intermediate 31.
Yield: (94%)
LC-MS (Method 2): Rt=2.11 min, m/z=484 [M+H]$^+$ Intermediate 44

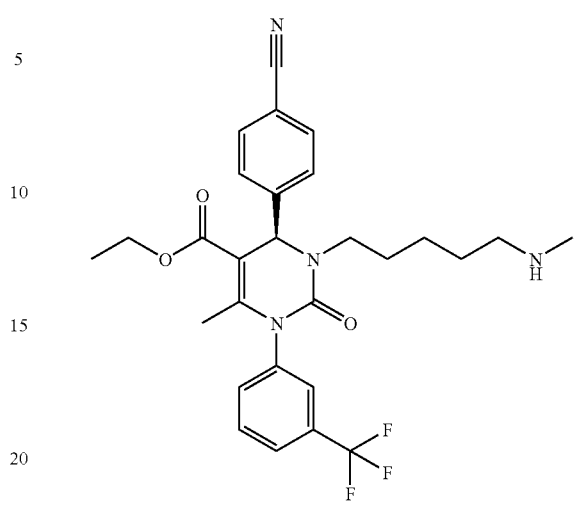

Intermediate 3 (219 mg, 0.379 mmol) was dissolved in acetonitrile (13 ml) and a 2M solution of methylamine in THF (2 ml) was added. The solution was heated at 50° C. for 3 h and then the solution was allowed to stand at RT for 3 days. The volatiles were evaporated and the residue was partitioned between DCM (100 ml) and water (80 ml). The organic layer was separated and dried ($Na_2SO_4$). Evaporation gave a white foam.

Yield: 170 mg (85%)
LC-MS (Method 2): Rt=2.67 min, m/z=529 [M+H]$^+$

Intermediate 45

A solution of Intermediate 44 (165 mg, 0.313 mmol) and phenoxypropyl bromide (67 mg, 0.313 mmol) in acetonitrile (10 ml) was treated with sodium hydrogen carbonate (53 mg, 0.626 mmol) and the reaction mixture was heated at 80° C. for 4 days. The solution was decanted onto an Isolute™ SCX-2 cartridge (5 g) which had been conditioned with MeOH. The cartridge was flushed with MeOH and then the product was eluted with 2M $NH_3$ in MeOH. Evaporation gave a colourless gum.

Yield: 105 mg (51%)
LC-MS (Method 1): Rt=2.98 min, m/z=663 [M+H]$^+$

Intermediate 46

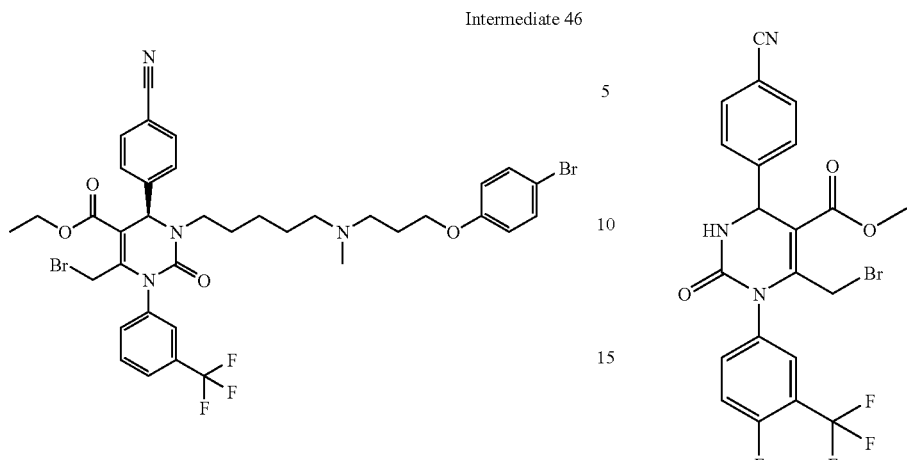

A solution of Intermediate 45 (100 mg, 0.151 mmol) in chloroform (6 ml) was treated with bromine (10 μl). After 1 h a further portion of bromine (20 μl) was added. The volatiles were evaporated to give the di-brominated product.

Yield: quantitative
LC-MS (Method 2): Rt=3.12 min, m/z=821 [M+H]$^+$

Intermediate 47

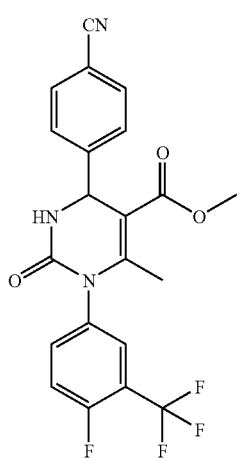

A mixture of (4-fluoro-3-trifluoromethylphenyl)urea (WO2008/003412) (2.5 g, 11.26 mmol), 4-cyanobenzaldehyde (1.77 g, 13.51 mmol), methyl acetoacetate (1.57 g, 13.51 mmol) and polyphosphoric acid (6.5 g) in THF (45 ml) was heated at reflux under argon for 20 h. The bulk of the solvent was evaporated under reduced pressure and the residue partitioned between water and ethyl acetate. The organic phase was washed with water, aqueous potassium carbonate, water, and brine, dried (Na$_2$SO$_4$) and evaporated. The crude material was purified using a CombiFlash® companion (330 g cartridge) to yield the desired product as a pale yellow solid.

Yield: 3.03 g, 62%
LC-MS (Method 5): Rt=3.64 min, m/z=434 [M+H]$^+$

Intermediate 48

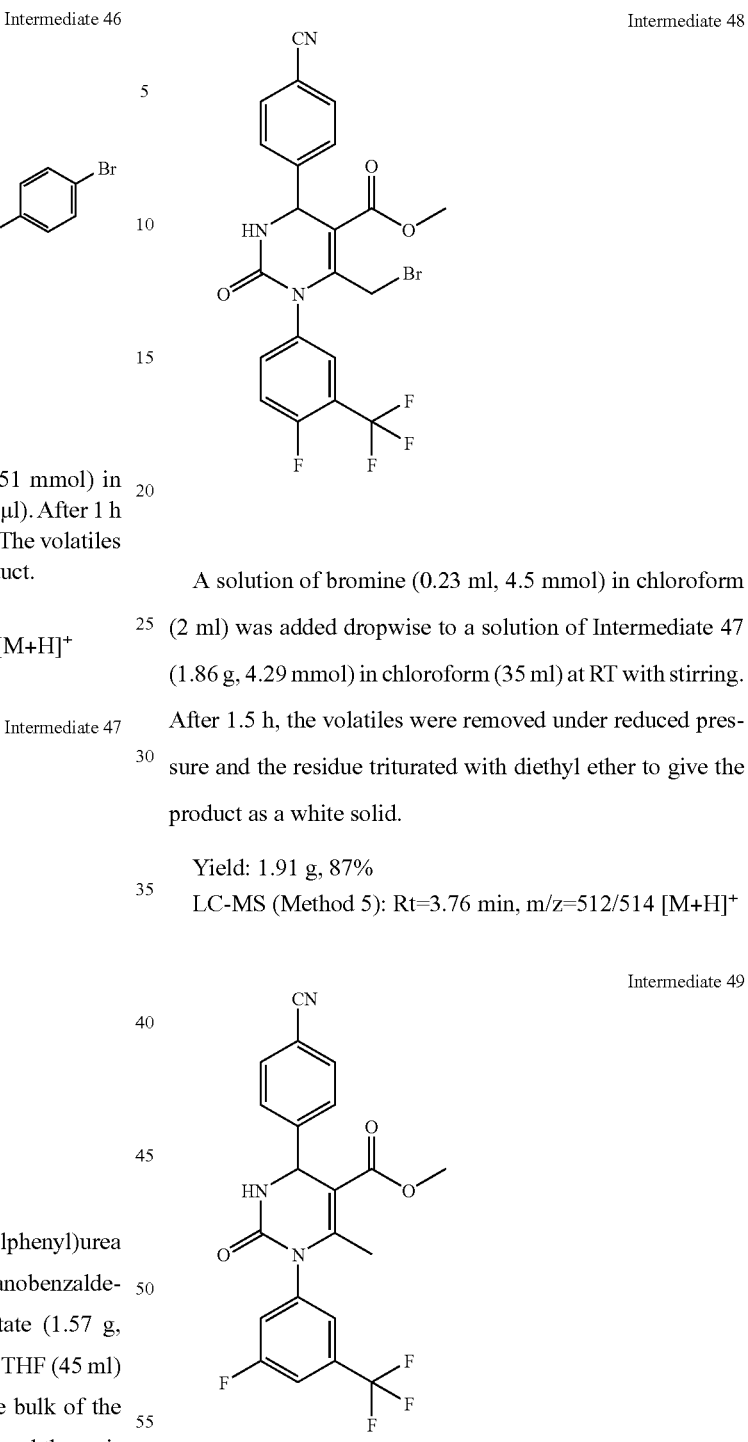

A solution of bromine (0.23 ml, 4.5 mmol) in chloroform (2 ml) was added dropwise to a solution of Intermediate 47 (1.86 g, 4.29 mmol) in chloroform (35 ml) at RT with stirring. After 1.5 h, the volatiles were removed under reduced pressure and the residue triturated with diethyl ether to give the product as a white solid.

Yield: 1.91 g, 87%
LC-MS (Method 5): Rt=3.76 min, m/z=512/514 [M+H]$^+$

Intermediate 49

Intermediate 49 was prepared from (3-fluoro-5-trifluoromethylphenyl)urea (WO2008/003412), methyl acetoacetate and 4-cyanobenzaldehyde using a method similar to that used for Intermediate 47.

Yield: 1.50 g, 51%
LC-MS (Method 5): Rt=3.68 min, m/z=434 [M+H]$^+$

Intermediate 50

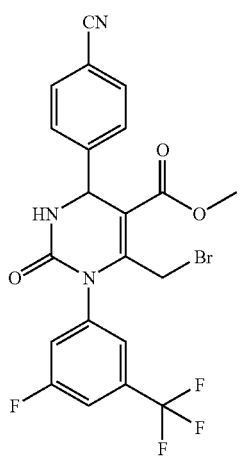

Intermediate 50 was prepared from Intermediate 49 in an analogous manner as Intermediate 48.

Yield: 0.73 g, 77%

LC-MS (Method 5): Rt=3.78 min, m/z=512/514 [M+H]$^+$

Intermediate 51

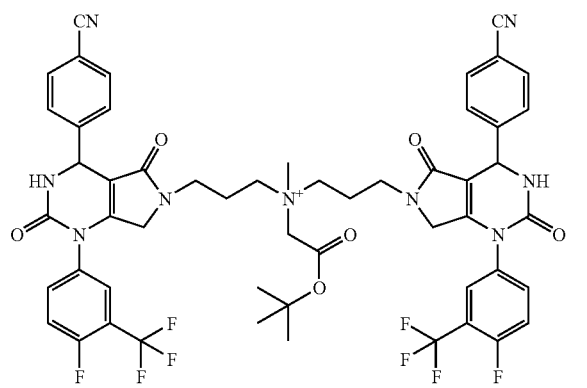

t-Butyl bromoacetate (1.42 g, 7.30 mmol) was added to a solution of Example 3 (0.46 g, 0.487 mmol) in acetonitrile (15 ml) followed by DIPEA (0.94 g, 7.30 mmol) at RT. The reaction mixture was stirred at 50° C. for 17 h. The volatiles were removed under reduced pressure and the residue triturated with diethyl ether (30 ml). The solid was collected by filtration under suction and then partitioned between water and DCM. The organic layer was separated, dried (Na$_2$SO$_4$) and evaporated. The crude product was purified on an Isolute® SPE Si II cartridge (10 g) eluting with DCM, 10% MeOH in DCM and then 15% MeOH in DCM. Product containing fractions were combined and the solvent removed under reduced pressure to give the desired product as a cream coloured solid.

Yield: 0.35 g, 63%

LC-MS (Method 5): Rt=2.89 min, m/z=1058 [M]$^+$

Example 1

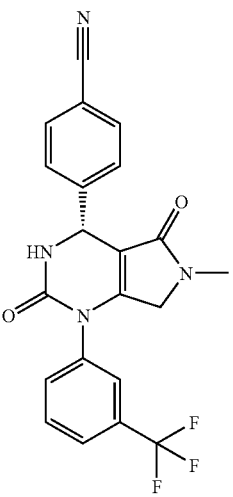

To a solution of Intermediate 16 (200 mg, 0.394 mmol) in acetonitrile (5 ml) were added a 2M solution of methylamine in THF (197 µl, 0.394 mmol) and sodium hydrogen carbonate (165 mg, 1.97 mmol). The solution was heated at 80° C. for 16 h and then the mixture was filtered. The product was purified by HPLC System 1 and the fractions containing pure material were combined and freeze dried. The product was obtained as a yellow solid.

Yield: 62 mg (38%)

LCMS (Method 3): Rt=8.67 min, m/z=413 [M+H]$^+$

1H NMR (400 MHz, DMSO-d6): δ=2.73 (s, 3H), 3.78 (d, 1H), 3.83 (d, 1H), 5.44 (d, 1H), 7.67-7.82 (m, 5H), 7.85-7.90 (m, 2H), 7.91 (m, 1H), 8.19 (d, 1H) ppm.

The following examples were prepared in a similar manner from Intermediate 16 and an amine:

| Example | Structure | Yield (%) | LC-MS (Method 1) Rt (min) | Mass [M + H]+ |
|---|---|---|---|---|
| 2 | 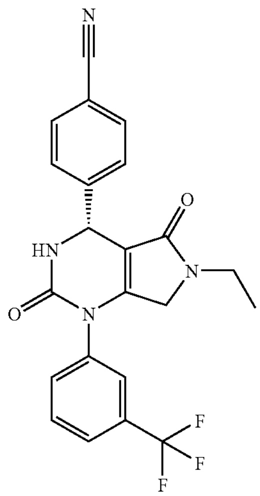 | 50 | 9.11 | 427.04 |
| 3 | 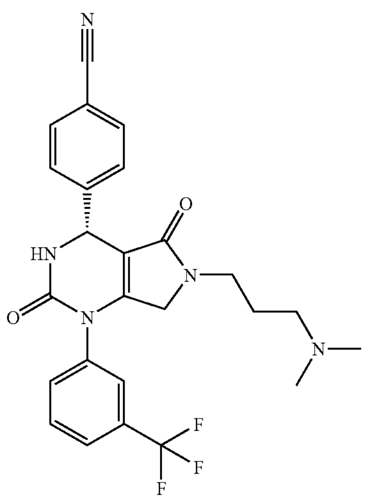 | 7 | 6.13 | 484.11 |
| 4 | 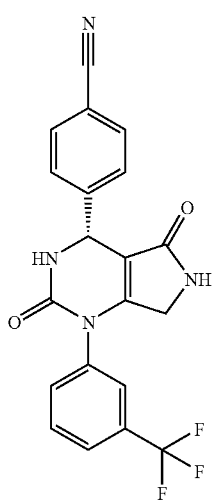 | 5 | 8.03 | 399.00 |

-continued

| Example | Structure | Yield (%) | LC-MS (Method 1) Rt (min) | Mass [M + H]+ |
|---|---|---|---|---|
| 5 | 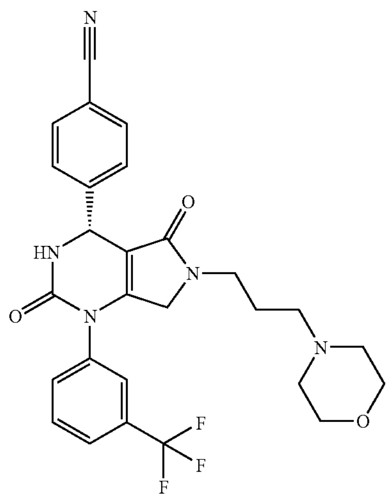 | 27 | 6.39 | 526.09 |
| 6 | 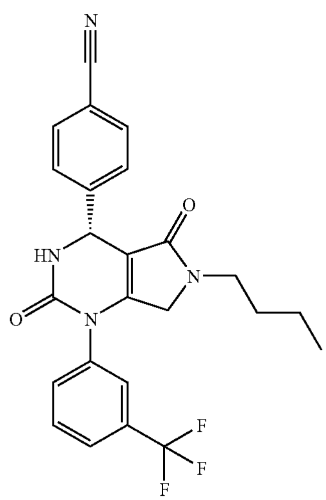 | 62 | 10.40 | 455.04 |
| 7 | 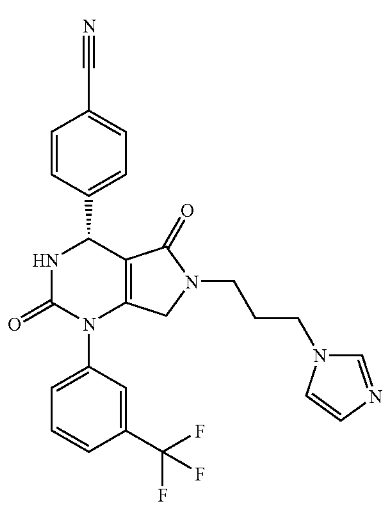 | 37 | 6.43 | 507.01 |

Example 8

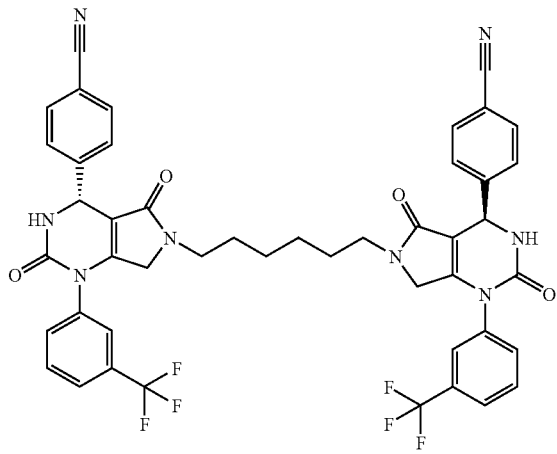

To a solution of hexamethylenediamine (0.197 mmol) in acetonitrile (5 ml) were added Intermediate 16 (200 mg, 0.394 mmol) and sodium hydrogen carbonate (165 mg, 1.97 mmol) and the reaction mixture was heated to 80° C. for 16 h. The mixture was cooled to RT then the solution was filtered and the solvent evaporated. The crude product was purified by HPLC System 1. The product-containing fractions were combined and freeze dried. The product was obtained as a white solid.

Yield: 50 mg (29%)

LCMS (Method 3): m/z=879 [M+H]$^+$

1H NMR (400 MHz, DMSO-d6): δ=1.09 (br s, 4H); 1.29 (br s, 4H); 3.02-3.20 (m, 4H); 3.79 (s, 4H); 5.44 (d, 2H); 7.68-7.92 (m, 16H); 8.19 (d, 2H) ppm.

In analogy to the procedure for Example 8, the following compounds were prepared from the indicated intermediate and the appropriate diamine:

| Example | Structure | Precursor Intermediate | Yield (%) | LC-MS Rt (min) | Mass [M + H]$^+$ |
|---|---|---|---|---|---|
| 9 | 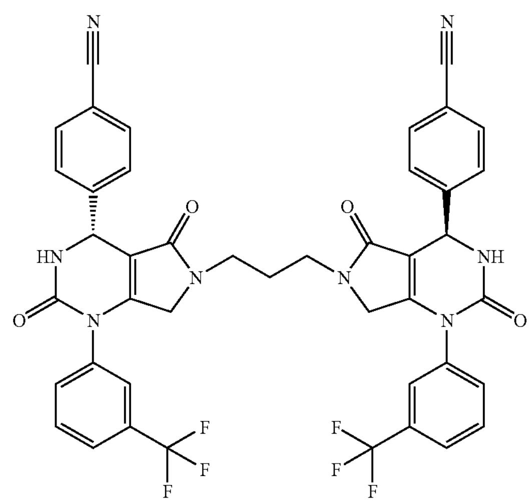 | 16 | 4 | 10.3 (Method 3) | 836.9 |

| Example | Structure | Precursor Intermediate | Yield (%) | LC-MS Rt (min) | Mass [M + H]+ |
|---|---|---|---|---|---|
| 10 | 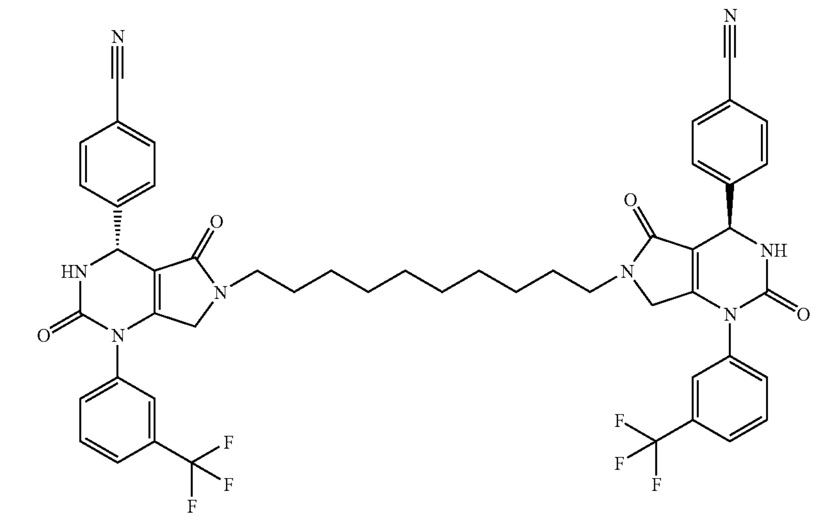 | 16 | 28 | 12.49 (Method 3) | 935.06 |
| 11 | 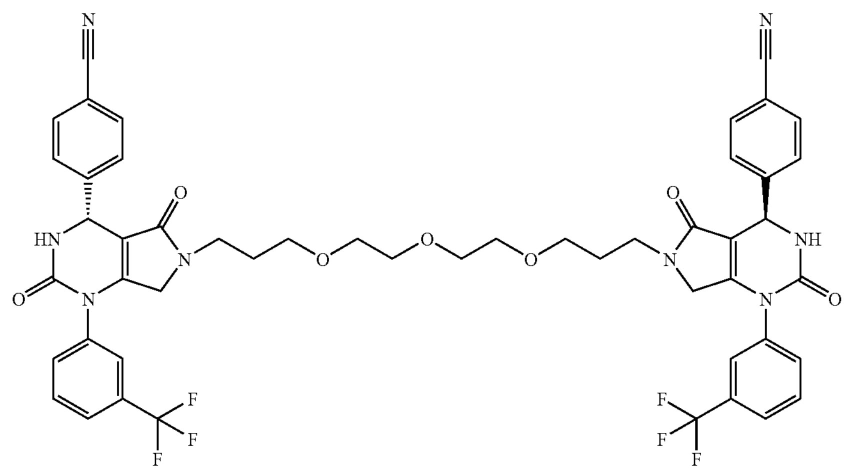 | 16 | 34 | 10.56 (Method 3) | 983.02 |
| 12 | 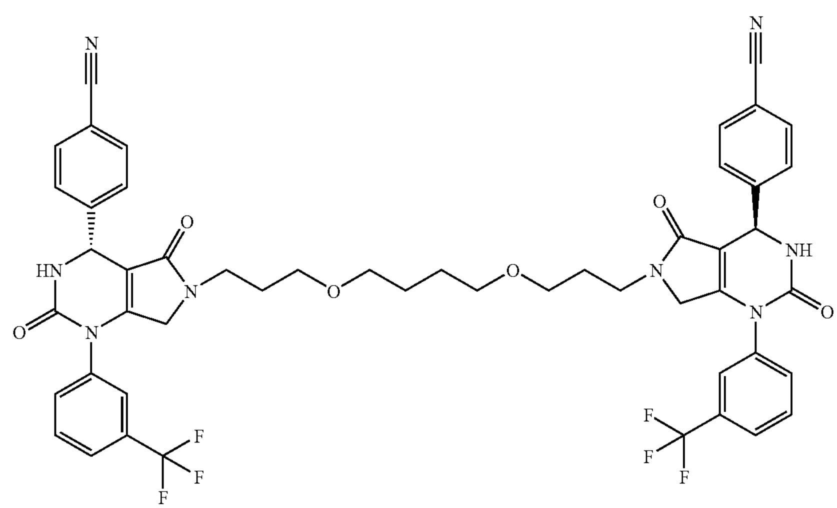 | 16 | 29 | 11.09 (Method 3) | 966.96 |

-continued

| Example | Structure | Precursor Intermediate | Yield (%) | LC-MS Rt (min) | Mass [M + H]+ |
|---|---|---|---|---|---|
| 13 | 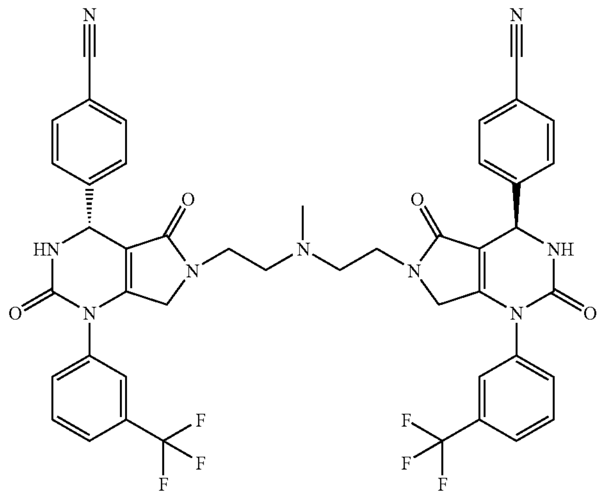 | 16 | 15 | 7.86 (Method 3) | 879.99 |
| 14 | 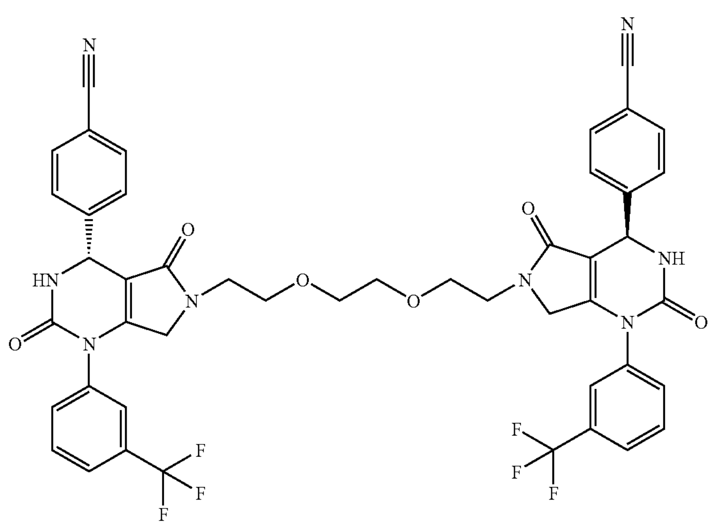 | 16 | 28 | 10.26 (Method 3) | 911.00 |

-continued
| Example | Structure | Precursor Intermediate | Yield (%) | LC-MS Rt (min) | Mass [M + H]+ |
|---|---|---|---|---|---|
| 15 | 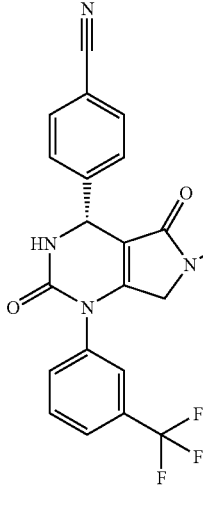 | 16 | 19 | 7.66 (Method 3) | 963.06 |
| 16 | 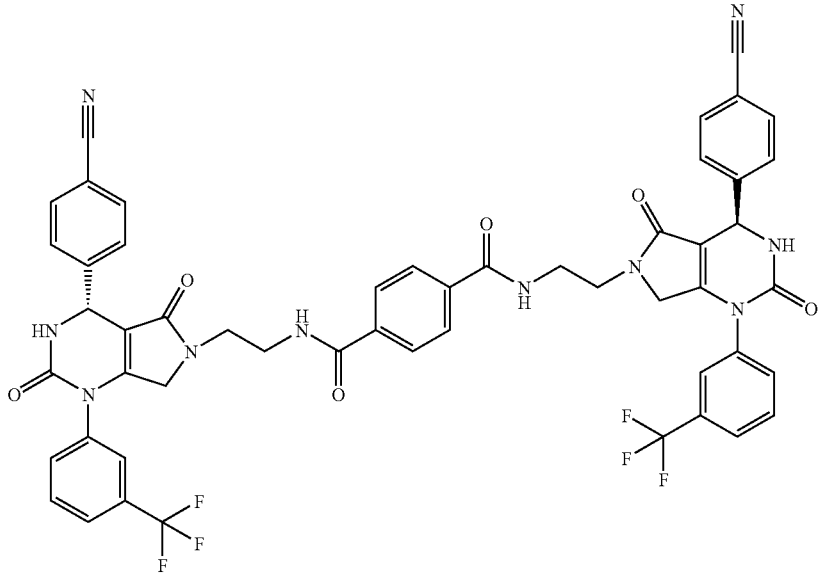 | 16 | 13 | 9.57 (Method 3) | 1012.95 |

-continued

| Example | Structure | Precursor Intermediate | Yield (%) | LC-MS Rt (min) | Mass [M + H]+ |
|---|---|---|---|---|---|
| 17 | 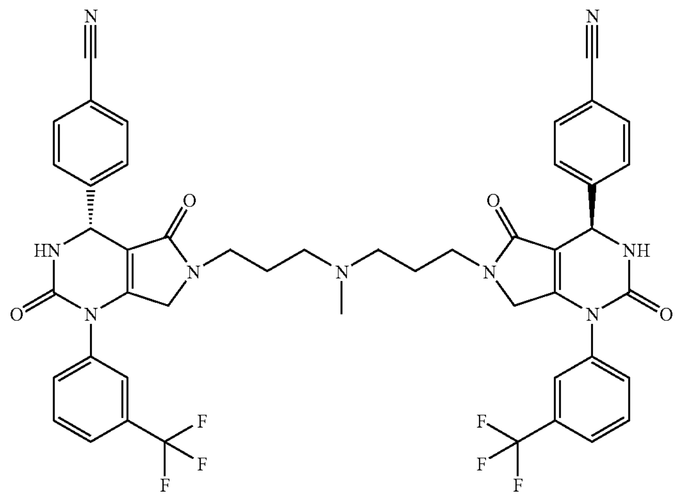 | 16 | 6 | 8.02 (Method 3) | 908.04 |
| 18 | 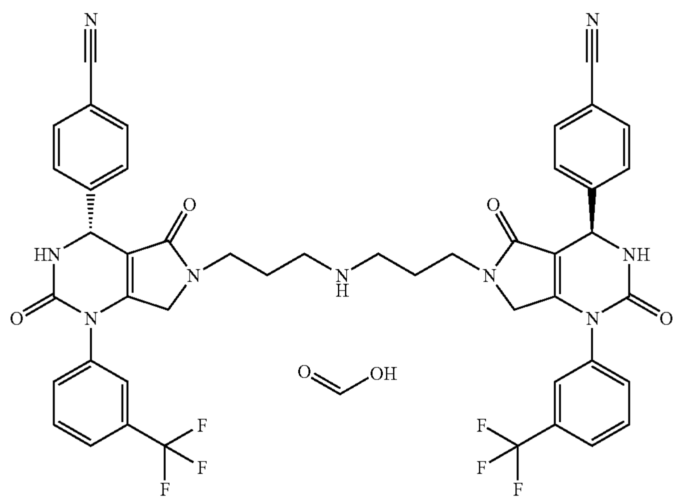 | 16 | 55 | 8.08 (Method 3) | 894.48 |
| 19 | 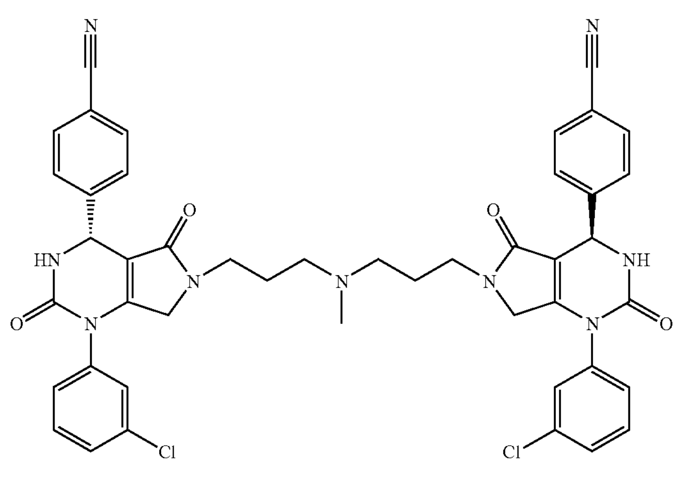 | 17 | 61 | 7.56 (Method 3) | 840.48 |

-continued

| Example | Structure | Precursor Intermediate | Yield (%) | LC-MS Rt (min) | Mass [M + H]+ |
|---|---|---|---|---|---|
| 20 | 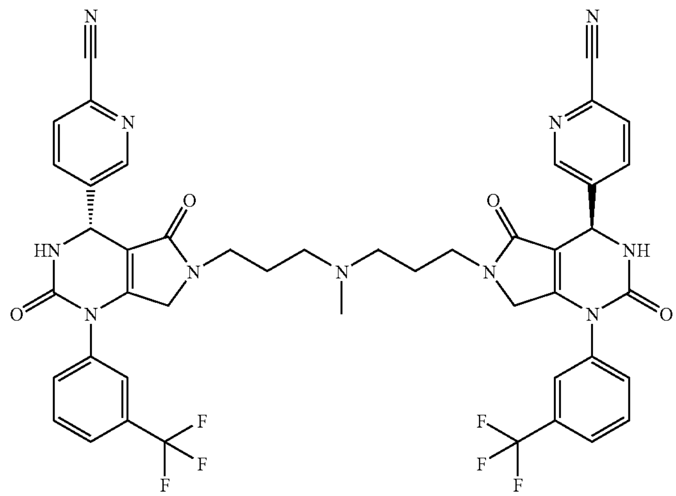 | 18 | 54 | 7.31 (Method 4) | 910.47 |
| 21 | 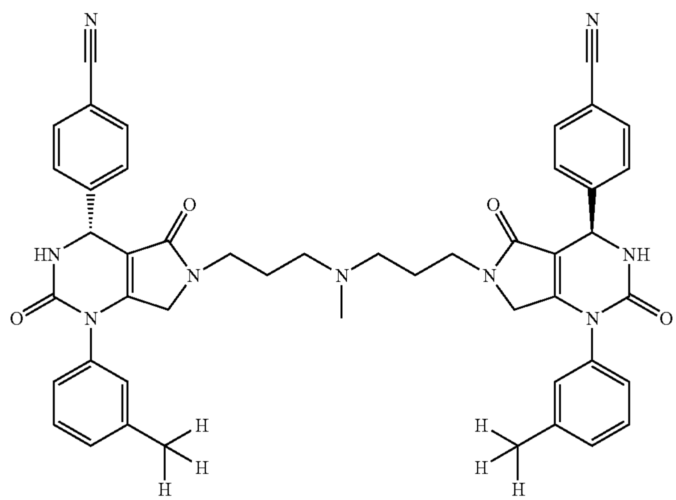 | 19 | 66 | 6.95 (Method 4) | 800.46 |
| 22 | 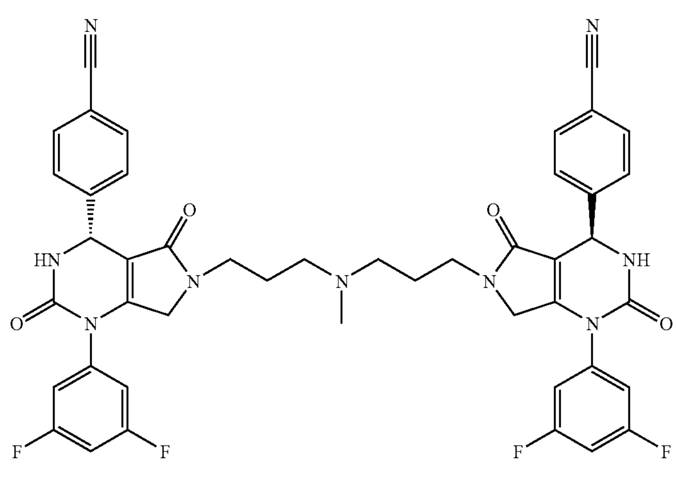 | 20 | 59 | 7.36 (Method 3) | 844.51 |

-continued
| Example | Structure | Precursor Intermediate | Yield (%) | LC-MS Rt (min) | Mass [M + H]+ |
|---|---|---|---|---|---|
| 23 | 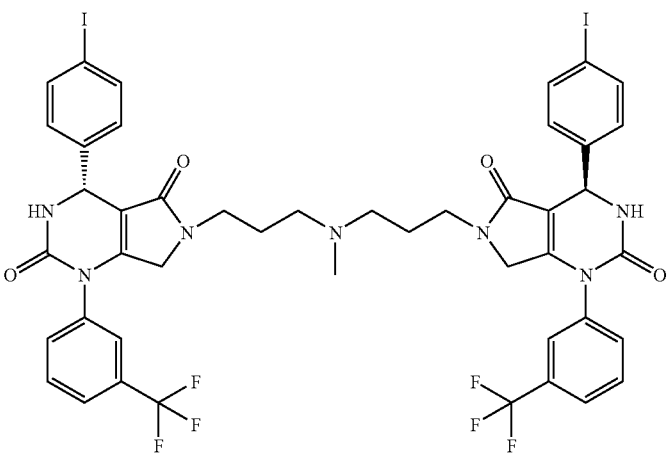 | 21 | 60 | 9.02 (Method 3) | 1110.38 |
Example 24
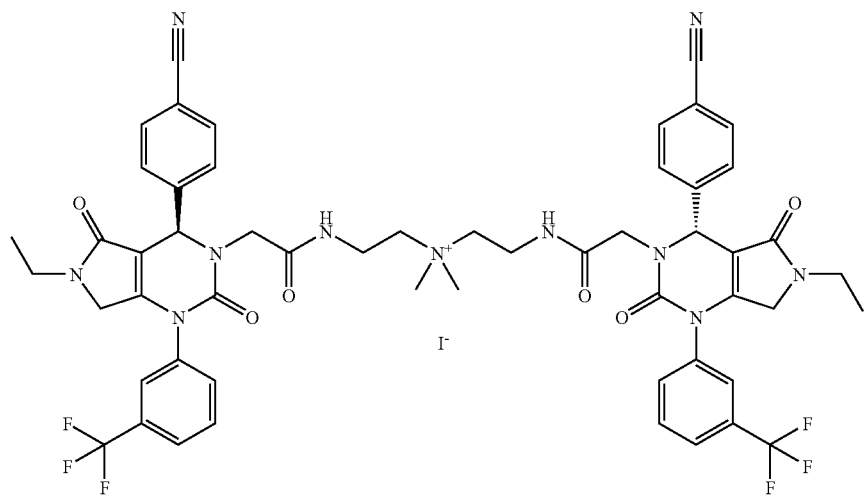

To a solution of Intermediate 28 in acetonitrile (5 ml) were added NaHCO$_3$ (92 mg, 1.10 mmol) and 2M ethylamine in THF (220 µl, 0.44 mmol). The reaction mixture was heated at 80° C. for 3.5 h. A further amount of 2M ethylamine in THF (220 µl, 0.44 mmol) was added and mixture was heated at 80° C. for 4 h. The mixture was filtered and the volatiles were evaporated. The crude product was purified using HPLC System 1 and the fractions were combined and freeze-dried to give the product, which was purified further using HPLC System 1. The pure fractions were combined and freeze-dried to give the product as a cream solid.

Yield: 16 mg (7%)

LC-MS (Method 3): Rt=8.69 min, m/z=1064.06 [M$^+$]

The following examples were prepared in a similar manner:

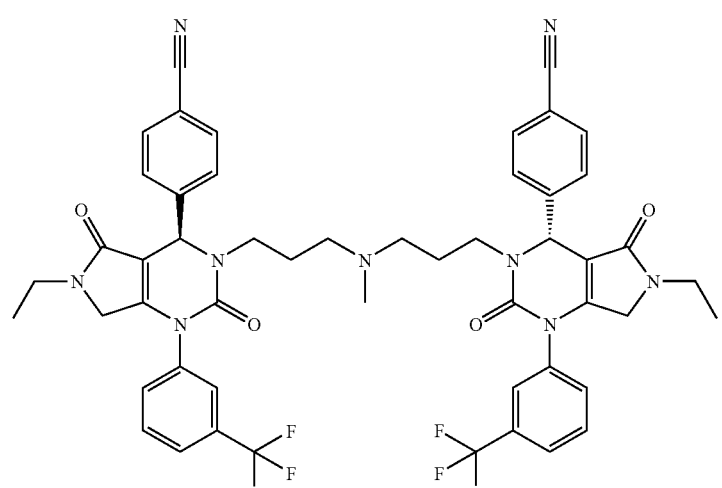

| | Structure | Precursor Intermediate | Yield (%) | LC-MS Rt (min) | Mass [M + H]$^+$ or [M]$^+$ |
|---|---|---|---|---|---|
| 25 | 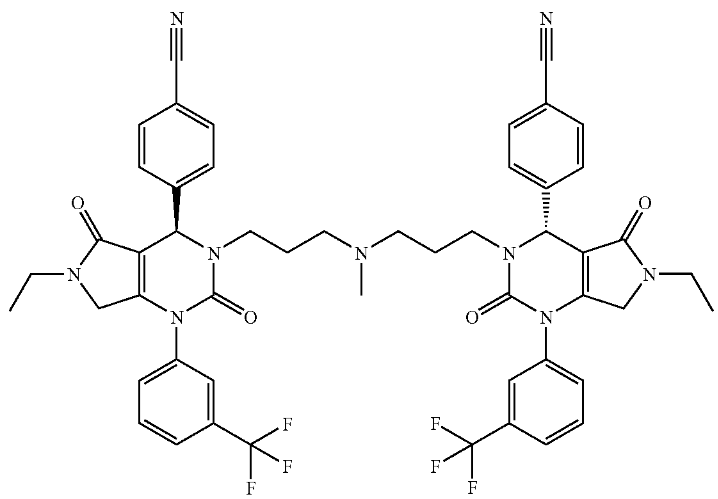 | 24 | 49 | 2.70 (Method 2) | 964 |
| 26 | 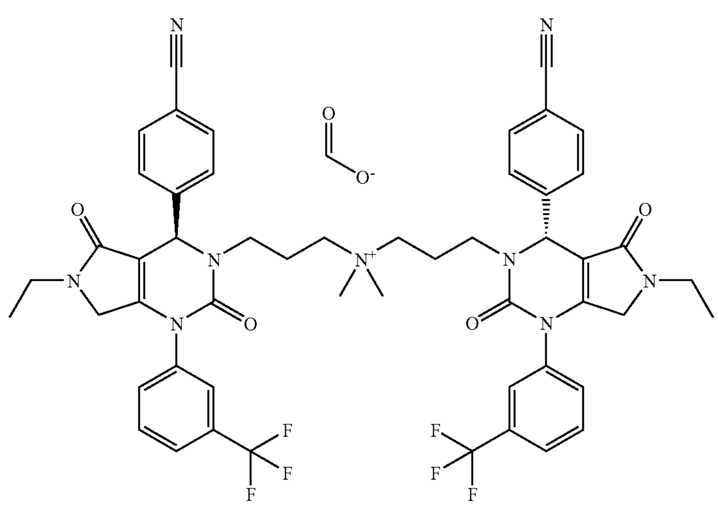 | 25 | 7 | 9.33 (Method 3) | 978.22 |

-continued
| | Structure | Precursor Intermediate | Yield (%) | LC-MS Rt (min) | Mass [M + H]+ or [M]+ |
|---|---|---|---|---|---|
| 27 | 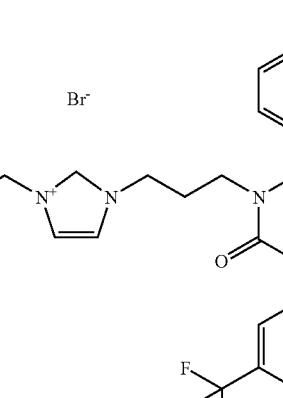 | 26 | 42 | 8.92 (Method 4) | 1001.50 |
| 28 | 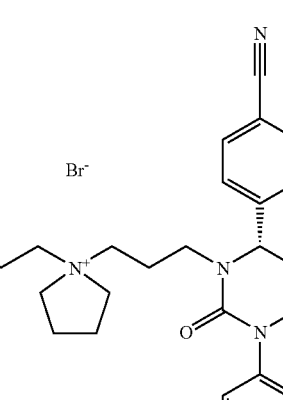 | 27 | 37 | 8.99 (Method 4) | 1004.52 |
| 29 | 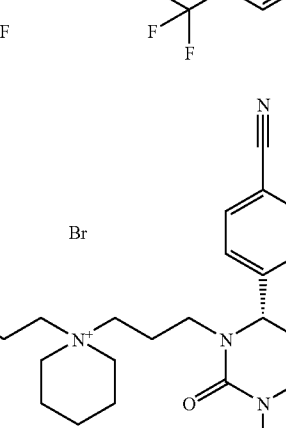 | 22 | 25 | 9.05 (Method 4) | 1018.53 |

Example 30

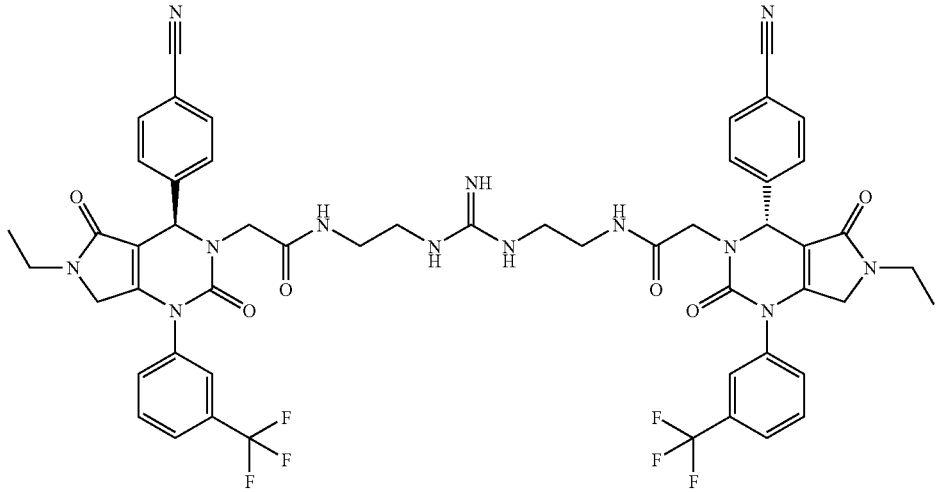

Intermediate 23 (195 mg, 0.146 mmol) was dissolved in acetonitrile (10 ml) and NaHCO$_3$ (61 mg, 0.73 mmol) and 2M ethylamine in THF (1.5 ml, 2.917 mmol) were added. The reaction mixture was heated at 80° C. for 4 h and then filtered and evaporated. The residue was dissolved in MeOH (12 ml) and a solution of K$_2$CO$_3$ (242 mg, 1.75 mmol) in water (5 ml) was added. The mixture was stirred at RT and after 30 min EtOAc (50 ml) and water (50 ml) were added. The organic solution was isolated, washed with brine (30 ml), dried (Na$_2$SO$_4$) and evaporated. The crude product was purified using HPLC System 1 and freeze-dried to give the product as a pale cream solid.

Yield: 49 mg (31%)

LC-MS (Method 3): Rt=8.96 min, m/z=1078.08 [M+H]$^+$

Example 31

Tetra-n-butylammonium fluoride solution (1M in THF, 45 µl, 0.045 mmol) was added to a stirred solution of Intermediate 41 (45 mg, 0.043 mmol) in THF (2 ml) at RT. The solvent was removed in vacuo after 1.5 h, water (25 ml) added and extracted with EtOAc (2×25 ml). These extracts were washed with brine (10 ml) before the organic phase was isolated, dried (MgSO$_4$), filtered and concentrated in vacuo. Purification using an Isolute™ Si II cartridge, using a 0-10% MeOH in DCM gradient, gave a cream solid. Further purification using HPLC System 2, followed by isolation using an SCX-2 cartridge washed through with MeOH before product was recovered with 2M ammonia in MeOH, afforded the title compound as an off-white solid.

Yield: 17 mg (43%)

LC-MS (Method 3): Rt=8.53 min, m/z 906.28 [M+H]$^+$

Example 32

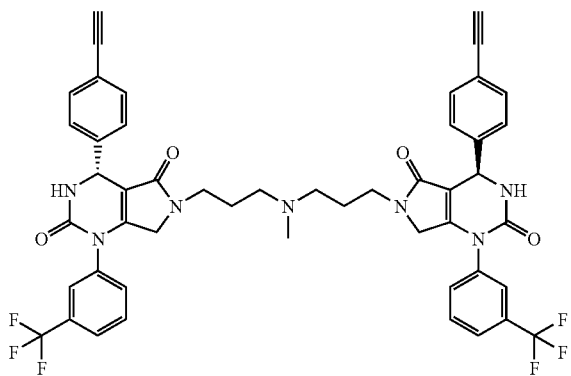

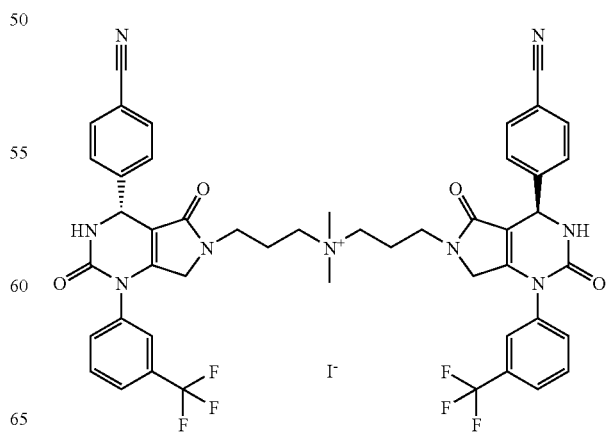

To a solution of Example 17 (50 mg, 0.055 mmol) in acetonitrile (2 ml) were added an excess of iodomethane (500 μL) and sodium hydrogen carbonate (14 mg, 0.16 mmol). The reaction mixture was stirred at RT for 18 h then evaporated in vacuo. The crude product was purified by HPLC System 1. The product containing fractions were combined and freeze dried.

Yield: 31 mg (54%)
LCMS (Method 3): m/z=922.08 [M]$^+$
1H NMR (400 MHz, DMSO-d6): δ=1.71 (br m, 4H); 2.82 (s, 6H); 2.99-3.30 (m, 8H); 3.81 (s, 4H); 5.40 (d, 2H); 7.61-7.90 (m, 16H); 8.21 (d, 2H) ppm.

The following examples were prepared using a similar procedure:

| | Structure | Precursor | Yield % | LC-MS Rt (min) | Mass [M]$^+$ |
|---|---|---|---|---|---|
| 33 | 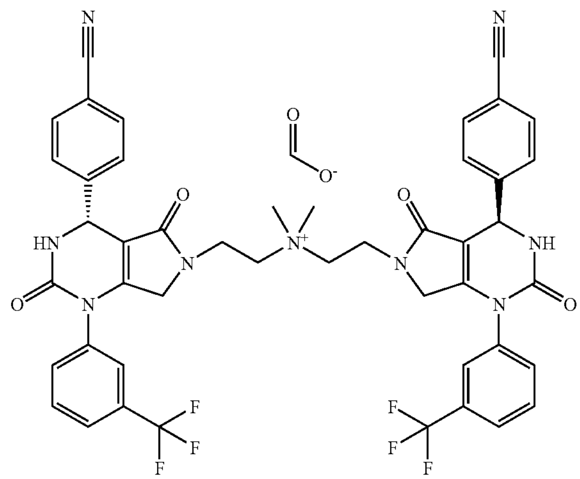 | Example 13 | 32 | 7.90 | 894.04 |
| 34 | 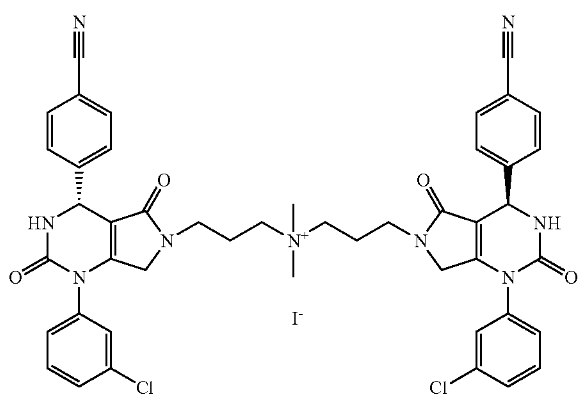 | Example 19 | 57 | 7.44 (Method 3) | 854.33 |
| 35 | 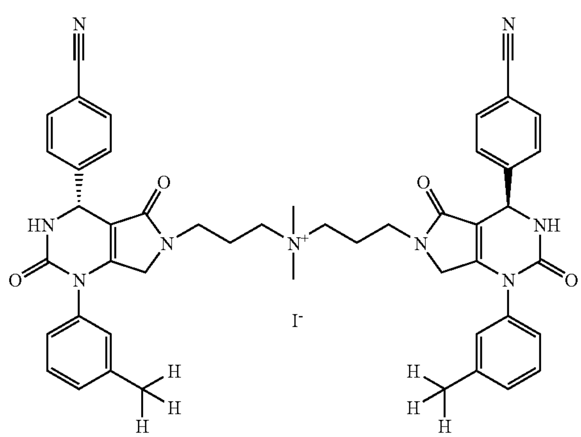 | Example 21 | 45 | 7.26 (Method 3) | 814.43 |

-continued
| | Structure | Precursor | Yield % | LC-MS Rt (min) | Mass [M]+ |
|---|---|---|---|---|---|
| 36 | 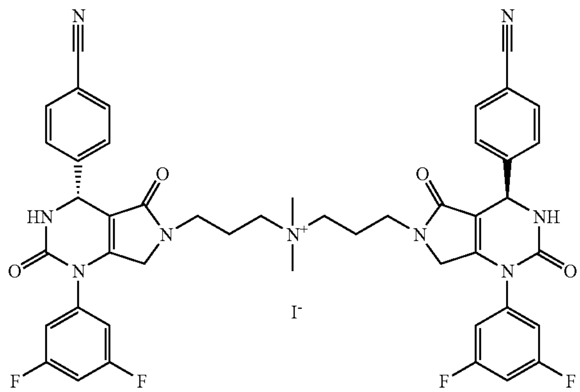 | Example 22 | 69 | 7.30 (Method 3) | 858.37 |
| 37 | 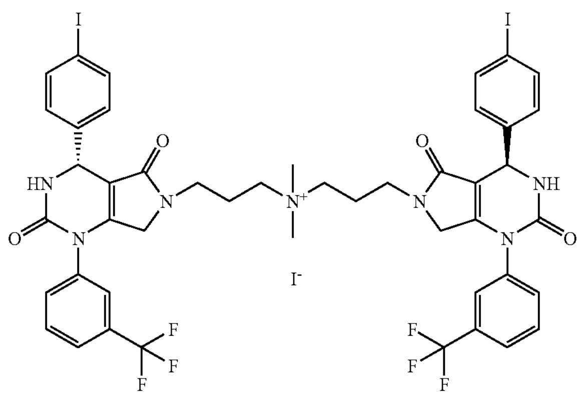 | Example 23 | 40 | 8.94 (Method 3) | 1124.18 |
Example 38
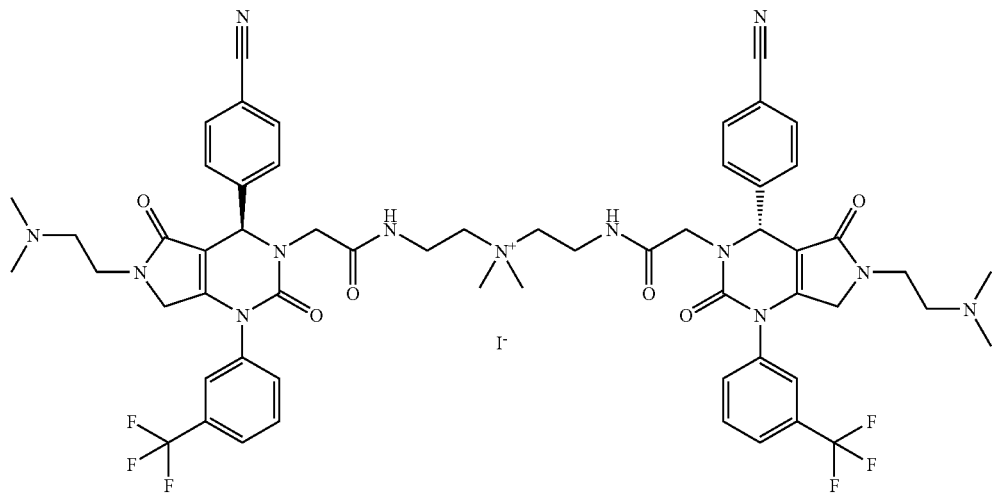

Intermediate 28 (347 mg, 0.256 mmol) and N,N-dimethylethylenediamine (135 mg, 1.536 mmol) were dissolved in acetonitrile (20 ml) and sodium hydrogen carbonate (193 mg, 2.30 mmol) was added. The reaction mixture was heated at 80° C. for 5 h after which time it was filtered and evaporated. The crude product was purified using HPLC System 1 and the pure fractions were combined and freeze-dried to give the bis-formate salt as a pale cream solid.

Yield: 45 mg (14%)

LC-MS (Method 3): Rt=5.81 min, m/z=575.79 $[M]^{2+}/2$

Example 39

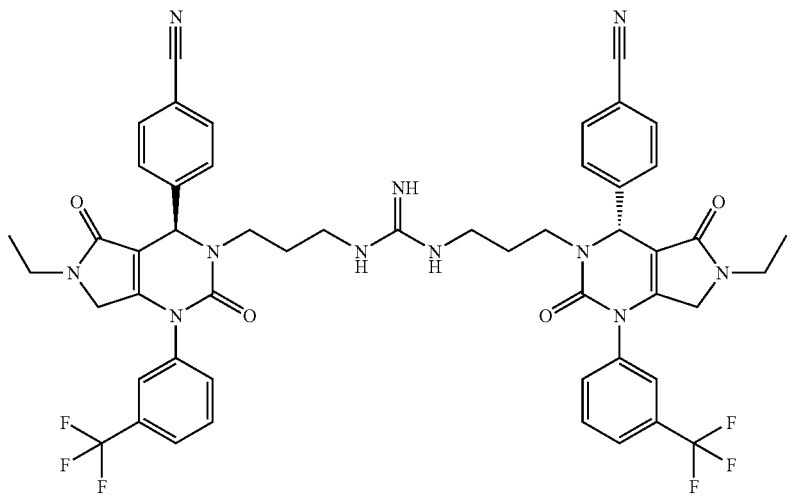

Intermediate 33 (155 mg, 0.154 mmol) was dissolved in IMS (20 ml) and iodomethane (4 ml) was added. The solution was allowed to stand at RT for 3 days. The volatiles were evaporated and the residue was re-dissolved in 2M ammonia in EtOH (7 ml). The reaction was heated at 50° C. for 48 h and concentrated, and the residue was purified using HPLC System 1 and freeze-dried to give the product as a white solid.

Yield: 35 mg (23%)

LC-MS (Method 3): Rt=9.44 min, m/z=992.04 $[M+H]^+$

Example 40

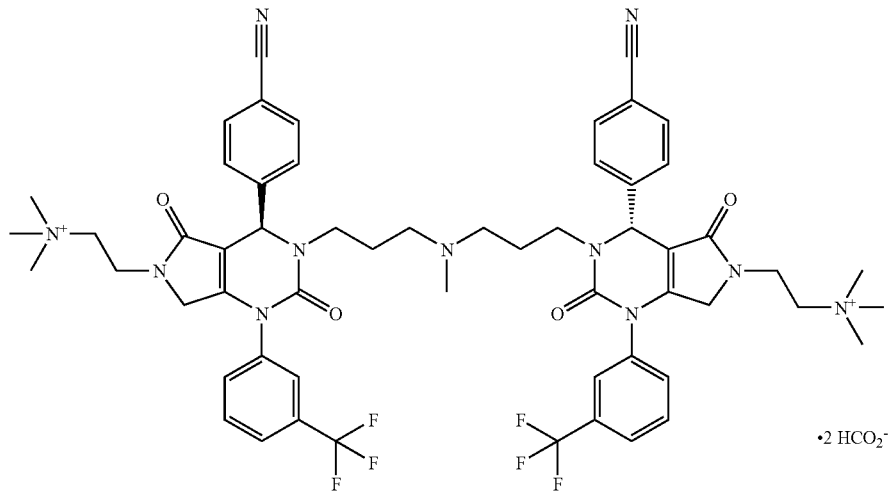

Example 40 was prepared from intermediate 24 and (2-aminoethyl)trimethylammonium chloride hydrochloride by a similar method to that used in the synthesis of Example 38. The crude product was purified using HPLC System 1 and freeze-dried to give a white solid.

Yield: (20%)
LC-MS (Method 3): Rt=6.17 min, m/z=539.86 [M]$^{2+}$/2

Example 41

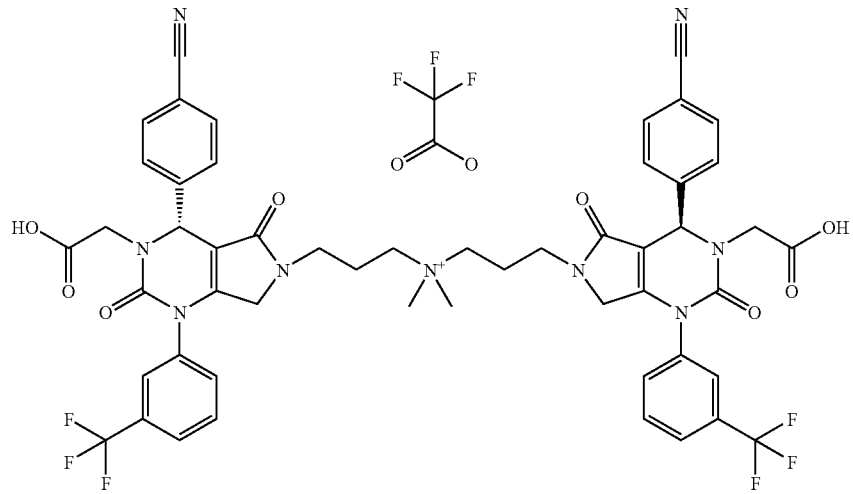

Intermediate 37 (175 mg, 0.137 mmol) was treated with a mixture of TFA (5 ml) and DCM (15 ml). The solution was allowed to stand at RT for 3 h and the volatiles were then evaporated. The residue was dissolved in a small amount of DCM and diethyl ether was added. The cream solid that precipitated was filtered and dried.

Yield: 150 mg (95%)
LC-MS (Method 3): Rt=8.39 min, m/z=1038.09 [M]$^+$

Example 42

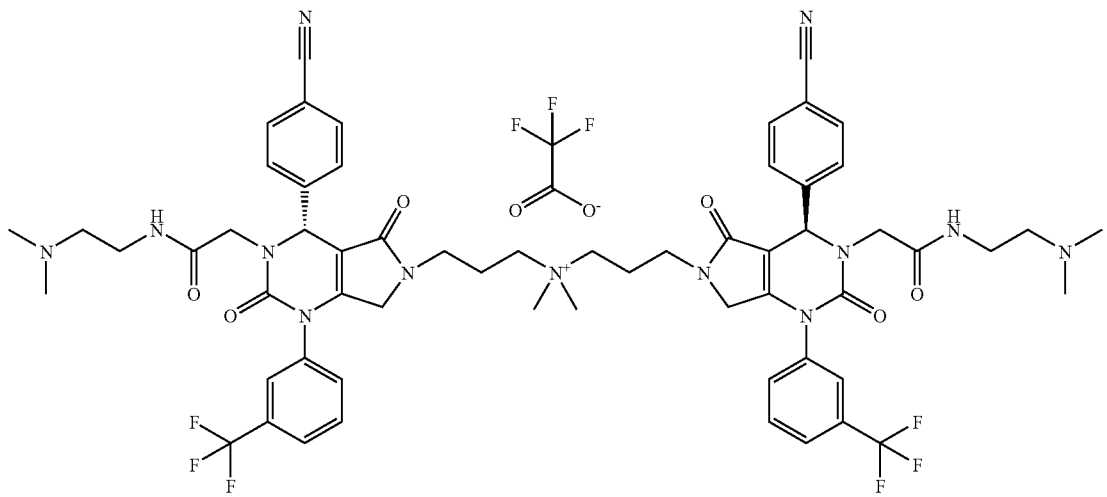

Example 41 (130 mg, 0.133 mmol), N,N-dimethylethylenediamine (30 mg, 0.399 mmol) and DIPEA (146 μl, 1.13 mmol) were dissolved in DMF (7 ml) and HATU (94 mg, 0.249 mmol) was added. The solution was allowed to stand at RT for 30 min and the DMF was evaporated. The residue was treated with sat. aqueous sodium hydrogen carbonate (100 ml) and extracted with DCM (3×80 ml). Evaporation of the organic extracts gave a pale yellow gum which was purified using HPLC System 1. The pure fractions were freeze-dried to give the bis-formate salt as a white solid.

Yield: 96 mg (61%)
LC-MS (Method 3): Rt=5.99 min, m/z=589.75 $[M]^{2+}/2$

Example 43

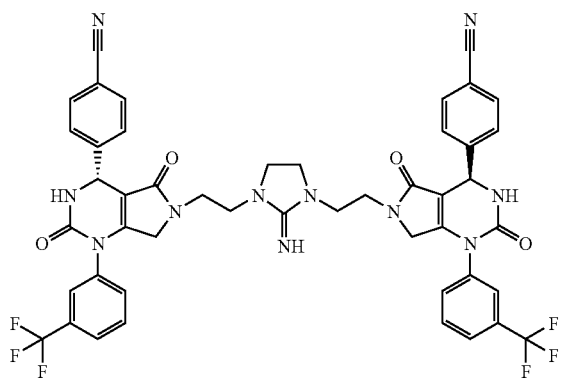

Example 43 was prepared from intermediate 40 using a procedure similar to that used in the synthesis of Example 39. The product was purified using HPLC System 1 and obtained as the formate salt.

Yield: (20%)
LC-MS (Method 3): Rt=8.03 min, m/z=934.47 $[M+H]^+$

Example 44

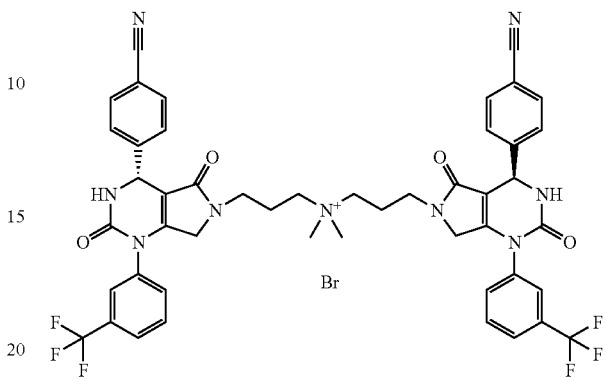

Example 17 (6.28 g, 6.92 mmol) was dissolved in acetonitrile (100 ml) and a 30% solution of bromomethane in acetonitrile (60 ml) was added. The solution was heated at 80° C. in a sealed metal tube. After 24 h the solvent was reduced to approximately half volume and then diluted with water. The solution was freeze-dried to give a cream solid.

Yield: quantitative
LC-MS (Method 3): Rt=7.92 min, m/z=922.37 $[M]^+$
1H NMR (400 MHz, DMSO-d6): δ=1.71 (br m, 4H); 2.82 (s, 6H); 2.99-3.30 (m, 8H); 3.81 (s, 4H); 5.40 (d, 2H); 7.61-7.90 (m, 16H); 8.21 (d, 2H) ppm.

The following examples were prepared in a similar manner:

| Structure | Precursor | Yield (%) | LC-MS Rt (min) | Mass $[M]^+$ |
|---|---|---|---|---|
| 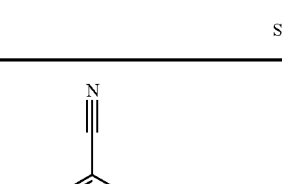 | Example 13 | 100 | 7.71 (Method 4) | 894.19 |

| | Structure | Precursor | Yield (%) | LC-MS Rt (min) | Mass [M]+ |
|---|---|---|---|---|---|
| 46 | 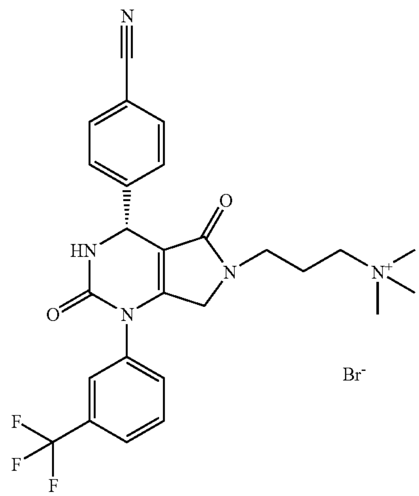 | Example 3 | 100 | 5.87 (Method 4) | 498.28 |
| 47 | 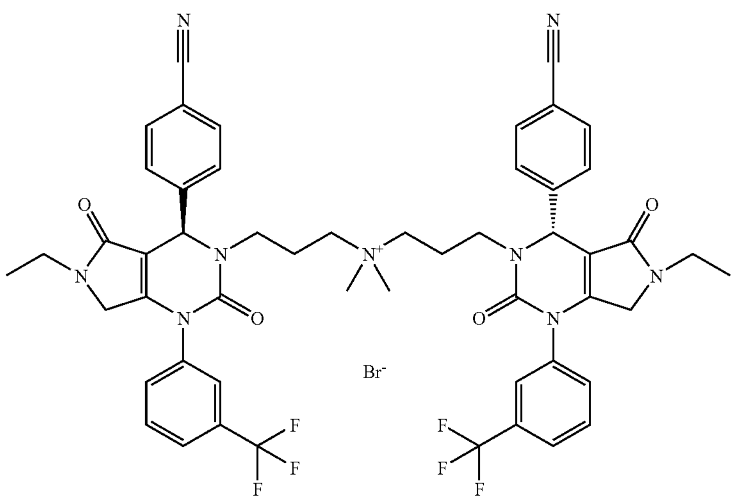 | Example 25 | 32 | 9.30 (Method 3) | 978.42 |

Example 48

Example 17 (150 mg, 0.165 mmol) and 2-bromoethanol (420 mg, 1.65 mmol) were dissolved in acetonitrile (2 ml) and the solution was heated at 80° C. for 120 h. The volatiles were evaporated and the product was purified using HPLC System 3. The pure fractions were combined and freeze-dried to give a cream solid.

Yield: 42 mg (25%)

LC-MS (Method 4): Rt=7.67 min, m/z=952.34 [M]+

The following examples were prepared using a similar procedure from Intermediate 17 and an alkyl halide:

| | Structure | Yield (%) | LC-MS Rt (min) (Method 4) | Mass [M + H]+ or [M]+ |
|---|---|---|---|---|
| 49 | 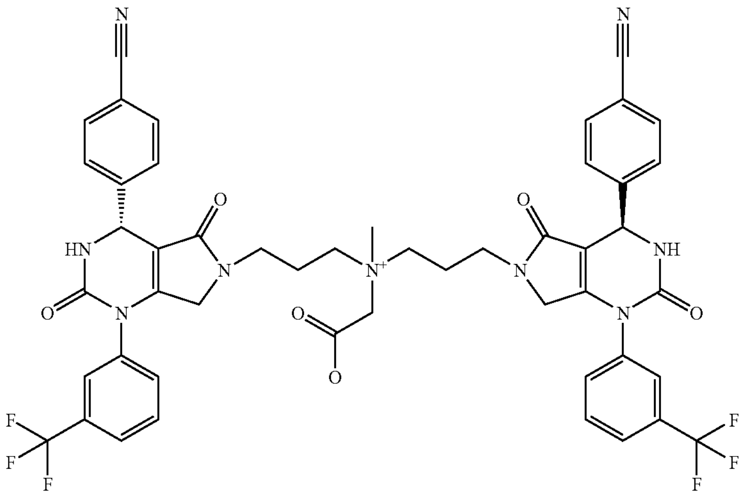 | 13 | 8.52 | 966.18 |
| 50 | 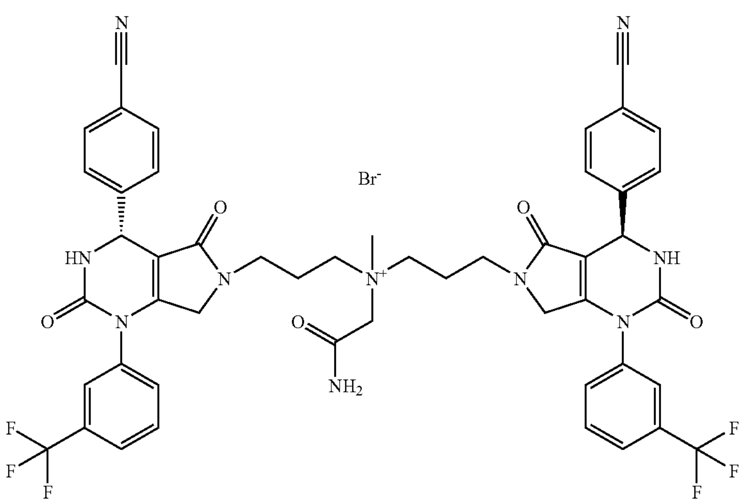 | 20 | 7.62 | 965.33 |

Example 51

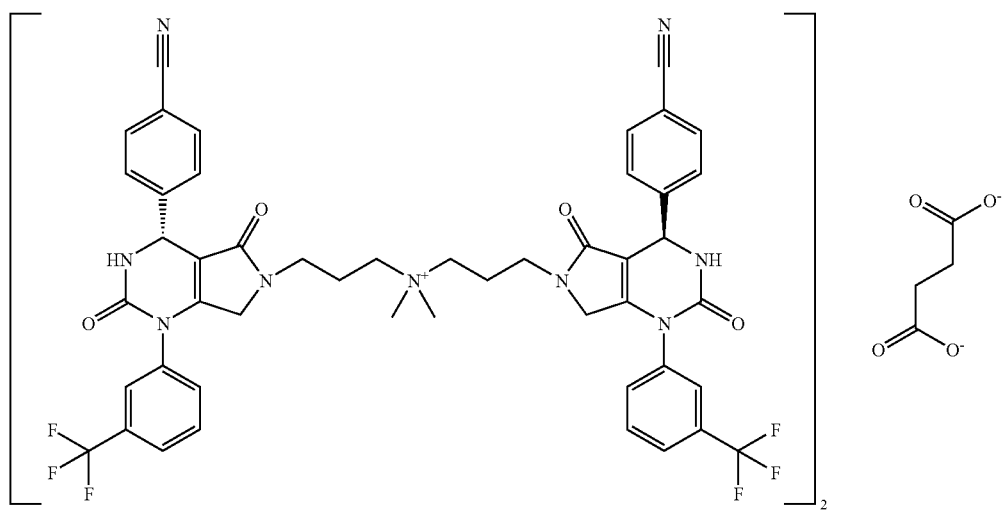

A solution of succinic acid (5.9 mg, 0.0499 mmol) in water (2 ml) was added to a tube containing silver (I) oxide (11.6 mg, 0.0499 mmol). The mixture was stirred in the dark for 17 h before a solution of Example 44 (100 mg, 0.0997 mmol) in THF (2 ml) and acetonitrile (0.5 ml) was added. Stirring was continued for 3 days and then the mixture was filtered. The filtrate was evaporated and the residue was purified by HPLC System 3. The pure fractions were combined and freeze-dried to give a pale yellow solid.

Yield: 29 mg (30%)

LC-MS (Method 4): Rt=7.70 min, m/z=922.33 [M]$^+$

1H NMR (400 MHz, MeOD): δ=1.84 (br m, 8H); 2.45 (4H, s); 2.92 (s, 12H); 3.14 (m, 8H); 3.30 (m, 8H); 3.91 (m, partly exchanged with solvent); 5.51 (s, 4H); 7.64-7.82 (m, 32H) ppm.

The following compounds were prepared in a similar manner:

| | Structure | Yield (%) | LC-MS Rt (min) | Mass [M + H]$^+$ |
|---|---|---|---|---|
| 52 | 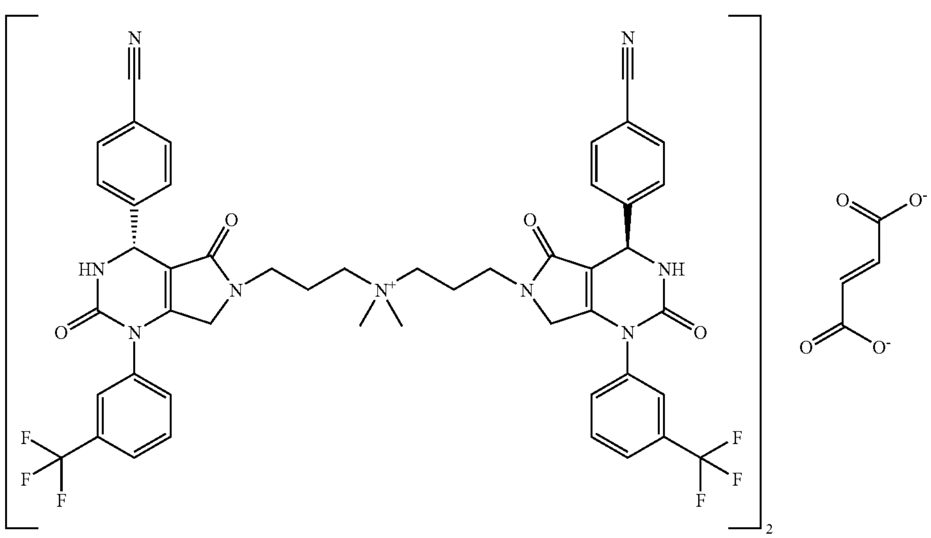 | 45 | 7.76 (Method 4) | 922.33 |

-continued

| | Structure | Yield (%) | LC-MS Rt (min) | Mass [M + H]+ |
|---|---|---|---|---|
| 53 | 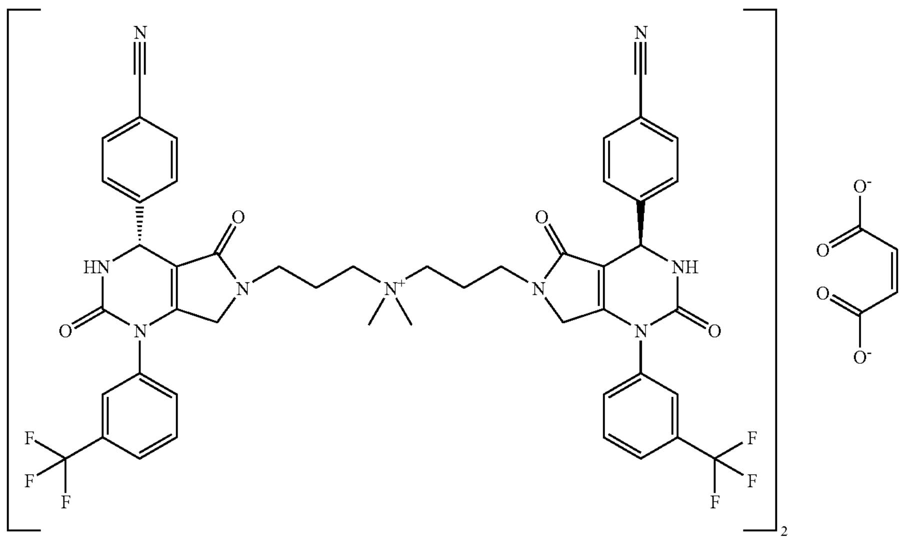 | 30 | 7.74 (Method 4) | 922.33 |
| 54 | 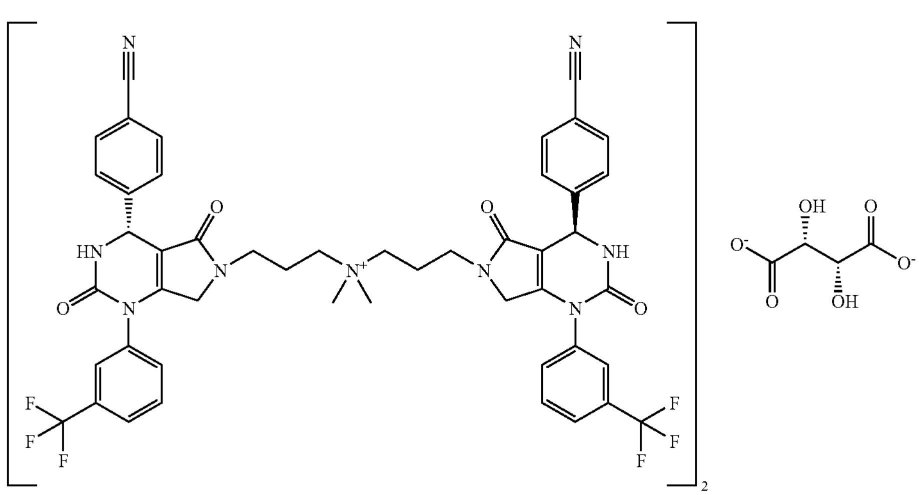 | 60 | 7.94 (Method 3) | 922.45 |

-continued

| | Structure | Yield (%) | LC-MS Rt (min) | Mass [M + H]+ |
|---|---|---|---|---|
| 55 | (bis-pyrrolo-pyrimidinedione ammonium structure with 4-cyanophenyl and 3-trifluoromethylphenyl substituents; naphthalene-1,5-disulfonate counterion) | 40 | 8.01 (Method 3) | 922.45 |
| 56 | (bis-pyrrolo-pyrimidinedione ammonium structure with 4-cyanophenyl and 3-trifluoromethylphenyl substituents; ethane-1,2-disulfonate counterion) | 52 | 8.08 (Method 3) | 922.45 |

NMR data:

Example 52

1H NMR (400 MHz, MeOD): δ=1.84 (br m, 8H); 2.92 (s, 12H); 3.14 (m, 8H); 3.30 (m, 8H); 3.91 (m, partly exchanged with solvent); 5.51 (s, 4H); 6.60 (2H, s); 7.64-7.82 (m, 32H) ppm.

Example 53

1H NMR (400 MHz, MeOD): δ=1.84 (br m, 8H); 2.92 (s, 12H); 3.14 (m, 8H); 3.30 (m, 8H); 3.91 (m, partly exchanged with solvent); 5.51 (s, 4H); 6.18 (2H, s); 7.64-7.82 (m, 32H) ppm.

Example 54

1H NMR (400 MHz, MeOD): δ=1.84 (br m, 8H); 2.92 (s, 12H); 3.14 (m, 8H); 3.30 (m, 8H); 3.91 (m, partly exchanged with solvent); 4.22 (2H, s); 5.51 (s, 4H); 7.64-7.82 (m, 32H) ppm.

Example 55

1H NMR (400 MHz, DMSO-d6): δ=1.71 (br m, 8H); 2.82 (s, 12H); 2.99-3.30 (m, 16H); 3.81 (s, 8H); 5.40 (d, 4H); 7.34 (dd, 2H); 7.61-7.90 (m, 16H); 8.12 (m, 4H); 8.81 (d, 2H) ppm.

Example 56

1H NMR (400 MHz, DMSO-d6): δ=1.71 (br m, 8H); 2.56 (s, 4H); 2.82 (s, 12H); 2.99-3.30 (m, 16H); 3.81 (s, 8H); 5.40 (d, 4H); 7.61-7.90 (m, 32H); 8.21 (d, 4H) ppm.

Example 57

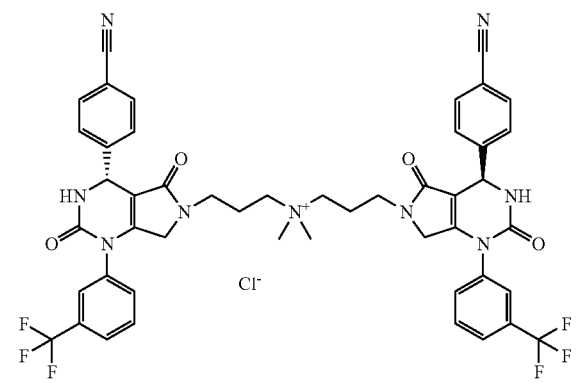

Example 44 (100 mg, 0.0997 mmol) was dissolved in MeOH (50 ml) and loaded onto an Isolute™ SCX-2 cartridge which had been conditioned with MeOH. The cartridge was flushed with MeOH and then the product was eluted with 1.25M HCl in MeOH (60 ml). The solvent was evaporated and the product was purified using HPLC System 3. The pure fractions were combined and freeze-dried to give a white solid.

Yield: 35 mg (37%)
LC-MS (Method 4): Rt=7.72 min, m/z=922.22 [M]$^+$

Example 58

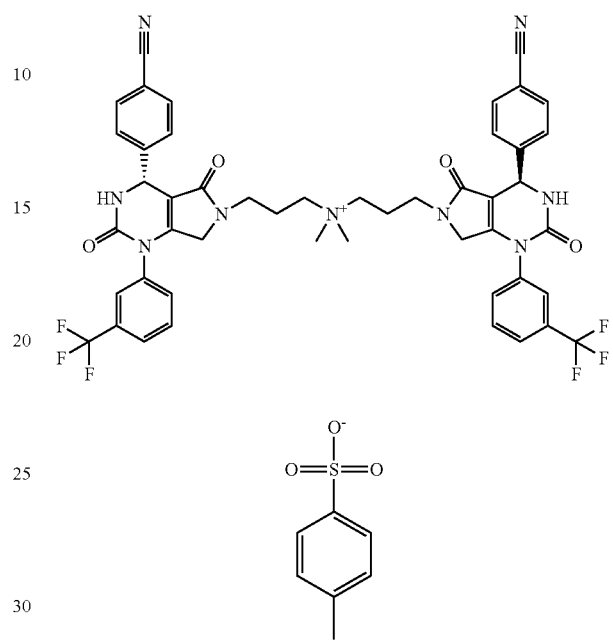

Example 57 (956 mg, 0.998 mmol) was dissolved in acetonitrile (20 ml) and sodium tosylate (290 mg, 1.50 mmol) was added. The reaction mixture was heated at 80° C. under argon for 17 h. After cooling, the solid was filtered off and the filtrate was evaporated. The product was purified on an Isolute™ Al—N cartridge (10 g) eluting with 0-6% MeOH in DCM, and obtained as a cream solid.

Yield: 5.03 (46%)
LC-MS ((Method 3): Rt=7.97 min, m/z=922.38 [M]$^+$
1H NMR (400 MHz, DMSO-d6): δ=1.71 (br m, 4H); 2.24 (s, 3H); 2.82 (s, 6H); 2.99-3.30 (m, 8H); 3.81 (s, 4H); 5.40 (d, 2H); 7.10 (d, 2H); 7.43 (d, 2H); 7.61-7.90 (m, 16H); 8.21 (d, 2H) ppm.

Example 59

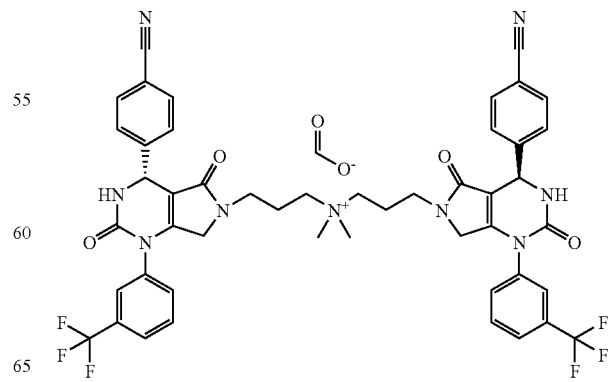

Example 32 was passed through HPLC System 5. The pure fractions were combined and freeze-dried to give an off-white solid.

LC-MS (Method 3): Rt=7.86 min, m/z=922.15 [M]⁺

1H NMR (400 MHz, DMSO-d6): δ=1.71 (br m, 4H); 2.82 (s, 6H); 2.99-3.30 (m, 8H); 3.81 (s, 4H); 5.40 (d, 2H); 7.61-7.90 (m, 16H); 8.21 (d, 2H); 8.27 (s, 1H) ppm.

Example 60

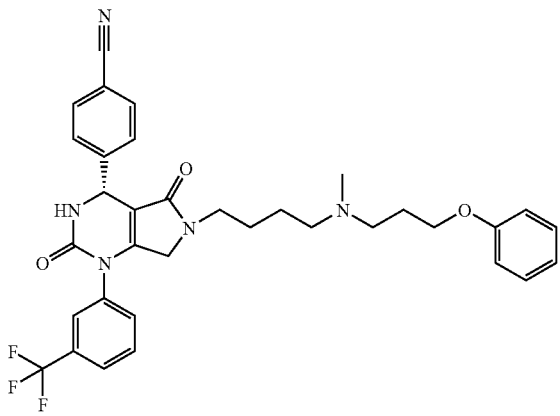

Example 60 was prepared from Intermediate 43 using a method similar to that used in the synthesis of Intermediate 45.

Yield: (36%)

LC-MS (Method 4): Rt=7.49 min, m/z=618.34 [M+H]⁺

Example 61

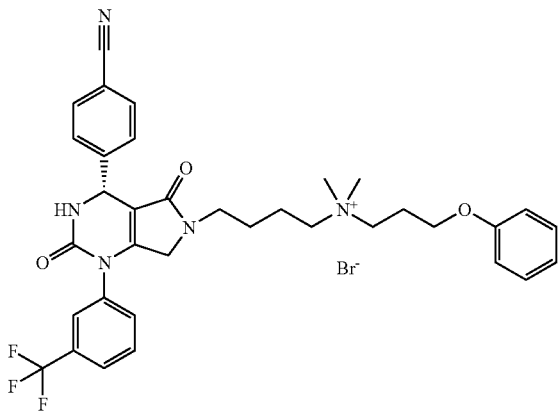

Example 61 prepared from Example 60 using a procedure similar to that used in the synthesis of Example 44.

Yield: quantitative

LC-MS (Method 3): Rt=7.87 min, m/z=632.29 [M]⁺

Example 62

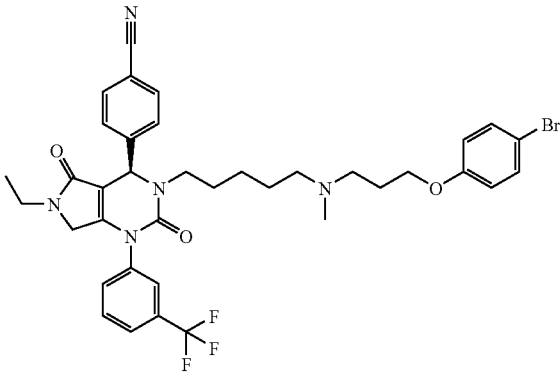

A solution of Intermediate 46 (124 mg, 0.151 mmol) in acetonitrile (6 ml) was treated with a 2M solution of ethylamine in THF (755 μl, 1.51 mmol). The solution was allowed to stand at RT for 17 h. Evaporation of the solvent gave a residue which was purified using HPLC System 2.

Yield: 24 mg (48%)

LC-MS (Method 4): Rt=8.74 min, m/z=738.35/740.30 [M+H]⁺

Example 63

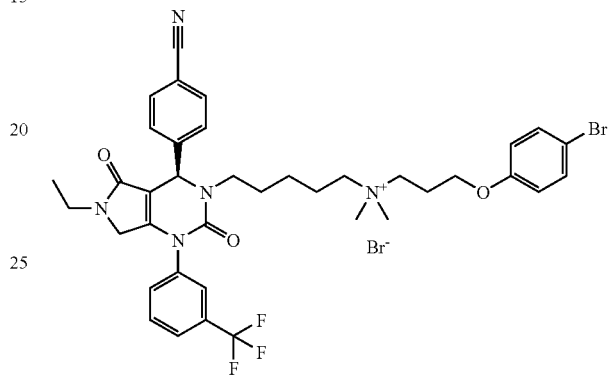

Example 63 was prepared from Example 62 using a method analogous to that used in the preparation of Example 44.

Yield: quantitative

LC-MS (Method 3): Rt=9.11 min, m/z=752.31/754.31 [M]⁺

Example 64

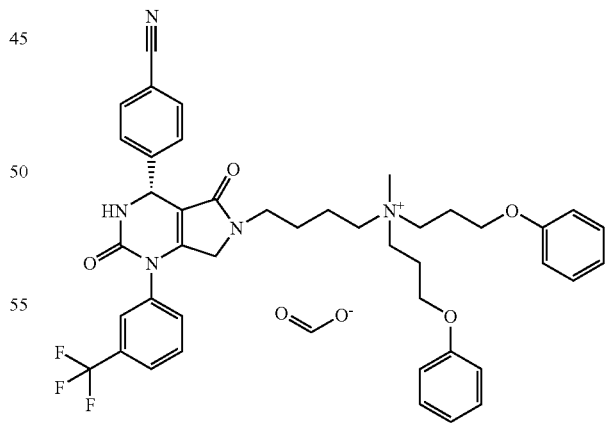

Example 64 was obtained during the synthesis of Example 60. Exchange of the counterion occurred during HPLC (System 2).

Yield: (9%)

LC-MS (Method 4): Rt=8.72 min, m/z=752.46 [M]⁺

Example 65

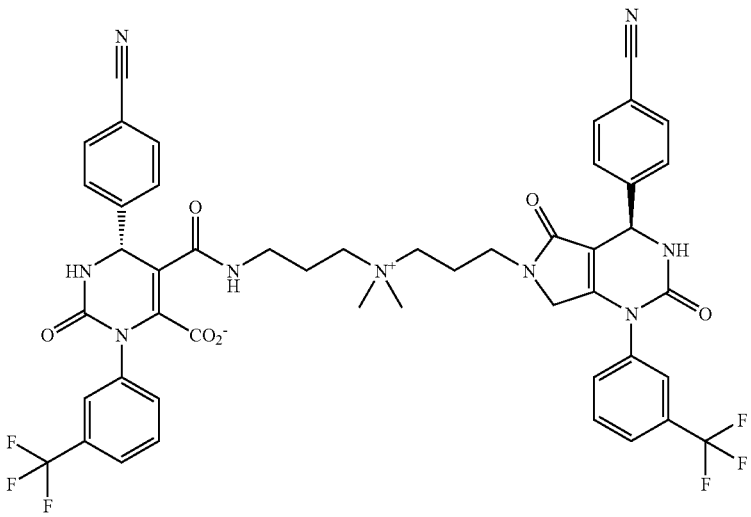

A solution of Example 44 (50 mg, 0.0499 mmol) in water (1 ml) and THF (1 ml) was treated with silver (I) oxide (5.76 mg, 0.0248 mmol). After 18 h, the mixture was filtered and the filtrate was treated with succinic acid (2.94 mg, 0.0248 mmol). After 1 h the mixture was purified using HPLC System 4. The product was obtained a white solid.

Yield: 10 mg (20%)

LC-MS (Method 4): Rt=3.19 min, m/z=954.19 [M+H]$^+$

Example 66

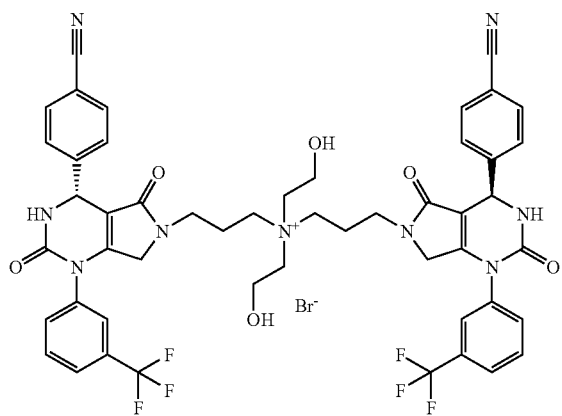

Example 18 (30 mg, 0.0335 mmol) and 2-bromoethanol (92 mg, 0.774 mmol) were dissolved in acetonitrile (5 ml) in the presence of sodium carbonate (62 mg, 0.774 mmol) and the reaction mixture was heated at 80° C. for 48 h under stirring. The suspension was filtered and concentrated and the residue purified using HPLC System 3. The fractions containing the product were combined and freeze dried to afford a white fluffy powder.

Yield: 14 mg (39%)

LC-MS (Method 3): Rt=7.84 min, m/z=982.42 [M$^+$]

Example 67

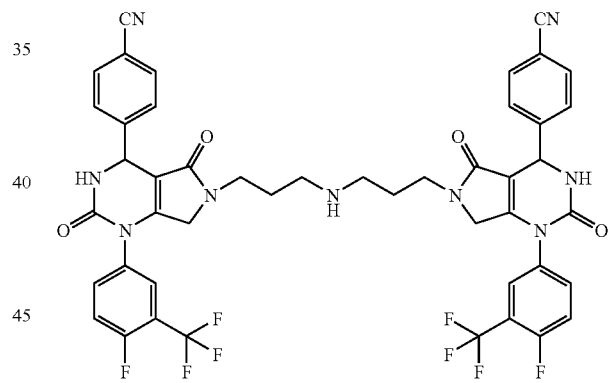

A solution of Intermediate 48 (0.45 g, 0.88 mmol) in anhydrous THF (10 ml) was added dropwise to a solution of N-(3-aminopropyl)-1,3-propanediamine (0.115 g, 0.88 mmol) and triethylamine (0.356 g, 3.52 mmol) in anhydrous THF (5 ml) at room temperature with stirring. After 2 h, the volatiles were removed under reduced pressure and the residue partitioned between water and ethyl acetate. The organic layer was separated, washed with water and brine, dried (Na$_2$SO$_4$) and evaporated. The crude product was purified on an Isolute® SPE Si II cartridge (5 g) eluting with DCM, 10% MeOH in DCM and then 18% MeOH in DCM. Pure fractions were combined and the solvent removed under reduced pressure. The residue was dissolved in 1:1 MeCN/H$_2$O (10 ml) and then freeze-dried to give the desired product as a white solid.

Yield: 0.122 g, 30%.
LC-MS (Method 6): Rt=8.09 min, m/z=930 [M+H]⁺

Example 68

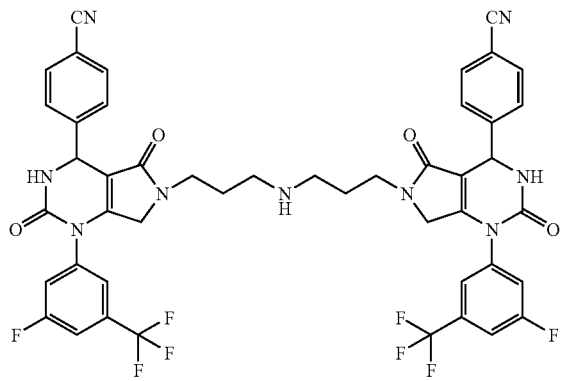

Example 68 was prepared from Intermediate 50 using a similar procedure to that used in the synthesis of Example 67.
Yield: 0.151 g, 28%
LC-MS (Method 6): Rt=8.15 min, m/z=930 [M+H]⁺

Example 69

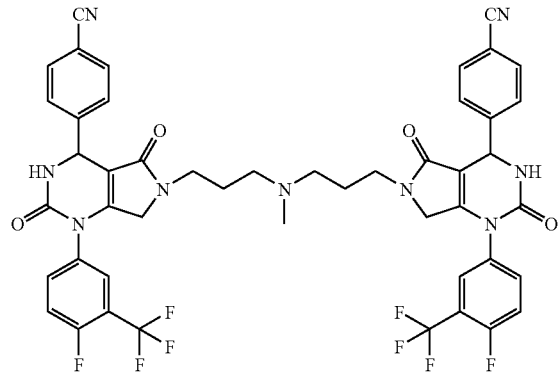

Example 69 was prepared from Intermediate 48 (1.50 g, 2.93 mmol) and 3,3'-diamino-N-methyldipropylamine (0.319 g, 2.20 mmol), using a similar procedure to that employed in the synthesis of Example 67.
Yield: 1.25 g, 90%
LC-MS (Method 6): Rt=8.15 min, m/z=944 [M+H]⁺

Example 70

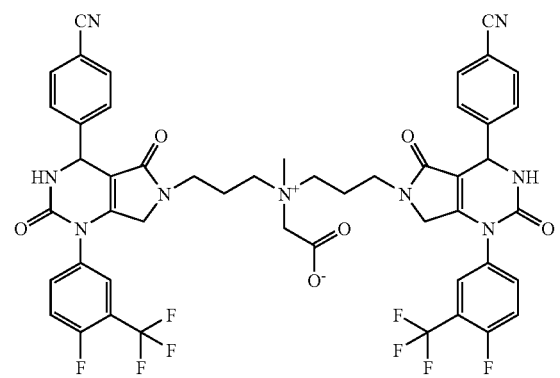

TFA (5 ml) was added to a solution of Intermediate 51 (0.34 g, 0.30 mmol) in DCM (8 ml) at RT with stirring. After 20 h the volatiles were evaporated. The residue was partitioned between sat. aqueous sodium hydrogen carbonate and ethyl acetate. The organic layer washed with brine, dried (Na₂SO₄) and evaporated. The crude material was purified by HPLC (System 1) and after freeze-dry, the desired product was obtained as a white solid.
Yield: 155 mg, 55%
LC-MS (Method 6): Rt=9.14 min, m/z=1002 [M+H]⁺

Example 71

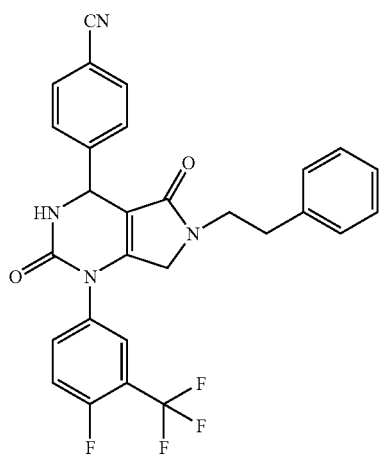

A solution of 2-phenylethylamine (52 mg, 0.43 mmol) and triethylamine (87 mg, 0.86 mmol) in anhydrous THF (3 ml) was added to a solution of Intermediate 48 (200 mg, 0.39 mmol) in anhydrous THF (5 ml) at room temperature with stirring. After 20 h, the volatiles were removed under reduced pressure and the residue partitioned between 1N aqueous HCl and ethyl acetate. The organic layer was separated, washed with water, brine, dried (Na₂SO₄) and evaporated. The crude product was purified on an Isolute® SPE Si II cartridge (5 g) eluting with DCM, 20% EtOAc in DCM and 5% MeOH in DCM. Pure fractions were combined and the solvent removed under reduced pressure to give the desired product as a white solid.
Yield: 197 mg, 97%.
LC-MS (Method 6): Rt=11.02 min, m/z=521 [M+H]⁺

Example 72

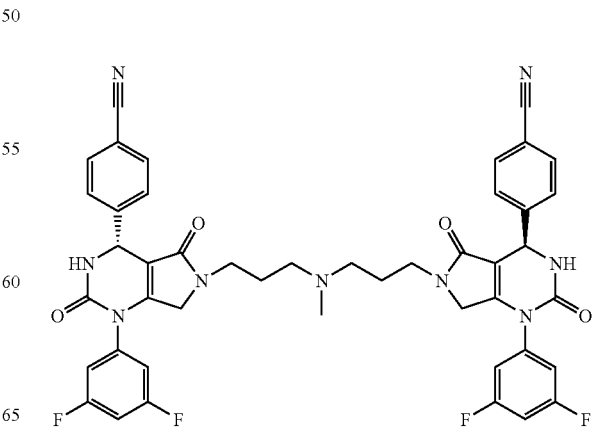

By analogy to the procedure of Example 8 of WO2007/129060, and using Intermediate 20 therein as precursor, the above compound was prepared; yield 59%; LC-MS 7.36 (Method 3 in that WO publication); mass 844.51.

Example 73

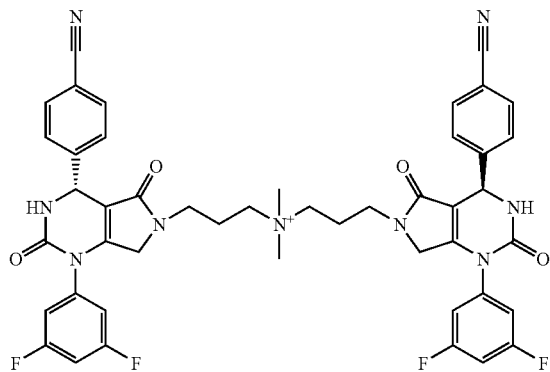

By analogy to the procedure of Example 32 of WO2007/129060, and using the compound of Example 6 as precursor, the above compound was prepared; yield 69%; LC-MS 7.30 (Method 3 in that WO publication); mass 858.37.

Biological Assays

Compounds of the invention were tested for their HNE inhibitory activity.

Fluorescent Peptide Substrate

Assays were performed in 96-well plates at a total assay volume of 100 μl. The final concentration of the enzyme (human leukocyte elastase, Sigma E8140) was 0.00036 units/well. A peptide substrate (MeO-Suc-Ala-Ala-Pro-ValAMC, Calbiochem #324745) was used, at the final concentration of 100 μM. The final concentration of DMSO was 1% in the assay buffer (0.05M Tris.HCl, pH 7.5, 0.1M NaCl; 0.1M CaCl2; 0.0005% brij-35).

The enzymatic reaction was started by adding the enzyme. The enzymatic reaction was performed at RT and after 30 mins stopped by adding 50 μl soybean trypsin inhibitor (Sigma T-9003) at a final concentration of 50 μg/well. Fluorescence was read on the FLEXstation (Molecular Devices) using 380 nm excitation and 460 nm emission filters. The potency of the compounds was determined from a concentration series of 10 concentrations in range from 1000 nM to 0.051 nM. The results are means of two independent experiments, each performed in duplicate.

Using Fluorescently Labelled Elastin

Assays were performed in 96-well plate at a total assay volume of 100 μl. The final concentration of the enzyme (human leukocyte elastase, Sigma E8140) was 0.002 units/well. Fluorescently labelled, solubilised elastin from bovine neck ligament (Molecular Probes, E-12056) was used at the final concentration of 15 μg/ml. The final concentration of DMSO was 2.5% in the assay buffer (0.1M Tris-HCL, pH8.0, containing 0.2 mM sodium azide).

The enzymatic reaction was started by adding the enzyme. The enzymatic reaction was performed at RT and read after 120 minutes. Fluorescence was read on the FLEXstation (Molecular Devices) using 485 nm excitation and 530 nm emission filters. The potency of the compounds was determined from a concentration series of 10 concentrations in range from 25000 nM to 1 nM. The results are means of two independent experiments, each performed in duplicate.

All compounds of the Examples except Example 23 had IC50 values of less than 100 nm. Example 23 had an activity in the range 50-500 nm.

HNE Induced Lung Haemorrhage in the Rat

Instillation of human neutrophil elastase (HNE) into rat lung causes acute lung damage. The extent of this injury can be assessed by measuring lung haemorrhage. Male Sprague Dawley rats (175-220 g) were obtained from Harlan UK Ltd., full barrier-bred and certified free from specified micro-organisms on receipt. Animals were weighed and randomly assigned to treatment groups (7-12 animals per group).

The vehicle used was 1% DMSO/Saline. Inhibitors were dissolved in 1% DMSO before the addition of 0.9% saline.

Animals in each study used to determine the efficacy of the elastase inhibitors delivered locally to the lung by a variety of routes. Rats were anaesthetised with the inhaled anaesthetic Isoflurane (4%) when the dose was given from 30 minutes to 6 h prior to human neutrophil elastase (HNE) administration or terminally anaesthetised with hypnorm:hypnovel:water (1.5:1:2 at 2.7 ml/kg) when the predose was given at less than 30 minutes prior to HNE administration and dosed either intratracheally (i.t.) by transoral administration using a Penn Century microsprayer or intranasally (i.n.) by dropping the fluid on to the nares. Animals either received vehicle or compound at a dose volume of 0.5 ml/kg.

Animals that had been allowed to recover after dosing were terminally anaesthetised with hypnorm:hypnovel:water (1.5:1:2 at 2.7 ml/kg). Once sufficiently anaesthetised, HNE (600 units/ml) or sterile saline was administered by transoral tracheal instillation at a volume of 100 μl using a Penn Century microsprayer. Animals were kept warm in a temperature controlled box and given top up doses of anaesthetic as required to ensure continuous anaesthesia until termination.

Animals were sacrificed (0.5 ml to 1 ml sodium pentobarbitone) one hour post HNE challenge. The trachea was exposed and a small incision made between two tracheal rings allowing a cannula (10 gauge, O.D. 2-10 mm, Portex Ltd.) to be inserted approximately 2 cm into the trachea towards the lung. This was secured into place with a cotton ligature. The lungs were then lavaged (BAL) three times with fresh 4 ml aliquots of heparinised (10 units/ml) phosphate buffered saline (PBS). The resultant BALF was kept on ice until it was centrifuged.

The BALF was centrifuged at 1000 r.p.m. for 10 minutes in a centrifuge cooled to between 4 and 10° C. The supernatant was discarded and the cell pellet resuspended in 1 ml 0.1% CETAB/PBS to lyse the cells. Cell lysates were frozen until spectrophotometric analysis for blood content could be made. Standards were prepared by making solutions of whole rat blood in 0.1% CETAB/PBS.

Once defrosted 100 μl of each lysed cell suspension was placed into a separate well of a 96 well flat bottomed plate. All samples were tested in duplicate and 100 μl 0.1% CETAB/PBS was included on the plate as a blank. The OD of the contents of each well was measured at 415 nm using a spectramax 250 (Molecular devices).

A standard curve was constructed by measuring the OD (at 415 nm) of different concentrations of blood in 0.1% CETAB/PBS (30, 10, 7, 3, 1, 0.3, 0.1 μl/ml).

The amount of blood in each experimental sample was calculated by comparison to the standard curve. Data were then analysed as below:
1) The mean OD for duplicates was calculated
2) The value for the blank was subtracted from the value for all other samples 3) Data were assessed to evaluate the normality of distribution.

The compounds of Examples 17, 18, 26, 27, 30, 32, 40, 41, 42, 43, 49, 59, 61 and 64 were tested in the above assay and were shown to be effective in reducing the quantity of blood haemorrhaged relative to control. For example, the compound of Example 32 showed a statistically significant reduction in haemorrhage of 67% relative to control when administered at 30 mg/kg it, 1 hour prior to HNE.

We claim:

1. A compound of formula (I):

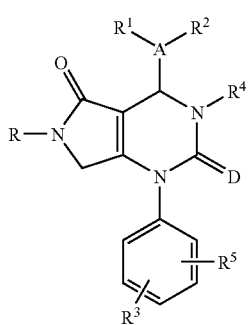

(I)

wherein
- A is selected from the group consisting of aryl and heteroaryl;
- D is selected from the group consisting of oxygen and sulphur;
- $R^1$, $R^2$, and $R^3$ are independently each selected from the group consisting of hydrogen, halogen, nitro, cyano, $C_1$-$C_6$-alkyl, $C_2$-$C_6$-alkenyl, $C_2$-$C_6$-alkynyl, hydroxyl, $C_1$-$C_6$-alkoxy and $C_2$-$C_6$-alkenyloxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy;
- $R^5$ is hydrogen;
- R and $R^4$ each independently represent a radical of formula —[X]$_m$—[Alk$^1$]$_p$-[Q]$_n$-[Alk$^2$]$_q$—[X$^1$]$_k$—Z wherein
- k, m, n, p and q are independently selected from 0 and 1;
- Alk$^1$ and Alk$^2$ each independently represent an optionally substituted $C_1$-$C_6$ alkylene or $C_2$-$C_6$ alkenylene radical which may optionally contain an ether (—O—), thioether (—S—) or amino (—NR$^A$—) link;
- Q represents (i) a divalent radical selected from the group consisting of —O—, —S—, —S(=O)—, —S(=O)$_2$—, —S$^+$(R$^A$)—, —N(R$^A$)—, —N$^+$(R$^A$)(R$^B$)—, —C(=O)—, —C(=O)O—, —OC(=O)—, —C(=O)NR$^A$—, —NR$^A$C(=O)—, —S(O$_2$)NR$^A$—, —NR$^A$S(O$_2$)—, —NR$^A$C(=O)NR$^B$—, —NR$^A$C(=NR$^A$)NR$^B$—, —C(=NR$^D$)NR$^E$—, and —NR$^E$C(=NR$^D$)—, wherein R$^A$, R$^B$, R$^D$ and R$^E$ are independently, selected from the group consisting of hydrogen, $C_1$-$C_6$ alkyl and $C_3$-$C_6$ cycloalkyl, or R$^A$ and R$^B$, or R$^D$ and R$^E$ taken together with the nitrogen to which they are attached form a monocyclic heterocyclic ring of 5 to 7 ring atoms which may contain a further heteroatom selected from N, O and S, or (ii) an optionally substituted divalent mono- or bicyclic carbocyclic or heterocyclic radical having 3-6 ring members;
- X represents a divalent radical selected from the group consisting of —(C=O)—, —S(O$_2$)—, —C(=O)O—, —(C=O)NR$^A$— and —S(O$_2$)NR$^A$—, wherein
- X$^1$ is selected from the group consisting of —O—, —S— and —NH—; and
- Z is hydrogen or an optionally substituted mono- or bicyclic carbocyclic or heterocyclic radical having 3-6 ring members; or a pharmaceutically acceptable salt thereof.

2. The compound as claimed in claim 1 wherein A is selected from the group consisting of phenyl, pyridyl and pyrimidinyl.

3. The compound as claimed in claim 1 wherein one of $R^1$ and $R^2$ is selected from the group consisting of methyl, —C≡CH and cyano.

4. The compound as claimed in claim 1 wherein —AR$^1$R$^2$ is selected from the group consisting of 4-cyanophenyl and 4-ethynylphenyl.

5. The compound as claimed in claim 1 wherein D is O.

6. The compound as claimed in claim 1 wherein $R^3$ is selected from the group consisting of H, CF$_3$, F, Cl and Br.

7. The compound as claimed in claim 1 wherein $R^4$ and/or R is a radical of formula —[X]$_m$—[Alk$^1$]$_p$-[Q]$_n$-[Alk$^2$]$_q$—[X$^1$]$_k$—Z wherein m is 0; k, p, n and q are each 1; Q is —N(R$^A$) or —N$^+$(R$^A$)(R$^B$)—; and R$^A$, R$^B$, Alk$^1$, Alk$^2$, X$^1$ and Z are as defined in claim 1.

8. The compound as claimed in claim 7 wherein X$^1$ is —O—.

9. The compound as claimed in claim 1 wherein one of R and $R^4$ is hydrogen.

10. The compound as claimed in claim 1 wherein R or $R^4$ is selected from the group consisting of $C_1$-$C_6$-alkyl, formyl, aminocarbonyl, mono- or di-$C_1$-$C_4$-alkylaminocarbonyl, $C_3$-$C_8$-cycloalkylcarbonyl, $C_1$-$C_6$-alkylcarbonyl, $C_1$-$C_6$-alkoxycarbonyl, N—($C_1$-$C_4$-alkylsulfonyl)-aminocarbonyl, N—($C_1$-$C_4$-alkylsulfonyl)-N—($C_1$-$C_4$-alkyl)-aminocarbonyl, heteroaryl, heterocycloalkyl, heteroarylcarbonyl and heterocycloalkylcarbonyl; wherein $C_1$-$C_6$-alkyl, mono- and di-$C_1$-$C_4$-alkylaminocarbonyl, $C_1$-$C_6$-alkylcarbonyl, $C_1$-$C_6$-alkoxycarbonyl, heteroaryl and heterocycloalkyl can be substituted with one to three identical or different radicals selected from the group consisting of aryl, heteroaryl, hydroxyl, $C_1$-$C_4$-alkoxy, hydroxycarbonyl, $C_1$-$C_6$-alkoxycarbonyl, aminocarbonyl, mono and di-$C_1$-$C_4$-alkylaminocarbonyl, amino, mono- and di-$C_1$-$C_4$-alkylamino $C_1$-$C_4$-alkylcarbonylamino, cyano, N-(mono- and di-$C_1$-$C_4$-alkylamino-$C_1$-$C_4$-alkyl)-aminocarbonyl, N—($C_1$-$C_4$-alkoxy-$C_1$-$C_4$-alkyl)-aminocarbonyl and halogen.

11. The compound as claimed in claim 1 wherein R and/or $R^4$ represents a group of Formula (VIIIA), (VIIIB) or (VIIIC):

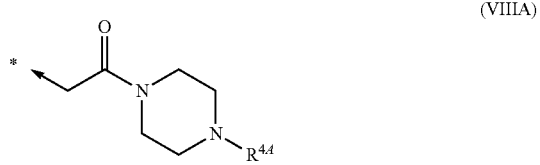

(VIIIA)

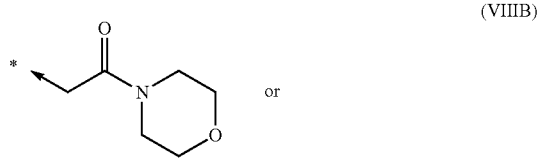

(VIIIB)

or

111
-continued

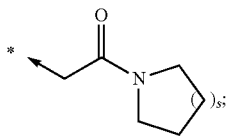

(VIIIC)

wherein $R^{4A}$ is hydrogen or $C_1$-$C_6$-alkyl, and s is 1 or 2.

12. The compound as claimed in claim 1 wherein R and/or $R^4$ represents a group of Formula (IX)

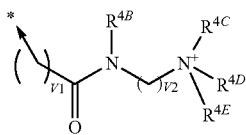

(IX)

wherein
$R^{4B}$ is hydrogen or $C_1$-$C_6$-alkyl;
$R^{4C}$, $R^{4D}$, $R^{4E}$ are each $C_1$-$C_6$-alkyl, and the nitrogen to which they are attached is quaternary and carries a positive charge; and additionally any two of $R^{4C}$, $R^{4D}$, $R^{4E}$ may be joined to form a ring, optionally containing a second heteroatom selected from oxygen or nitrogen; or one of $R^{4C}$, $R^{4D}$, $R^{4E}$ is a lone pair and the other groups are as defined above, and the nitrogen to which they are attached is tertiary; and
v1 and v2 are each independently 0-5.

13. The compound as claimed in claim 1 wherein R and/or $R^4$ represents a group selected from the following:

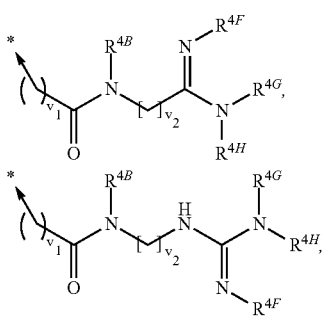

112
-continued

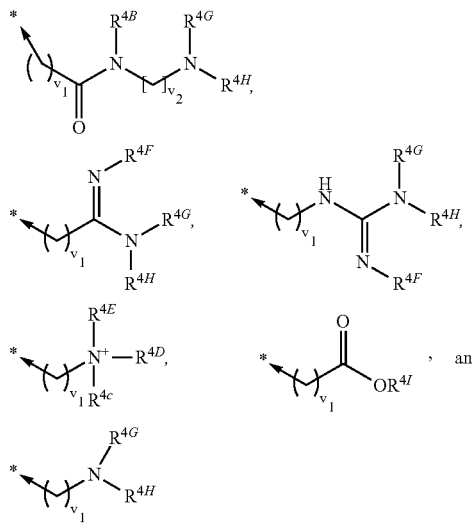

wherein
$R^{4B}$ is hydrogen or $C_1$-$C_6$-alkyl;
$R^{4C}$, $R^{4D}$, $R^{4E}$ are each $C_1$-$C_6$-alkyl, and the nitrogen to which they are attached is quaternary and carries a positive charge; and additionally any two of $R^{4C}$, $R^{4D}$, $R^{4E}$ may be joined to form a ring, optionally containing a second heteroatom selected from oxygen or nitrogen;
one of $R^{4C}$, $R^{4D}$, $R^{4E}$ is a lone pair and the other groups are as defined above, and the nitrogen to which they are attached is tertiary;
$R^{4F}$ and $R^{4I}$ are independently hydrogen or $C_1$-$C_6$-alkyl;
$R^{4G}$ and $R^{4H}$ are independently hydrogen or $C_1$-$C_6$-alkyl, or $R^{4G}$ and $R^{4H}$ taken together with the nitrogen to which they are attached form a monocyclic heterocyclic ring of 5 to 7 ring atoms which may contain a further heteroatom selected from N, O and S; and
v1 and v2 are each independently 0-5.

14. A compound of claim 1, wherein the compound is a pharmaceutically acceptable salt.

* * * * *

UNITED STATES PATENT AND TRADEMARK OFFICE
CERTIFICATE OF CORRECTION

PATENT NO. : 8,198,288 B2
APPLICATION NO. : 12/264621
DATED : June 12, 2012
INVENTOR(S) : Nicholas Charles Ray et al.

It is certified that error appears in the above-identified patent and that said Letters Patent is hereby corrected as shown below:

Column 35,
Intermediate 22, "Br" should read -- Br⁻ --

Column 37,
Structure 26, "Br" should read -- Br⁻ --

Column 75,
Structure 29, "Br" should read -- Br⁻ --

Column 86,
Example 41,

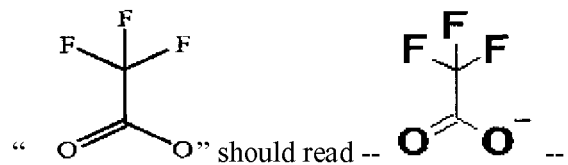

Column 88,
Example 44, "Br" should read -- Br⁻ --

Column 88,
Structure 45, "Br" should read -- Br⁻ --

Signed and Sealed this
Thirteenth Day of November, 2012

David J. Kappos
*Director of the United States Patent and Trademark Office*

CERTIFICATE OF CORRECTION (continued)
U.S. Pat. No. 8,198,288 B2

Column 88,
Structure 45,

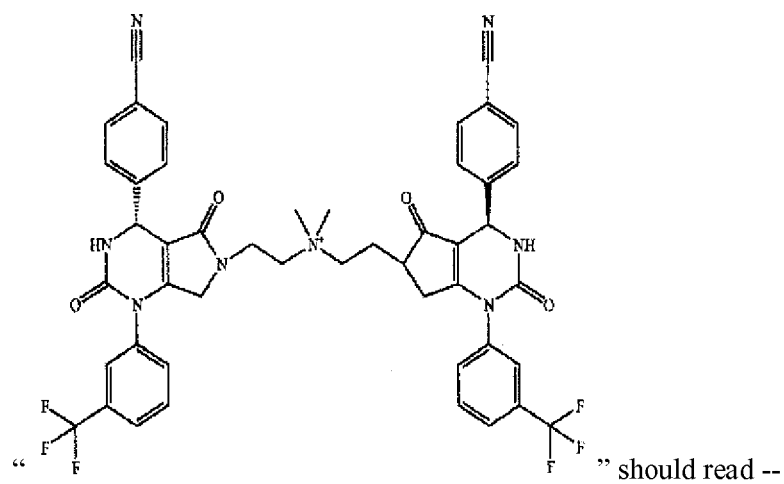

" should read --

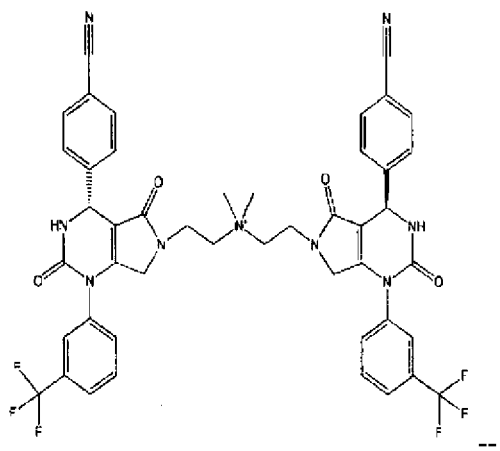

--

Column 91,
Structure 49,

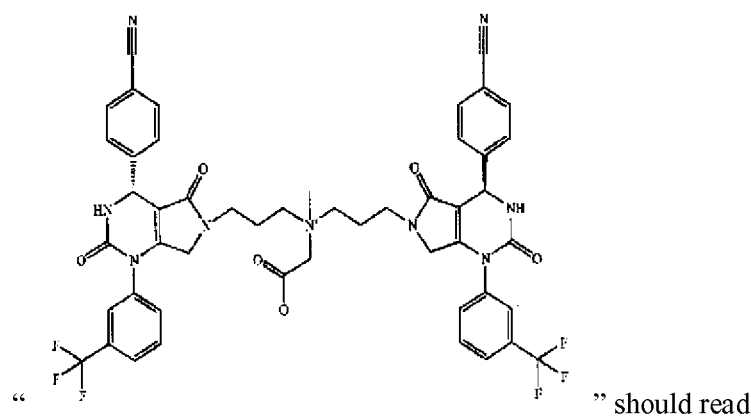

" should read

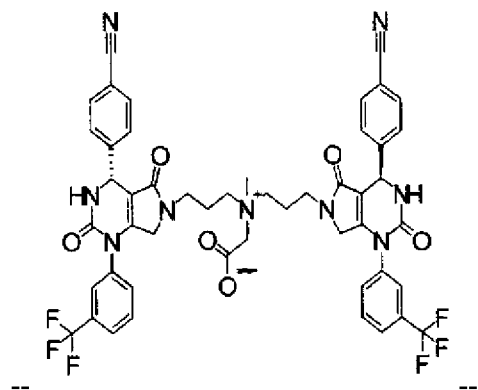
-- --
Column 110,
Line 46, "di-$C_1$-$C_4$-alkylamino" should read -- di-$C_1$-$C_4$-alkylamino, --
Column 111,
Line 31, "v1 and v2 are . . . 0-5." should read -- v1 is 0 and v2 is 0-5. --